(12) United States Patent
Chambers et al.

(10) Patent No.: US 9,260,527 B2
(45) Date of Patent: Feb. 16, 2016

(54) ANTI-HUMAN CXCR4 ANTIBODIES AND METHODS OF MAKING SAME

(71) Applicant: SDIX, LLC, Rockville, MD (US)

(72) Inventors: Ross S. Chambers, Hockessin, DE (US); Michael C. Brown, North East, MD (US); Dale V. Onisk, Conowingo, MD (US); L. Joe Stafford, Newark, DE (US); Fenglin Yin, Naperville, IL (US)

(73) Assignee: SDIX, LLC, Rockville, MD (US)

( * ) Notice: Subject to any disclaimer, the term of this patent is extended or adjusted under 35 U.S.C. 154(b) by 0 days.

(21) Appl. No.: 14/217,841

(22) Filed: Mar. 18, 2014

(65) Prior Publication Data

US 2014/0286936 A1 Sep. 25, 2014

Related U.S. Application Data

(60) Provisional application No. 61/800,963, filed on Mar. 15, 2013.

(51) Int. Cl.
*C07K 16/28* (2006.01)
*C12N 15/09* (2006.01)
*C12N 15/63* (2006.01)

(52) U.S. Cl.
CPC ............ *C07K 16/2866* (2013.01); *C12N 15/09* (2013.01); *C12N 15/63* (2013.01); *C07K 2317/76* (2013.01)

(58) Field of Classification Search
CPC ........... C07K 16/2866; C07K 2317/76; C12N 15/09; C12N 15/63
See application file for complete search history.

(56) References Cited

U.S. PATENT DOCUMENTS

| | | | |
|---|---|---|---|
| 3,691,016 A | 9/1972 | Patel | |
| 3,969,287 A | 7/1976 | Jaworek et al. | |
| 4,179,337 A | 12/1979 | Davis et al. | |
| 4,195,128 A | 3/1980 | Hildebrand et al. | |
| 4,229,537 A | 10/1980 | Hodgins et al. | |
| 4,247,642 A | 1/1981 | Hirohara et al. | |
| 4,301,144 A | 11/1981 | Iwashita et al. | |
| 4,330,440 A | 5/1982 | Ayers et al. | |
| 4,496,689 A | 1/1985 | Mitra | |
| 4,640,835 A | 2/1987 | Shimizu et al. | |
| 4,670,417 A | 6/1987 | Iwasaki et al. | |
| 4,791,192 A | 12/1988 | Nakagawa et al. | |
| 5,530,101 A | 6/1996 | Queen et al. | |
| 5,585,089 A | 12/1996 | Queen et al. | |
| 5,693,761 A | 12/1997 | Queen et al. | |
| 5,693,762 A | 12/1997 | Queen et al. | |
| 5,821,337 A | 10/1998 | Carter et al. | |
| 5,837,242 A | 11/1998 | Holliger et al. | |
| 5,859,205 A | 1/1999 | Adair et al. | |
| 6,054,297 A | 4/2000 | Carter et al. | |
| 6,086,875 A | 7/2000 | Blumberg et al. | |
| 6,180,370 B1 | 1/2001 | Queen et al. | |
| 6,586,207 B2 | 7/2003 | Tirrell et al. | |
| 6,602,684 B1 | 8/2003 | Umana et al. | |
| 6,632,927 B2 | 10/2003 | Adair et al. | |
| 6,639,055 B1 | 10/2003 | Carter et al. | |
| 6,719,971 B1 | 4/2004 | Carter et al. | |
| 6,737,056 B1 | 5/2004 | Presta | |
| 7,022,500 B1 | 4/2006 | Queen et al. | |
| 7,083,784 B2 | 8/2006 | Dall'Acqua et al. | |
| 7,122,637 B2 | 10/2006 | Presta | |
| 7,139,665 B2 | 11/2006 | Datta et al. | |
| 7,198,915 B2 | 4/2007 | Tirrell et al. | |
| 7,214,775 B2 | 5/2007 | Hanai et al. | |
| 7,230,068 B2 | 6/2007 | Wilson | |
| 7,317,091 B2 | 1/2008 | Lazar et al. | |
| 7,332,581 B2 | 2/2008 | Presta | |
| 7,335,742 B2 | 2/2008 | Presta | |
| 7,401,284 B2 | 7/2008 | Bollano et al. | |
| 7,416,727 B2 | 8/2008 | Presta | |
| 7,449,443 B2 | 11/2008 | Tirrell et al. | |
| 7,497,862 B2 | 3/2009 | Viola | |
| 7,504,256 B1 | 3/2009 | Ogawa et al. | |
| 7,517,670 B2 | 4/2009 | Umana et al. | |
| 7,521,541 B2 | 4/2009 | Eigenbrot et al. | |
| 7,566,771 B1 | 7/2009 | Adair et al. | |
| 7,610,156 B2 | 10/2009 | Desjarlais et al. | |
| 7,651,688 B2 | 1/2010 | Hanai et al. | |
| 7,655,228 B2 | 2/2010 | Hanai et al. | |
| 7,670,600 B2 | 3/2010 | Dall'Acqua et al. | |
| 7,682,610 B2 | 3/2010 | Hanai et al. | |
| 7,682,611 B2 | 3/2010 | Hanai et al. | |
| 7,687,061 B2 | 3/2010 | Hanai et al. | |

(Continued)

FOREIGN PATENT DOCUMENTS

| | | |
|---|---|---|
| WO | 87/05330 A1 | 9/1987 |
| WO | 92/11018 A1 | 7/1992 |
| WO | 94/13804 A1 | 6/1994 |
| WO | 98/48032 A2 | 10/1998 |
| WO | 00/61739 A1 | 10/2000 |
| WO | 01/29246 A1 | 4/2001 |
| WO | 02/30954 A1 | 4/2002 |
| WO | 02/31140 A1 | 4/2002 |
| WO | 03/011161 A1 | 2/2003 |
| WO | 03/073238 A2 | 9/2003 |
| WO | 2005035727 A2 | 4/2005 |
| WO | 2005074524 A2 | 8/2005 |

OTHER PUBLICATIONS

Paul, WE. Fundamental Immunology, 3rd ed. Raven Press, NY, Chap. 9, pp. 292-295, 1993.*
Rudikoff S. et al. Proc. Natl. Acad. Sci. USA, 79:1979-1983, 1982.*
Colman, PM. Research in Immunology, Elsevier, NY, 145(1):33-36, 1994.*
Aplin and Wriston, 1981, CRC Crit. Rev. Biochem. 259-306.
Hakimuddin et al., 1987, Arch. Biochem. Biophys. 259:52.
Edge et al., 1981, Anal. Biochem. 118:131.
Thotakura et al., 1987, Meth. Enzymol. 138:350.
Duksin, D. et al., 1982, J. Biol. Chem. 257:3105.

(Continued)

*Primary Examiner* — Robert Landsman

(74) *Attorney, Agent, or Firm* — Millen, White, Zelano & Branigan, P.C.; Larry S. Millstein

(57) ABSTRACT

The present invention provides novel antibodies to human CXCR4 with high affinity to the target and the ability to act potently as antagonists. The antibodies disclosed herein bind to a diverse range of epitopes.

14 Claims, 41 Drawing Sheets

(56) References Cited

U.S. PATENT DOCUMENTS

| | | | |
|---|---|---|---|
| 7,704,497 B2 | 4/2010 | Dall'Acqua et al. |
| 7,708,992 B2 | 5/2010 | Hanai et al. |
| 7,708,997 B2 | 5/2010 | Hanai et al. |
| 7,718,175 B2 | 5/2010 | Hanai et al. |
| 7,723,070 B2 | 5/2010 | Tirrell et al. |
| 7,737,226 B2 | 6/2010 | Wilson |
| 7,763,246 B2 | 7/2010 | Hanai et al. |
| 7,820,766 B2 | 10/2010 | Wilson |
| 7,855,275 B2 | 12/2010 | Eigenbrot et al. |
| 7,906,329 B2 | 3/2011 | Umana et al. |
| 8,008,428 B2 | 8/2011 | Wilson |
| 8,012,476 B2 | 9/2011 | Dall'Acqua et al. |
| 8,084,582 B2 | 12/2011 | Dahiyat et al. |
| 8,097,702 B2 | 1/2012 | Cho et al. |
| 8,119,603 B2 | 2/2012 | Cho et al. |
| 8,124,731 B2 | 2/2012 | Lazar et al. |
| 8,163,551 B2 | 4/2012 | Alley et al. |
| 8,188,231 B2 | 5/2012 | Lazar et al. |
| 8,232,371 B2 | 7/2012 | Cho et al. |
| 8,309,300 B2 | 11/2012 | Junutula et al. |
| 8,323,962 B2 | 12/2012 | Dall'Acqua et al. |
| 8,475,792 B2 | 7/2013 | Dall'Acqua et al. |
| 8,574,907 B2 | 11/2013 | Alley et al. |
| 8,623,644 B2 | 1/2014 | Umana et al. |
| 8,629,248 B2 | 1/2014 | Umana et al. |
| 8,679,491 B2 | 3/2014 | Hanai et al. |
| 8,734,791 B2 | 5/2014 | Lazar et al. |
| 8,778,880 B2 | 7/2014 | Cho et al. |
| 8,795,661 B2 | 8/2014 | Dall'Acqua et al. |
| 8,906,676 B2 | 12/2014 | Cho et al. |
| 8,907,064 B2 | 12/2014 | Cho et al. |
| 2001/0035606 A1 | 11/2001 | Schoen |
| 2003/0003097 A1 | 1/2003 | Reff et al. |
| 2003/0039645 A1 | 2/2003 | Adair et al. |
| 2003/0157108 A1 | 8/2003 | Presta |
| 2003/0190311 A1 | 10/2003 | Dall'Acqua et al. |
| 2004/0013210 A1 | 1/2004 | Bollano et al. |
| 2004/0053390 A1 | 3/2004 | Datta et al. |
| 2004/0058415 A1 | 3/2004 | Tirrell et al. |
| 2004/0072290 A1 | 4/2004 | Umana et al. |
| 2004/0162574 A1 | 8/2004 | Viola |
| 2004/0191244 A1 | 9/2004 | Presta |
| 2004/0214988 A1 | 10/2004 | Tirrell et al. |
| 2004/0228856 A1 | 11/2004 | Presta |
| 2005/0054832 A1 | 3/2005 | Lazar et al. |
| 2005/0074843 A1 | 4/2005 | Umana et al. |
| 2005/0079605 A1 | 4/2005 | Umana et al. |
| 2005/0085619 A1 | 4/2005 | Wilson |
| 2005/0114037 A1 | 5/2005 | Desjarlais et al. |
| 2005/0118174 A1 | 6/2005 | Presta |
| 2005/0170404 A1 | 8/2005 | Cho et al. |
| 2005/0220762 A1 | 10/2005 | Cho et al. |
| 2005/0233382 A1 | 10/2005 | Presta |
| 2005/0272916 A1 | 12/2005 | Hanai et al. |
| 2005/0276805 A1 | 12/2005 | Hanai et al. |
| 2006/0024298 A1 | 2/2006 | Lazar et al. |
| 2006/0024800 A1 | 2/2006 | Hanai et al. |
| 2006/0121032 A1 | 6/2006 | Dahiyat et al. |
| 2006/0160996 A9 | 7/2006 | Lazar et al. |
| 2006/0177865 A1 | 8/2006 | Datta et al. |
| 2006/0194957 A1 | 8/2006 | Presta |
| 2006/0198840 A1 | 9/2006 | Dall'Acqua et al. |
| 2006/0235208 A1 | 10/2006 | Lazar et al. |
| 2007/0020260 A1 | 1/2007 | Presta |
| 2007/0092940 A1 | 4/2007 | Eigenbrot et al. |
| 2007/0122403 A1 | 5/2007 | Dall'Acqua et al. |
| 2007/0123691 A1 | 5/2007 | Wilson |
| 2007/0123693 A1 | 5/2007 | Wilson |
| 2007/0148170 A1 | 6/2007 | Desjarlais et al. |
| 2007/0166300 A1 | 7/2007 | Hanai et al. |
| 2007/0166301 A1 | 7/2007 | Hanai et al. |
| 2007/0166302 A1 | 7/2007 | Hanai et al. |
| 2007/0166303 A1 | 7/2007 | Hanai et al. |
| 2007/0166304 A1 | 7/2007 | Hanai et al. |
| 2007/0166305 A1 | 7/2007 | Hanai et al. |
| 2007/0202098 A1 | 8/2007 | Lazar et al. |
| 2007/0207151 A1 | 9/2007 | Hanai et al. |
| 2007/0219133 A1 | 9/2007 | Lazar et al. |
| 2007/0224189 A1 | 9/2007 | Lazar et al. |
| 2007/0224192 A1 | 9/2007 | Lazar et al. |
| 2008/0026422 A1 | 1/2008 | Tirrell et al. |
| 2008/0095762 A1 | 4/2008 | Presta |
| 2008/0097083 A1 | 4/2008 | Cho et al. |
| 2008/0103293 A1 | 5/2008 | Cho et al. |
| 2008/0103294 A1 | 5/2008 | Cho et al. |
| 2008/0108791 A1 | 5/2008 | Cho et al. |
| 2008/0108797 A1 | 5/2008 | Cho et al. |
| 2008/0113410 A1 | 5/2008 | Desjarlais et al. |
| 2008/0114154 A1 | 5/2008 | Cho et al. |
| 2008/0114155 A1 | 5/2008 | Cho et al. |
| 2008/0146781 A1 | 6/2008 | Cho et al. |
| 2008/0160609 A1 | 7/2008 | Tirrell et al. |
| 2008/0161539 A1 | 7/2008 | Cho et al. |
| 2008/0177043 A1 | 7/2008 | Hanai et al. |
| 2008/0181890 A1 | 7/2008 | Lazar et al. |
| 2008/0206867 A1 | 8/2008 | Desjarlais et al. |
| 2008/0207877 A1 | 8/2008 | Cho et al. |
| 2008/0242845 A1 | 10/2008 | Lazar et al. |
| 2008/0274108 A1 | 11/2008 | Presta |
| 2008/0292621 A1 | 11/2008 | Lazar et al. |
| 2008/0300163 A1 | 12/2008 | Cho et al. |
| 2009/0053211 A9 | 2/2009 | Lazar et al. |
| 2009/0068175 A1 | 3/2009 | Lazar et al. |
| 2009/0142340 A1 | 6/2009 | Lazar et al. |
| 2009/0175865 A1 | 7/2009 | Eigenbrot et al. |
| 2009/0203078 A1 | 8/2009 | Ogawa et al. |
| 2009/0214526 A1 | 8/2009 | Lazar et al. |
| 2009/0221790 A1 | 9/2009 | Tirrell et al. |
| 2009/0304690 A1 | 12/2009 | Umana et al. |
| 2009/0317869 A1 | 12/2009 | Alley et al. |
| 2010/0003766 A1 | 1/2010 | Eigenbrot et al. |
| 2010/0184193 A1 | 7/2010 | Tirrell et al. |
| 2010/0189718 A1 | 7/2010 | Dall'Acqua et al. |
| 2010/0196371 A1 | 8/2010 | Hanai et al. |
| 2010/0217050 A1 | 8/2010 | Wilson |
| 2010/0255013 A1 | 10/2010 | Presta |
| 2011/0004590 A1 | 1/2011 | Lilley et al. |
| 2011/0086050 A1 | 4/2011 | Presta |
| 2011/0137017 A1 | 6/2011 | Eigenbrot et al. |
| 2011/0142825 A1 | 6/2011 | Umana et al. |
| 2011/0250681 A1 | 10/2011 | Lazar et al. |
| 2011/0269974 A1 | 11/2011 | Wilson |
| 2011/0293632 A1 | 12/2011 | Presta |
| 2011/0294984 A1 | 12/2011 | Umana et al. |
| 2011/0311454 A1 | 12/2011 | Dall'Acqua et al. |
| 2012/0077228 A1 | 3/2012 | Tirrell et al. |
| 2012/0122206 A1 | 5/2012 | Umana et al. |
| 2012/0142896 A1 | 6/2012 | Cho et al. |
| 2012/0183997 A1 | 7/2012 | Alley et al. |
| 2012/0258092 A1 | 10/2012 | Dahiyat et al. |
| 2013/0012690 A1 | 1/2013 | Tirrell et al. |
| 2013/0052135 A1 | 2/2013 | Dall'Acqua et al. |
| 2013/0058919 A1 | 3/2013 | Lazar et al. |
| 2013/0272964 A1 | 10/2013 | Dall'Acqua et al. |
| 2014/0031536 A1 | 1/2014 | Alley et al. |
| 2014/0127777 A1 | 5/2014 | Tirrell et al. |
| 2014/0147436 A1 | 5/2014 | Presta |
| 2014/0234300 A1 | 8/2014 | Hanai et al. |
| 2014/0255991 A1 | 9/2014 | Tirrell et al. |
| 2014/0296145 A1 | 10/2014 | Cho et al. |
| 2014/0342404 A1 | 11/2014 | Presta |

OTHER PUBLICATIONS

"2005-2006 PEG Catalog from Nektar Therapeutics, website address:http://sejinbio.co.kr/Catalogue/Nektar" (34 pages). Dated and copyrighted in 2005 by Nektar Therapeutics.

Carnec, X. et al., "Anti-CXCR4 Monoclonal Antibodies Recognizing Overlapping Epitopes Differ Significantly in Their Ability to Inhibit Entry of Human Immunodeficiency Virus Type 1," Journal of Virology, 2005, vol. 79, No. 3, pp. 1930-1933.

(56) References Cited

OTHER PUBLICATIONS

Berchiche, Y. A. et al., "Direct Assessment of CXCR4 Mutant Conformations Reveals Complex Link between Receptor Structure and G-alpha-i Activation," The Journal of Biological Chemistry, 2007, vol. 282, pp. 5111-5115.
Rubin, J. B. et al., "Chemokine Signaling in Cancer: One Hump or Two?" Semin Cancer Biol., Apr. 1, 2010.
Busillo, J. M. et al, "Regulation of CXCR4 Signaling," Biochim Biophys Acta, 2007, Apr. 2007, vol. 1768, No. 4, pp. 952-963.
Retter, I. et al., "VBASE2, an integrative V gene database," Nucleic Acids Research, 2005, vol. 33, pp. D671-D674.
Edelman et al., 1969, Proc Natl Acad Sci USA 63:78-85.
J.W. Chin et al., 2002, Journal of the American Chemical Society 124:9026-9027.
J.W. Chin & P.G. Schultz, 2002, Chem Bio Chem 11:1135-1137.
J.W. Chin et al., 2002, PICAS USA 99:11020-11024.
L. Wang & P.G. Schultz, 2002, Chem. 1-11 "Expanding the genetic code."
Simon et al., 1992, PNAS USA 89(20):9367.
Cropp & Shultz, 2004, Trends Genet. 20(12):625-630.
Anderson et al., 2004, Proc Natl Acad Sci USA 101(2):7566-7571.
Zhang Z. et al., 2003, 303(5656):371-373.
Chin et al., 2003, Science 301(5635):964-967.
Davis et al., 2002, Immunological Reviews 190:123-136.
Kabat et al., 1991, "Sequences of Proteins of Immunological Interest" 5th Ed. Public Health Service, NIH, Bethesda, MD / BOOK (cover pages—table of contents).
Chothia and Lesk, 1987, J. Mol. Biol. 196:901-917.
Ward et al., 1989, Nature 341:544-546.
Bird et al., 1988, Science 242:423-426.
Huston et al., 1988, Proc. Natl. Acad. Sci. USA 85:5879-5883.
Tomlinson et al., 2000, Methods Enzymol. 326:461-479.
Holliger et al., 1993, Proc. Natl. Acad. Sci. USA 90:6444-6448.
Reiter et al., 1996, Nature Biotech. 14:1239-1245.
Jones, 1986, Nature 321:522-525.
Verhoeyen et al., 1988, Science 239:1534-1536.
Roque et al., 2004, Biotechnol. Prog. 20:639-654.
Tsurushita & Vasquez, 2004, Humanization of Monoclonal Antibodies, MolecularBiology of B Cells, Elsevier Science USA 533-545.
Riechmann et al., 1988, Nature 332:323-329.
Queen et al., 1989, Proc Natl Acad Sci. USA 86:10029-10033.
He et al, 1998, J. Immunol. 160:1029-1035.
Carter et al., 1992, Proc Natl Acad Sci USA 89:4285-4289.
Presta et al., 1997, Cancer Res. 57(20):4593-4599.
Gorman et al., 1991, Proc. Natl. Acad. Sci. USA 88:4181-4185.
O'Connor et al., 1998, Protein Eng 11:321-328.
Roguska et al., 1994, Proc. Natl. Acad. Sci. USA 91:969-973.
Wu et al., 1999, J. Mol. Biol. 294:151-162.
Baca et al., 1997, J. Biol. Chem. 272(16):10678-10684.
Rosok et al., 1996, J. Biol. Chem. 271(37):22611-22618.
Radar et al., 1998, Proc. Natl. Acad. Sci. USA 95:8910-8915.
Krauss et al., 2003, Protein Engineering 16(10):753-759.
Tan et al., 2002, J. Immunol. 169:1119-1125.
De Pascalis et al., 2002, J. Immunol. 169:3076-3084.
Hu et al., 1996, Cancer Res. 56:3055-3061.
Marks et al., 1992, Biotechnology 10:779-783.
Barbas, et al., 1994, Proc. Nat. Acad. Sci. USA 91:3809-3813.
Schier et al., 1995, Gene 169:147-155.
Yelton, De et al., 1995, J. Immunol. 155:1994-2004.
Jackson et al., 1995, J. Immunol. 154(7):3310-3319.
Hawkins et al., 1992, J. Mol. Biol. 226:889-896.
T.E. Creighton, 1984, Proteins: Structure and Molecular Principles, W. H. Freeman & Co., San Francisco, pp. 286-295.
Umana et al., 1999, Nat Biotechnol 17:176-180.
Davies et al., 2001, Biotechnol Bioeng 74:288-294.
Shields et al., 2002, J. Biol. Chem. 277:26733-26740.
Shinkawa et al., 2003, J. Biol. Chem. 278:3466-3473.

\* cited by examiner

| | | X39 | X122 | X132 | X142 | X197 |
|---|---|---|---|---|---|---|
| Transfected cells | N-term (GVNK) | 9 | nd | 2 | nd | nd |
| | ECL1 (NN) | 86 | nd | 68 | nd | nd |
| | ECL2 (NEAQ) | 83 | 5 | 53 | 7 | 8 |
| | ECL2 (FND) | 144 | 108 | 77 | 114 | 102 |
| | ECL3 (EIENT) | 113 | 80 | 127 | 138 | 132 |
| | N-term/ECL3 (H12M3N) | 26 | 64 | 56 | 120 | 104 |
| | ECL1/ECL2 (M12H3N) | 81 | 17 | 50 | 13 | 14 |
| | Wild type | 100 | 100 | 100 | 100 | 100 |
| | Control (CD20) | 15 | 17 | 2 | 7 | 8 |
| | Epitope Bin | N | 2 | N2 | 2 | 2 |

FIG 2A

|  | | Hybridoma clone | | | | |
|---|---|---|---|---|---|---|
| | | AA7 | AA17 | AA23 | AA36 | AA59 |
| Transfected cells | N-term (GVNK) | 6 | nd | nd | nd | nd |
| | ECL1 (NN) | 109 | nd | nd | nd | nd |
| | ECL2 (NEAQ) | 80 | 24 | 19 | 1 | 9 |
| | ECL2 (FND) | 115 | 118 | 100 | 132 | 107 |
| | ECL3 (EIENT) | 138 | 129 | 130 | 152 | 127 |
| | N-term/ECL3 (H12M3N) | 15 | 124 | 110 | 148 | 113 |
| | ECL1/ECL2 (M12H3N) | 95 | 18 | 20 | 2 | 9 |
| | Wild type | 100 | 100 | 100 | 100 | 100 |
| | Control (CD20) | 8 | 12 | 7 | 9 | 7 |
| | Epitope Bin | N | 2 | 2 | 2 | 2 |

FIG 2B

| | | AA101 | C171 | C172 | C173 | 12G5 |
|---|---|---|---|---|---|---|
| Transfected cells | N-term (GVNK) | nd | nd | nd | nd | 63 |
| | ECL1 (NN) | nd | nd | nd | nd | 73 |
| | ECL2 (NEAQ) | 12 | 4 | 4 | 16 | 8 |
| | ECL2 (FND) | 94 | 170 | 142 | 153 | 120 |
| | ECL3 (EIENT) | 122 | 128 | 145 | 143 | 125 |
| | N-term/ECL3 (H12M3N) | 106 | 126 | 112 | 130 | 109 |
| | ECL1/ECL2 (M12H3N) | 11 | 11 | 12 | 24 | 5 |
| | Wild type | 100 | 100 | 100 | 100 | 100 |
| | Control (CD20) | 6 | 2 | 11 | 19 | 6 |
| | Epitope Bin | 2 | 2 | 2 | 2 | 2 |

FIG 2C

|  | Flow Cytometry | | | |
|---|---|---|---|---|
| Clone name | Jurkat | HEK 293 | Ramos | CEM |
| AA7.1 | ++ | +++ | - | ++ |
| AA17.1 | ++ | +++ | ++ | +++ |
| AA23.1 | ++ | +++ | nd | nd |
| AA36.1 | + | ++ | - | - |
| X197.1 | ++ | +++ | ++ | + |
| AA80 | ++ | +++ | +++ | +++ |
| AA101.1 | ++ | +++ | ++ | ++ |
| X39.1 | ++ | +++ | + | + |
| X122.1 | +++ | +++ | - | ++ |
| X132.1 | +++ | +++ | ++ | +++ |
| X142.1 | - | +++ | nd | nd |
| X219.1 | + | +++ | nd | nd |
| AA59.1 | ++ | ++ | nd | nd |

FIG. 3

Flow cytometry titration curves on Jurkat cells

Flow cytometry titration curves on transfected HEK293 cells

| Clone name | Antagonist Assay (EC50 nM) | |
| --- | --- | --- |
| | cAMP | Calcium |
| AA7.1 | none | nd |
| AA17.1 | 458 | none |
| AA23.1 | none | nd |
| AA36.1 | 1689 | none |
| X197.1 | 318 | none |
| AA80 | none | nd |
| AA101.1 | 27 | 0.2 |
| X39.1 | none | nd |
| X122.1 | 14 | 0.8 |
| X132.1 | 6 | 3 |
| X142.1 | none | nd |
| X219.1 | none | nd |
| AA59.1 | nd | nd |

FIG. 6

| Clone name | VH Genes | | | | VK Germline |
|---|---|---|---|---|---|
| | VH Germline | VH CDR1 | VH CDR2 | VH CDR3 | |
| AA7.1 | musIGHV160 | GFSFSNYG | INSIGGKT | ARFNWYFDV | musIGKV122 |
| AA17.1 | musIGHV158 | GFTFTDYY | IRNKANGYTT | ARDRNGDSAY | musIGKV046 |
| AA23.1 | musIGHV158 | GFTFTDYY | IRNKANGYTT | ARDNGGYDYARGYAMDY | musIGKV046 |
| AA36.1 | musIGHV158 | GFTFTDYY | IRNKANGYTK | ARDYDDDY | musIGKV046 |
| X197.1 | musIGHV158 | GFTFTDYY | IRNKANGYTT | ARDLGDDY | musIGKV122 |
| AA80 | musIGHV131 | GFAFSSYD | ISSGGSYT | ARHRDKPLDY | musIGKV046 |
| AA101.1 | musIGHV158 | GFTFTDYY | IRNKANGYTT | ARDPLGRFDY | musIGKV066 |
| X39.1 | musIGHV114 | GFTFSNYW | IRLKSNNYAK | TMLGYY | musIGKV046 |
| X122.1 | musIGHV158 | GFTFTDYY | IRNKANGYTT | ARDGTTMGAADY | musIGKV046 |
| X132.1 | musIGHV363 | GYTFFRSYG | IYPRSGNT | ARDSKDYAMDY | musIGKV097 |
| X142.1 | musIGHV158 | GFTFTDYY | IRNKANGYTT | ARDAGSGSHYFDY | musIGKV046 |
| X219.1 | musIGHV158 | GFTFTDYY | IRNKANGYTT | ARGTGHFDY | musIGKV046 |
| AA59.1 | musIGHV528 | GYTFTDYH | INPYNGDI | ARGGQLGLAY | musIGKV046 |

FIG 7A

| VK Genes | | | Epitope |
|---|---|---|---|
| VK CDR1 | VK CDR2 | VK CDR3 | |
| QSLVHSNGNTF | KVS | SQSTHVPWT | N |
| QSLFNSRTRKNY | WAS | KQSYYT | ECL2 |
| QSLLNSRTRKNY | WAS | TQSYNLRT | ECL2 |
| QSLFNSRTRKNY | WAS | KQSYYLRT | ECL2 |
| QSLFNSRTRKNY | WAS | KQSYYLRA | ECL2 |
| QSLVHSNGNTY | KVS | SQITHVPWT | N |
| QSLFNSRTRKNY | WAS | TQSSYLRT | ECL2 |
| QSVSSSRQSY | YAS | QHSWEIPYT | N |
| QSLFNSRTRKNY | WAF | KQSYYLRT | ECL2 |
| QSLLDSDGKTY | LMS | WQGTHFPHT | N-ECL2 |
| QSLFNSRTRKNY | WAL | KQSYYLRT | ECL2 |
| QSLFNSRTRKNY | WAS | KQSYYLRT | ECL2 |
| QSLFNSRTRKNY | WAL | KQSYYLRT | ECL2 |

Antibody sequences from hybridoma clones (VH and VK regions)

Anti-CXCR4 VH, clone AA7

```
GAGGTGCAGGGGGTGGAGTCTGGGGGAGGCTTAGTGAAGCCTGGAGGGTCCCTGAAACTCTCCTGTGCAGCCTCTGG
ATTCTCTTTCAGTAACTATGGCATGTCTTGGGTTCGCCAGACTCCGGAGAAGAGGCTGGAGTGGGTCGCAGCCATTA
ATAGTATTGGTGGTAAGACCTACTATCCAGACACTGTGAAGGGCCGATTCACCATCTCCAGGGACAATGCCAAGAAC
ACCCTGTACCTGCAAATGAGCAGTCTGAGGTCTGGTGACACAGCCTTGTATTACTGTGCAAGATTTAACTGGTACTT
CGATGTCTGGGGCACAGGGACCACTCTCACAGTCTCCTCA (SEQ ID NO: 79)
```

Translation

```
  1 E  V  Q  G  V  E  S  G  G  G  L  V  K  P  G  G  S  L  K  L
  1 GAGGTGCAGGGGGTGGAGTCTGGGGGAGGCTTAGTGAAGCCTGGAGGGTCCCTGAAACTC

VH CDR1 (SEQ ID NO: 1)
 21 S  C  A  A  S  G  F  S  F  S  N  Y  G  M  S  W  V  R  Q  T
 61 TCCTGTGCAGCCTCTGGATTCTCTTTCAGTAACTATGGCATGTCTTGGGTTCGCCAGACT

VH CDR2 (SEQ ID NO: 2)
 41 P  E  K  R  L  E  W  V  A  A  I  N  S  I  G  G  K  T  Y  Y
121 CCGGAGAAGAGGCTGGAGTGGGTCGCAGCCATTAATAGTATTGGTGGTAAGACCTACTAT

61 P  D  T  V  K  G  R  F  T  I  S  R  D  N  A  K  N  T  L  Y
181 CCAGACACTGTGAAGGGCCGATTCACCATCTCCAGGGACAATGCCAAGAACACCCTGTAC

VH CDR3 (SEQ ID NO: 3)
 81 L  Q  M  S  S  L  R  S  G  D  T  A  L  Y  Y  C  A  R  F  N
241 CTGCAAATGAGCAGTCTGAGGTCTGGTGACACAGCCTTGTATTACTGTGCAAGATTTAAC

101 W  Y  F  D  V  W  G  T  G  T  T  L  T  V  S  S  (SEQ ID NO: 80)
301 TGGTACTTCGATGTCTGGGGCACAGGGACCACTCTCACAGTCTCCTCA (SEQ ID NO: 79)
```

FIG. 9

Anti-CXCR4 VK, clone AA7

```
GACGTTGTGATGACCCAGACTCCACTCTCCCTGCCTGTCAGTCTTGGAGATCAAGCCTCCATCTCTTGCAGATCTAG
TCAGAGCCTTGTACACAGTAATGGAAACACCTTTTTACATTGGTACCTGCTGAAGCCAGGCCAGTCTCCAAAGCTCC
TGATCTACAAAGTTTCCAGCCGATTTTCTGGGGTCCCAGACAGGTTCAGTGGCAGTGGATCAGGGACCGATTTCACA
CTCAAGATCACCAGAGTGGAGGCTGAGGATCTGGGACTTTATTTCTGCTCTCAAAGTACACATGTTCCGTGGACGTT
CGGTGGAGGCACCAAGCTGGAAATAAAAC SEQ ID NO: 81
```

Translate

```
  1 D   V   V   M   T   Q   T   P   L   S   L   P   V   S   L   G   D   Q   A   S
  1 GACGTTGTGATGACCCAGACTCCACTCTCCCTGCCTGTCAGTCTTGGAGATCAAGCCTCC

VK CDR1(SEQ ID NO: 4)
 21 I   S   C   R   S   S   Q   S   L   V   H   S   N   G   N   T   F   L   H   W
 61 ATCTCTTGCAGATCTAGTCAGAGCCTTGTACACAGTAATGGAAACACCTTTTTACATTGG

VK CDR2(SEQ ID NO: 5)
 41 Y   L   L   K   P   G   Q   S   P   K   L   L   I   Y   K   V   S   S   R   F
121 TACCTGCTGAAGCCAGGCCAGTCTCCAAAGCTCCTGATCTACAAAGTTTCCAGCCGATTT

61 S   G   V   P   D   R   F   S   G   S   G   S   G   T   D   F   T   L   K   I
181 TCTGGGGTCCCAGACAGGTTCAGTGGCAGTGGATCAGGGACCGATTTCACACTCAAGATC

VK CDR3(SEQ ID NO: 6)
 81 T   R   V   E   A   E   D   L   G   L   Y   F   C   S   Q   S   T   H   V   P
241 ACCAGAGTGGAGGCTGAGGATCTGGGACTTTATTTCTGCTCTCAAAGTACACATGTTCCG

101 W   T   F   G   G   G   T   K   L   E   I   K (SEQ ID NO: 82)
301 TGGACGTTCGGTGGAGGCACCAAGCTGGAAATAAAAC (SEQ ID NO: 81)
```

FIG. 10

Anti-CXCR4 VH, clone AA17

GATGTGCACCTGGTGGAGTCTGGAGGAGGCTTGGTACAGCCTGGGGCTTCTCTGAGACTCTCCTGTGCAACTTCTGG
GTTCACCTTCACTGATTACTACATGAGCTGGGTCCGCCAGCCTCCAGGAAAGGCACTTGAGTGGTTGGGTTTTATTA
GAAACAAAGCTAATGGTTACACAACAGAGTACAGTGCATCTGTGAAGGGTCGGTTCACCATCTCCAGAGATAATTCC
CAAAGCATCCTCTATCTTCAAATGAACACACTGAGAGCTGAGGACAGTGCCACTTATTACTGTGCAAGAGATAGGAA
TGGTGACTCCGCTTACTGGGGCCAAGGGACTCTGGTCACTGTCTCTGCA SEQ ID NO: 83

Translate

```
      1 D   V   H   L   V   E   S   G   G   G   L   V   Q   P   G   A   S   L   R   L
      1 GATGTGCACCTGGTGGAGTCTGGAGGAGGCTTGGTACAGCCTGGGGCTTCTCTGAGACTC

VH CDR1(SEQ ID NO: 7)
     21 S   C   A   T   S   G   F   T   F   T   D   Y   Y   M   S   W   V   R   Q   P
     61 TCCTGTGCAACTTCTGGGTTCACCTTCACTGATTACTACATGAGCTGGGTCCGCCAGCCT

VH CDR2(SEQ ID NO: 8)
     41 P   G   K   A   L   E   W   L   G   F   I   R   N   K   A   N   G   Y   T   T
    121 CCAGGAAAGGCACTTGAGTGGTTGGGTTTTATTAGAAACAAAGCTAATGGTTACACAACA

61 E   Y   S   A   S   V   K   G   R   F   T   I   S   R   D   N   S   Q   S   I
    181 GAGTACAGTGCATCTGTGAAGGGTCGGTTCACCATCTCCAGAGATAATTCCCAAAGCATC

81 L   Y   L   Q   M   N   T   L   R   A   E   D   S   A   T   Y   Y   C   A   R
    241 CTCTATCTTCAAATGAACACACTGAGAGCTGAGGACAGTGCCACTTATTACTGTGCAAGA

VH CDR3 (SEQ ID NO: 9)
    101 D   R   N   G   D   S   A   Y   W   G   Q   G   T   L   V   T   V   S   A(SEQ ID:84)
    301 GATAGGAATGGTGACTCCGCTTACTGGGGCCAAGGGACTCTGGTCACTGTCTCTGCA (SEQ ID
NO: 83)
```

FIG. 11

Anti-CXCR4 VK, clone AA17

GATATTCTAATGACCCAGTCTCCATCCTCCCTGGCTGTGTCAGCAGGAGAGAAGGTCACTATGAGCTGCAAATCCAG
TCAGAGTCTGTTCAACAGTAGAACCCGGAAGAACTACTTGGCTTGGTACCAGCAGAAACCAGGGCAGTCTCCTAAAC
TGCTGATCTACTGGGCATCCACTAGGGAATCTGGGGTCCCTGATCGCTTCACAGGCAGTGGATCTGGGACAGATCTC
ACTCTCACCATCAGCAGTGTGCAGGCTGAAGACCTGGCAGTTTATTACTGCAAGCAATCTTATTATACGTTCGGATC
GGGGACCAAGCTGGAGCTGAAACG (SEQ ID NO: 85)

Translate

```
  1 D  I  L  M  T  Q  S  P  S  S  L  A  V  S  A  G  E  K  V  T
  1 GATATTCTAATGACCCAGTCTCCATCCTCCCTGGCTGTGTCAGCAGGAGAGAAGGTCACT

VK CDR1 (SEQ ID NO: 10)
 21 M  S  C  K  S  S  Q  S  L  F  N  S  R  T  R  K  N  Y  L  A
 61 ATGAGCTGCAAATCCAGTCAGAGTCTGTTCAACAGTAGAACCCGGAAGAACTACTTGGCT

VK CDR2 (SEQ ID NO: 11)
 41 W  Y  Q  Q  K  P  G  Q  S  P  K  L  L  I  Y  W  A  S  T  R
121 TGGTACCAGCAGAAACCAGGGCAGTCTCCTAAACTGCTGATCTACTGGGCATCCACTAGG

61 E  S  G  V  P  D  R  F  T  G  S  G  S  G  T  D  L  T  L  T
181 GAATCTGGGGTCCCTGATCGCTTCACAGGCAGTGGATCTGGGACAGATCTCACTCTCACC

VK CDR3 (SEQ ID NO: 12)
 81 I  S  S  V  Q  A  E  D  L  A  V  Y  Y  C  K  Q  S  Y  Y  T
241 ATCAGCAGTGTGCAGGCTGAAGACCTGGCAGTTTATTACTGCAAGCAATCTTATTATACG

101 F  G  S  G  T  K  L  E  L  K  (SEQ ID NO: 86)
301 TTCGGATCGGGGACCAAGCTGGAGCTGAAACG (SEQ ID NO: 85)
```

FIG. 12

Anti-CXCR4 VH, clone AA23

GAGGTGAAGCTGATGGAGTCTGGAGGAGGCTTGGTACAGCCTGGGGCTTCTCTGAGACTCTCCTGTGTAACTTCTGGGT
TCACCTTCACTGATTACTACATGAGCTGGGTCCGCCAGCCTCCAGGAAAGGCACTTGAGTGGTTGGGTTTTATTAGAAA
CAAAGCTAATGGTTACACAACAGACTACAGTGCATCTGTGAAGGGTCGGTTCACCATCTCCAGAGATAATTCCCAAAGC
ATCCTCTATCTTCAAATGAACACACTGAGAGCTGAGGACAGTGCCACTTATTACTGTGCGAGAGATAACGGGGGGTATG
ATTACGCACGGGGCTATGCTATGGACTACTGGGGTCAAGGAACCTCAGTCACTGTCTCTGCA(SEQ ID NO: 87)

Translate
```
    1 E   V   K   L   M   E   S   G   G   G   L   V   Q   P   G   A   S   L   R   L
    1 GAGGTGAAGCTGATGGAGTCTGGAGGAGGCTTGGTACAGCCTGGGGCTTCTCTGAGACTC VH CDR1(SEQ ID NO: 13)
   21 S   C   V   T   S   G   F   T   F   T   D   Y   Y   M   S   W   V   R   Q   P
   61 TCCTGTGTAACTTCTGGGTTCACCTTCACTGATTACTACATGAGCTGGGTCCGCCAGCCT VH CDR2(SEQ ID NO: 14)
   41 P   G   K   A   L   E   W   L   G   F   I   R   N   K   A   N   G   Y   T   T
  121 CCAGGAAAGGCACTTGAGTGGTTGGGTTTTATTAGAAACAAAGCTAATGGTTACACAACA 61 D   Y   S   A   S   V   K   G   R   F   T   I   S   R   D   N   S   Q   S   I
  181 GACTACAGTGCATCTGTGAAGGGTCGGTTCACCATCTCCAGAGATAATTCCCAAAGCATC 81 L   Y   L   Q   M   N   T   L   R   A   E   D   S   A   T   Y   Y   C   A   R
  241 CTCTATCTTCAAATGAACACACTGAGAGCTGAGGACAGTGCCACTTATTACTGTGCGAGA VH CDR3(SEQ ID NO: 15)
  101 D   N   G   G   Y   D   Y   A   R   G   Y   A   M   D   Y   W   G   Q   G   T
  301 GATAACGGGGGGTATGATTACGCACGGGGCTATGCTATGGACTACTGGGGTCAAGGAACC 121 S   V   T   V   S   A   (SEQ ID NO: 88)
  361 TCAGTCACTGTCTCTGCA (SEQ ID NO: 87)
```

FIG. 13

Anti-CXCR4 VK, clone AA23

GATATTGTGATGACCCAATCTCCATCCTCCCTGGCTGTGTCAGCAGGAGAGAAGGTCACTATGAGCTGCAAATCCAG
TCAGAGTCTGCTCAACAGTAGAACCCGAAAGAACTACTTGGCTTGGTACCAGCAGAAACCAGGGCAGTCTCCTAAAC
TACTGATCTACTGGGCATCCACTAGGGAATCTGGGGTCCCTGATCGCTTCACAGGCAGTGGATCTGGGACAGATTTC
ACTCTCACCATCAGCAGTGTGCAGGCTGAAGACCTGGCGGTTTATTACTGCACGCAATCTTATAATCTTCGGACGTT
CGGTGGAGGCACCAAGCTGGAGCTGAAAC (SEQ ID NO: 89)

Translate

```
  1 D   I   V   M   T   Q   S   P   S   S   L   A   V   S   A   G   E   K   V   T
  1 GATATTGTGATGACCCAATCTCCATCCTCCCTGGCTGTGTCAGCAGGAGAGAAGGTCACT

VK CDR1(SEQ ID NO: 16)
 21 M   S   C   K   S   S   Q   S   L   L   N   S   R   T   R   K   N   Y   L   A
 61 ATGAGCTGCAAATCCAGTCAGAGTCTGCTCAACAGTAGAACCCGAAAGAACTACTTGGCT

VK CDR2(SEQ ID NO: 17)
 41 W   Y   Q   Q   K   P   G   Q   S   P   K   L   L   I   Y   W   A   S   T   R
121 TGGTACCAGCAGAAACCAGGGCAGTCTCCTAAACTACTGATCTACTGGGCATCCACTAGG

61 E   S   G   V   P   D   R   F   T   G   S   G   S   G   T   D   F   T   L   T
181 GAATCTGGGGTCCCTGATCGCTTCACAGGCAGTGGATCTGGGACAGATTTCACTCTCACC

VK CDR3(SEQ ID NO: 18)
 81 I   S   S   V   Q   A   E   D   L   A   V   Y   Y   C   T   Q   S   Y   N   L
241 ATCAGCAGTGTGCAGGCTGAAGACCTGGCGGTTTATTACTGCACGCAATCTTATAATCTT

101 R   T   F   G   G   G   T   K   L   E   L   K   (SEQ ID NO: 90)
301 CGGACGTTCGGTGGAGGCACCAAGCTGGAGCTGAAAC  (SEQ ID NO: 89)
```

FIG. 14

Anti-CXCR4 VH, clone AA36

GAGGTGCAGCTTCTGGAGTCTGGAGGAGGCTTGGTACAGCCTGGGGCTTCTCTGAGACTCTCCTGTGCAACTTCTGG
GTTCACCTTCACTGATTACTACATGAGCTGGGTCCGCCAGCCTCCAGGAAAGGCACTTGAGTGGTTGGGTTTTATTA
GAAACAAAGCTAATGGTTACACAAAAGAGTACAGTGCATCTGTGAAGGGTCGGTTCACCATCTCCAGAGATAATTCC
CAAAGCATCCTCTATCTTCAAATGAACACACTGGGAGCTGAGGACAGTGCCACTTATTACTGTGCACGTGACTACGA
CGACGACTACTGGGGCCAAGGCACCACTCTCACAGTCTCCTCA (SEQ ID NO: 91)

Translate

```
      1 E  V  Q  L  L  E  S  G  G  G  L  V  Q  P  G  A  S  L  R  L
      1 GAGGTGCAGCTTCTGGAGTCTGGAGGAGGCTTGGTACAGCCTGGGGCTTCTCTGAGACTC

VH CDR2(SEQ ID NO: 19)
     21 S  C  A  T  S  G  F  T  F  T  D  Y  Y  M  S  W  V  R  Q  P
     61 TCCTGTGCAACTTCTGGGTTCACCTTCACTGATTACTACATGAGCTGGGTCCGCCAGCCT

VH CDR2(SEQ ID NO: 20)
     41 P  G  K  A  L  E  W  L  G  F  I  R  N  K  A  N  G  Y  T  K
    121 CCAGGAAAGGCACTTGAGTGGTTGGGTTTTATTAGAAACAAAGCTAATGGTTACACAAAA

61 E  Y  S  A  S  V  K  G  R  F  T  I  S  R  D  N  S  Q  S  I
    181 GAGTACAGTGCATCTGTGAAGGGTCGGTTCACCATCTCCAGAGATAATTCCCAAAGCATC

81 L  Y  L  Q  M  N  T  L  G  A  E  D  S  A  T  Y  Y  C  A  R
    241 CTCTATCTTCAAATGAACACACTGGGAGCTGAGGACAGTGCCACTTATTACTGTGCACGT

VH CDR3 (SEQ ID NO: 21)
    101 D  Y  D  D  D  Y  W  G  Q  G  T  T  L  T  V  S  S (SEQ ID NO: 92)
    301 GACTACGACGACGACTACTGGGGCCAAGGCACCACTCTCACAGTCTCCTCA (SEQ ID NO: 91)
```

FIG. 15

Anti-CXCR4 VK, clone AA36

GATATTAAGATGACCCAGTCTCCATCCTCCCTGGCTGTGTCAACAGGAGAGAAGGTCACTATGCGCTGCAAATCCAG
TCAGAGTCTGTTCAACAGTAGAACCCGAAAGAACTACTTGGCTTGGTACCAGCAGAAGCCAGGGCAGTCTCCTAAAC
TGCTGATCTACTGGGCATCCACTAGGGAATCTGGGGTCCCTGATCGCTTCACAGGCAGTGGATCTGGGACAGATTTC
ACTCTCACCATCAGCAGTGTGCAGGCTGAAGACCTGGCAGTTTATTACTGCAAGCAATCTTATTATCTTCGGACGTT
CGGTGGAGGCACCAAGCTGGAAATCAAAC (SEQ ID NO: 93)

Translate

```
  1 D  I  K  M  T  Q  S  P  S  S  L  A  V  S  T  G  E  K  V  T
  1 GATATTAAGATGACCCAGTCTCCATCCTCCCTGGCTGTGTCAACAGGAGAGAAGGTCACT

VK CDR1(SEQ ID NO: 22)
 21 M  R  C  K  S  S  Q  S  L  F  N  S  R  T  R  K  N  Y  L  A
 61 ATGCGCTGCAAATCCAGTCAGAGTCTGTTCAACAGTAGAACCCGAAAGAACTACTTGGCT

VK CDR2(SEQ ID NO: 23)
 41 W  Y  Q  Q  K  P  G  Q  S  P  K  L  L  I  Y  W  A  S  T  R
121 TGGTACCAGCAGAAGCCAGGGCAGTCTCCTAAACTGCTGATCTACTGGGCATCCACTAGG

61 E  S  G  V  P  D  R  F  T  G  S  G  S  G  T  D  F  T  L  T
181 GAATCTGGGGTCCCTGATCGCTTCACAGGCAGTGGATCTGGGACAGATTTCACTCTCACC

VK CDR3(SEQ ID NO: 24)
 81 I  S  S  V  Q  A  E  D  L  A  V  Y  Y  C  K  Q  S  Y  Y  L
241 ATCAGCAGTGTGCAGGCTGAAGACCTGGCAGTTTATTACTGCAAGCAATCTTATTATCTT

101 R  T  F  G  G  G  T  K  L  E  I  K  (SEQ ID NO: 94)
301 CGGACGTTCGGTGGAGGCACCAAGCTGGAAATCAAAC  (SEQ ID NO: 93)
```

FIG. 16

Anti-CXCR4 VH, clone X197

GAGGTGAAGCTGGTGGAGTCTGGAGGAGACTTGGTACAGCCTGGGACTTCTCTGAGACTCTCCTGTGCAACTTCTGG
GTTCACCTTCACTGATTACTACATGAGCTGGGTCCGCCAGCCTCCAGGAAAGGCACTTGAGTGGTTGGGTTTTATTA
GAAACAAAGCTAATGGTTACACAACAGAGTACAGTGCATCTGTGAAGGGTCGGTTCACCATCTCCAGGGATAATTCC
CAAAGCATCCTCTATCTTCAAATGAACACTCTGAGAGCTGAGGACAGTGCCACTTATTACTGTGCAAGAGATCTGGG
TGATGACTACTGGGGCCAAGGCACCACTCTCACAGTCTCCT (SEQ ID NO: 95)

Translate

```
        1 E   V   K   L   V   E   S   G   G   D   L   V   Q   P   G   T   S   L   R   L
        1 GAGGTGAAGCTGGTGGAGTCTGGAGGAGACTTGGTACAGCCTGGGACTTCTCTGAGACTC

VH CDR1(SEQ ID NO: 25)
       21 S   C   A   T   S   G   F   T   F   T   D   Y   Y   M   S   W   V   R   Q   P
       61 TCCTGTGCAACTTCTGGGTTCACCTTCACTGATTACTACATGAGCTGGGTCCGCCAGCCT

VH CDR2(SEQ ID NO: 26)
       41 P   G   K   A   L   E   W   L   G   F   I   R   N   K   A   N   G   Y   T   T
      121 CCAGGAAAGGCACTTGAGTGGTTGGGTTTTATTAGAAACAAAGCTAATGGTTACACAACA

61 E   Y   S   A   S   V   K   G   R   F   T   I   S   R   D   N   S   Q   S   I
      181 GAGTACAGTGCATCTGTGAAGGGTCGGTTCACCATCTCCAGGGATAATTCCCAAAGCATC

81 L   Y   L   Q   M   N   T   L   R   A   E   D   S   A   T   Y   Y   C   A   R
      241 CTCTATCTTCAAATGAACACTCTGAGAGCTGAGGACAGTGCCACTTATTACTGTGCAAGA

VH CDR3(SEQ ID NO: 27)
      101 D   L   G   D   D   Y   W   G   Q   G   T   T   L   T   V   S (SEQ ID NO: 96)
      301 GATCTGGGTGATGACTACTGGGGCCAAGGCACCACTCTCACAGTCTCCT (SEQ ID NO: 95)
```

FIG. 17

Anti-CXCR4 VK, clone X197

GACATTCAGATGATGCAGTCTCCATCCTCCCTGGCTGTGTCAGCTGGAGAGAAGGTCACTATGAGCTGCAAATCCAG
TCAGAGTCTGTTCAACAGTAGAACCCGAAAGAACTACTTGGCTTGGTACCAGCAGAAACCAGGGCAGTCTCCTAAAC
TGCTGATCTACTGGGCATCCAAAAGGGAATCTGGGGTCCCTGCTCGCTTCACAGGCAGTGGATCTGGGACAGATTTC
ACTCTCACCATCAGCAGTGTGCAGGCTGAAGACCTGGCAGTTTATTACTGCAAGCAATCTTATTATCTTAGGGCGTT
CGGTGGAGGCACCAAGCTGGAAATAAAAC (SEQ ID NO: 97)

Translate

```
  1 D   I   Q   M   M   Q   S   P   S   S   L   A   V   S   A   G   E   K   V   T
  1 GACATTCAGATGATGCAGTCTCCATCCTCCCTGGCTGTGTCAGCTGGAGAGAAGGTCACT

VK CDR1(SEQ ID NO: 28)
 21 M   S   C   K   S   S   Q   S   L   F   N   S   R   T   R   K   N   Y   L   A
 61 ATGAGCTGCAAATCCAGTCAGAGTCTGTTCAACAGTAGAACCCGAAAGAACTACTTGGCT

VK CDR2(SEQ ID NO: 29)
 41 W   Y   Q   Q   K   P   G   Q   S   P   K   L   L   I   Y   W   A   S   K   R
121 TGGTACCAGCAGAAACCAGGGCAGTCTCCTAAACTGCTGATCTACTGGGCATCCAAAAGG

61 E   S   G   V   P   A   R   F   T   G   S   G   S   G   T   D   F   T   L   T
181 GAATCTGGGGTCCCTGCTCGCTTCACAGGCAGTGGATCTGGGACAGATTTCACTCTCACC

VK CDR3(SEQ ID NO: 30)
 81 I   S   S   V   Q   A   E   D   L   A   V   Y   Y   C   K   Q   S   Y   Y   L
241 ATCAGCAGTGTGCAGGCTGAAGACCTGGCAGTTTATTACTGCAAGCAATCTTATTATCTT

101 R   A   F   G   G   G   T   K   L   E   I   K   (SEQ ID NO: 98)
301 AGGGCGTTCGGTGGAGGCACCAAGCTGGAAATAAAAC (SEQ ID NO: 97)
```

FIG. 18

Anti-CXCR4 VH, clone AA80

GAGGTGCAACTGGTGGAGTCTGGGGGAGGCTTAGTGAAGCCTGGAGGGTCCCTGAAACTCTCCTGTGCAGCCTCTGG
ATTCGCTTTCAGTAGCTATGACATGTCTTGGGTTCGCCAGACTCCGGAAAAGAGGCTGGAATGGGTCGCAACCATTA
GTAGTGGTGGTAGTTACACCTACTATCCAGACAGTGTGAAGGGCCGATTCACCATCTCCAGAGACAATGCCAGGAAC
ACCCTATACCTACAAATGAGCAGTCTGAGGTCTGAGGACACGGCCTTGTATTACTGTGCAAGACATCGGGATAAACC
CCTTGACTACTGGGGCCAAGGCACCACTCTCACAGTCTCCTCA (SEQ ID NO: 99)

Translate

```
        1  E  V  Q  L  V  E  S  G  G  G  L  V  K  P  G  G  S  L  K  L
        1  GAGGTGCAACTGGTGGAGTCTGGGGGAGGCTTAGTGAAGCCTGGAGGGTCCCTGAAACTC

VH CDR1(SEQ ID NO: 31)
       21  S  C  A  A  S  G  F  A  F  S  S  Y  D  M  S  W  V  R  Q  T
       61  TCCTGTGCAGCCTCTGGATTCGCTTTCAGTAGCTATGACATGTCTTGGGTTCGCCAGACT

VH CDR2(SEQ ID NO: 32)
       41  P  E  K  R  L  E  W  V  A  T  I  S  S  G  G  S  Y  T  Y  Y
      121  CCGGAAAAGAGGCTGGAATGGGTCGCAACCATTAGTAGTGGTGGTAGTTACACCTACTAT

61  P  D  S  V  K  G  R  F  T  I  S  R  D  N  A  R  N  T  L  Y
      181  CCAGACAGTGTGAAGGGCCGATTCACCATCTCCAGAGACAATGCCAGGAACACCCTATAC

81  L  Q  M  S  S  L  R  S  E  D  T  A  L  Y  Y  C  A  R  H  R
      241  CTACAAATGAGCAGTCTGAGGTCTGAGGACACGGCCTTGTATTACTGTGCAAGACATCGG

VH CDR3(SEQ ID NO: 33)
      101  D  K  P  L  D  Y  W  G  Q  G  T  T  L  T  V  S  S  (SEQ ID NO: 100)
      301  GATAAACCCCTTGACTACTGGGGCCAAGGCACCACTCTCACAGTCTCCTCA (SEQ ID NO: 99)
```

FIG. 19

Anti-CXCR4 VK, clone AA80

GACATTGTGATGACCCAGTCTCCACTCTCCCTGCCTGTCAGTCTTGGAGATCAAGCCTCCATCTCTTGCAGATCTAG
TCAGAGCCTTGTACACAGTAATGGAAACACCTATTTAAATTGGTACCTGCAGAAGCCAGGCCAGTCTCCAAAACTCC
TGATCTACAAAGTTTCCAACCGATTTTCTGGGGTCCCAGACAGGTTCAGTGGCAGTGGATCAGGGACAGATTTCACA
CTCAAGATCAGCAGAGTGGAGGCTGAGGATCTGGGAGTTTATTTCTGCTCTCAAATTACACATGTTCCTTGGACGTT
CGGTGGAGGCACCAAGCTGGAAATAAAAC (SEQ ID NO: 101)

Translate

```
  1 D  I  V  M  T  Q  S  P  L  S  L  P  V  S  L  G  D  Q  A  S
  1 GACATTGTGATGACCCAGTCTCCACTCTCCCTGCCTGTCAGTCTTGGAGATCAAGCCTCC

VK CDR1(SEQ ID NO: 34)
 21 I  S  C  R  S  S  Q  S  L  V  H  S  N  G  N  T  Y  L  N  W
 61 ATCTCTTGCAGATCTAGTCAGAGCCTTGTACACAGTAATGGAAACACCTATTTAAATTGG

VK CDR2(SEQ ID NO: 35)
 41 Y  L  Q  K  P  G  Q  S  P  K  L  L  I  Y  K  V  S  N  R  F
121 TACCTGCAGAAGCCAGGCCAGTCTCCAAAACTCCTGATCTACAAAGTTTCCAACCGATTT

61 S  G  V  P  D  R  F  S  G  S  G  S  G  T  D  F  T  L  K  I
181 TCTGGGGTCCCAGACAGGTTCAGTGGCAGTGGATCAGGGACAGATTTCACACTCAAGATC

VK CDR3(SEQ ID NO: 36)
 81 S  R  V  E  A  E  D  L  G  V  Y  F  C  S  Q  I  T  H  V  P
241 AGCAGAGTGGAGGCTGAGGATCTGGGAGTTTATTTCTGCTCTCAAATTACACATGTTCCT

101 W  T  F  G  G  G  T  K  L  E  I  K  (SEQ ID NO: 102)
301 TGGACGTTCGGTGGAGGCACCAAGCTGGAAATAAAAC (SEQ ID NO: 101)
```

FIG. 20

Anti-CXCR4 VH, clone AA101

GAAGTGAAGCTGGTGGAGTCTGGAGGAGGCTTGGTACAGCCTGGGGCTTCTCTGAGACTCTCCTGTGCAACTTCTGG
GTTCACCTTCACTGATTACTACATGACCTGGGTCCGCCAGCCTCCAGGAAAGGCACTTGAGTGGTTGGGTTTTATTA
GAAACAGAGCTAATGGTTACACAACAGAGTACAATGCATCTGTGAAGGGTCGGTTCACCATCTCCAGAGATAATTCC
CAAAACATCCTCTATCTTCAAATGAACACCCTGAGAACTGAGGACAGTGCCACTTATTACTGTGCCAGAGATCCCCT
GGGACGCTTTGACTACTGGGGCCGAGGCACCACTCTCACAGTCTCCTCA (SEQ ID NO: 103)

Translate
```
  1 E   V   K   L   V   E   S   G   G   G   L   V   Q   P   G   A   S   L   R   L
  1 GAAGTGAAGCTGGTGGAGTCTGGAGGAGGCTTGGTACAGCCTGGGGCTTCTCTGAGACTC VH CDR1(SEQ ID NO: 37)
 21 S   C   A   T   S   G   F   T   F   T   D   Y   Y   M   T   W   V   R   Q   P
 61 TCCTGTGCAACTTCTGGGTTCACCTTCACTGATTACTACATGACCTGGGTCCGCCAGCCT VH CDR2(SEQ ID NO: 38)
 41 P   G   K   A   L   E   W   L   G   F   I   R   N   R   A   N   G   Y   T   T
121 CCAGGAAAGGCACTTGAGTGGTTGGGTTTTATTAGAAACAGAGCTAATGGTTACACAACA 61 E   Y   N   A   S   V   K   G   R   F   T   I   S   R   D   N   S   Q   N   I
181 GAGTACAATGCATCTGTGAAGGGTCGGTTCACCATCTCCAGAGATAATTCCCAAAACATC 81 L   Y   L   Q   M   N   T   L   R   T   E   D   S   A   T   Y   Y   C   A   R
241 CTCTATCTTCAAATGAACACCCTGAGAACTGAGGACAGTGCCACTTATTACTGTGCCAGA VH CDR3(SEQ ID NO: 39)
101 D   P   L   G   R   F   D   Y   W   G   R   G   T   T   L   T   V   S   S (SEQ ID NO: 104)
301 GATCCCCTGGGACGCTTTGACTACTGGGGCCGAGGCACCACTCTCACAGTCTCCTCA (SEQ ID
NO: 103)
```

FIG. 21

Anti-CXCR4 VK, clone AA101

GATATTAAGATGACCCAGTCTCCATCCTCCCTGGCTGTGTCAGCAGGAGAGAAGGTCACTATGAGTTGCAAATCCAG
TCAGAGTCTGTTCAACAGTAGAACCCGAAAGAACTACTTGGCTTGGTACCAGCAGAAACCAGGGCAGTCTCCTAAAC
TGCTGATCTACTGGGCTTCTATTAGGGAATCTGGGGTCCCTGATCGCTTCACAGGCAGTGGATCTGGGACAGATTTC
ACTCTCACCATCAGCAGTGTGCAGGCTGAAGACCTGGCAGTTTATTACTGCACACAGTCTTCTTATCTTCGGACGTT
CGGTGGAGGCACCGAGCTGGAAATCAAAC (SEQ ID NO: 105)

Translate

```
   1 D  I  K  M  T  Q  S  P  S  S  L  A  V  S  A  G  E  K  V  T
   1 GATATTAAGATGACCCAGTCTCCATCCTCCCTGGCTGTGTCAGCAGGAGAGAAGGTCACT

VK CDR1 (SEQ ID NO: 40)
  21 M  S  C  K  S  S  Q  S  L  F  N  S  R  T  R  K  N  Y  L  A
  61 ATGAGTTGCAAATCCAGTCAGAGTCTGTTCAACAGTAGAACCCGAAAGAACTACTTGGCT

VK CDR2 (SEQ ID NO: 41)
  41 W  Y  Q  Q  K  P  G  Q  S  P  K  L  L  I  Y  W  A  S  I  R
 121 TGGTACCAGCAGAAACCAGGGCAGTCTCCTAAACTGCTGATCTACTGGGCTTCTATTAGG

61 E  S  G  V  P  D  R  F  T  G  S  G  S  G  T  D  F  T  L  T
 181 GAATCTGGGGTCCCTGATCGCTTCACAGGCAGTGGATCTGGGACAGATTTCACTCTCACC

VK CDR3 (SEQ ID NO: 42)
  81 I  S  S  V  Q  A  E  D  L  A  V  Y  Y  C  T  Q  S  S  Y  L
 241 ATCAGCAGTGTGCAGGCTGAAGACCTGGCAGTTTATTACTGCACACAGTCTTCTTATCTT

101 R  T  F  G  G  G  T  E  L  E  I  K (SEQ ID NO: 106)
 301 CGGACGTTCGGTGGAGGCACCGAGCTGGAAATCAAAC (SEQ ID NO: 105)
```

FIG. 22

Anti-CXCR4 VH, clone X39

GACGTGATGCTGGTGGAGTCTGGAGGAGGCTTGGTGCAACCTGGAGGATCCATGAAACTCTCCTGTATTGGCTCTGG
ATTCACTTTCAGTAACTACTGGATGAACTGGGTCCGCCAGTCTCCAGAGAAGGGGCTTGAGTGGGTTGCTGAAATTA
GATTGAAATCGAATAATTATGCAAAACATTATGCGGAGTCTGTGAAAGGGAGGTTCACCATCTCAAGAGATGATTCC
AAAAGTCGTGTCTACCTGCAAATGACCAACTTAAGAACTGAAGACACTGGCATTTATTACTGTACCATGCTGGGATA
CTACTGGGGCCAAGGCACCACTCTCACAGTCTCCTCA (SEQ ID NO: 107)

Translate

```
    1 D  V  M  L  V  E  S  G  G  G  L  V  Q  P  G  G  S  M  K  L
    1 GACGTGATGCTGGTGGAGTCTGGAGGAGGCTTGGTGCAACCTGGAGGATCCATGAAACTC

VH CDR1(SEQ ID NO: 43)
   21 S  C  I  G  S  G  F  T  F  S  N  Y  W  M  N  W  V  R  Q  S
   61 TCCTGTATTGGCTCTGGATTCACTTTCAGTAACTACTGGATGAACTGGGTCCGCCAGTCT

VH CDR2(SEQ ID NO: 44)
   41 P  E  K  G  L  E  W  V  A  E  I  R  L  K  S  N  N  Y  A  K
  121 CCAGAGAAGGGGCTTGAGTGGGTTGCTGAAATTAGATTGAAATCGAATAATTATGCAAAA

61 H  Y  A  E  S  V  K  G  R  F  T  I  S  R  D  D  S  K  S  R
  181 CATTATGCGGAGTCTGTGAAAGGGAGGTTCACCATCTCAAGAGATGATTCCAAAAGTCGT

81 V  Y  L  Q  M  T  N  L  R  T  E  D  T  G  I  Y  Y  C  T  M
  241 GTCTACCTGCAAATGACCAACTTAAGAACTGAAGACACTGGCATTTATTACTGTACCATG

VH CDR3(SEQ ID NO: 45)
  101 L  G  Y  Y  W  G  Q  G  T  T  L  T  V  S  S (SEQ ID NO: 108)
  301 CTGGGATACTACTGGGGCCAAGGCACCACTCTCACAGTCTCCTCA (SEQ ID NO: 107)
```

FIG. 23

Anti-CXCR4 VK, clone X39

GACATTTTGCTGACTCAGTCTCCTGCTTCCTTAGCTGTATCTCTGGGGCAGAGGGCCACCATCTCATGCAGGGCCAG
CCAAAGTGTCAGTTCATCTAGACAGAGTTATATGCACTGGTACCAACAGAAACCAGGACAGGCACCCAAACTCCTCA
TCAAGTATGCATCCAACCTAGAATCGGGGGTCCCTGCCAGGTTCAGTGGCAGTGGGTCTGGGACAGACTTCATCCTC
AACATCCATCCTGTGGAGGAGGAGGATACTGCAACATATTACTGTCAGCACAGTTGGGAGATTCCGTACACGTTCGG
AGGGGGGACCAAGCTGGAAATCAAACG (SEQ ID NO: 109)

Translate

```
  1 D   I   L   L   T   Q   S   P   A   S   L   A   V   S   L   G   Q   R   A   T
  1 GACATTTTGCTGACTCAGTCTCCTGCTTCCTTAGCTGTATCTCTGGGGCAGAGGGCCACC

VK CDR1(SEQ ID NO: 46)
 21 I   S   C   R   A   S   Q   S   V   S   S   S   R   Q   S   Y   M   H   W   Y
 61 ATCTCATGCAGGGCCAGCCAAAGTGTCAGTTCATCTAGACAGAGTTATATGCACTGGTAC

VK CDR2(SEQ ID NO: 47)
 41 Q   Q   K   P   G   Q   A   P   K   L   L   I   K   Y   A   S   N   L   E   S
121 CAACAGAAACCAGGACAGGCACCCAAACTCCTCATCAAGTATGCATCCAACCTAGAATCG

61 G   V   P   A   R   F   S   G   S   G   S   G   T   D   F   I   L   N   I   H
181 GGGGTCCCTGCCAGGTTCAGTGGCAGTGGGTCTGGGACAGACTTCATCCTCAACATCCAT

VK CDR3(SEQ ID NO: 48)
 81 P   V   E   E   E   D   T   A   T   Y   Y   C   Q   H   S   W   E   I   P   Y
241 CCTGTGGAGGAGGAGGATACTGCAACATATTACTGTCAGCACAGTTGGGAGATTCCGTAC

101 T   F   G   G   G   T   K   L   E   I   K   (SEQ ID NO: 110)
301 ACGTTCGGAGGGGGGACCAAGCTGGAAATCAAACG  (SEQ ID NO: 109)
```

FIG. 24

Anti-CXCR4 VH, clone X122

GAGGTGAAGCTGATGAAGTCTGGAGGAGGCTTGGTACAGCCTGGGGCTTCTCTGAGACTCTCCTGTGCAGCTTCTGG
GTTCACCTTCACTGATTACTACATGAGCTGGGTCCGCCAGCCTCCAGGAAAGGCACTTGAGTGGTTGGGTTTTATTA
GAAACAAAGCTAATGGTTACACAACAGACTACAGTGCATCTGTGAAGGGTCGGTTCACCATCTCCAGAGATAATTCC
CAAAGCATCCTCTATCTTCAAATGAACACACTGAGACCTGAGGACAGTGCCACTTATTACTGTGCAAGAGATGGAAC
TACGATGGGGGCTGCGGACTACTGGGGCCAAGGCACCACTCTCACAGTCTCCTCA (SEQ ID NO: 111)

Translate

```
    1 E   V   K   L   M   K   S   G   G   G   L   V   Q   P   G   A   S   L   R   L
    1 GAGGTGAAGCTGATGAAGTCTGGAGGAGGCTTGGTACAGCCTGGGGCTTCTCTGAGACTC

VH CDR1(SEQ ID NO: 49)
   21 S   C   A   A   S   G   F   T   F   T   D   Y   Y   M   S   W   V   R   Q   P
   61 TCCTGTGCAGCTTCTGGGTTCACCTTCACTGATTACTACATGAGCTGGGTCCGCCAGCCT

VH CDR2(SEQ ID NO: 50)
   41 P   G   K   A   L   E   W   L   G   F   I   R   N   K   A   N   G   Y   T   T
  121 CCAGGAAAGGCACTTGAGTGGTTGGGTTTTATTAGAAACAAAGCTAATGGTTACACAACA

61 D   Y   S   A   S   V   K   G   R   F   T   I   S   R   D   N   S   Q   S   I
  181 GACTACAGTGCATCTGTGAAGGGTCGGTTCACCATCTCCAGAGATAATTCCCAAAGCATC

81 L   Y   L   Q   M   N   T   L   R   P   E   D   S   A   T   Y   Y   C   A   R
  241 CTCTATCTTCAAATGAACACACTGAGACCTGAGGACAGTGCCACTTATTACTGTGCAAGA

VH CDR3(SEQ ID NO: 51)
  101 D   G   T   T   M   G   A   A   D   Y   W   G   Q   G   T   T   L   T   V   S
  301 GATGGAACTACGATGGGGGCTGCGGACTACTGGGGCCAAGGCACCACTCTCACAGTCTCC

121 S   (SEQ ID NO: 112)
  361 TCA (SEQ ID NO: 111)
```

FIG. 25

Anti-CXCR4 VK, clone X122

```
GACATTCAGATGACGCAGTCTCCATCCTCCCTGGCTGTGTCAGCAGGAGAGAAGGTCACTATGAGCTGCAAATCCAG
TCAGAGTCTGTTCAACAGTAGAACCCGAAAAAACTACTTGGCTTGGTACCAGCAGAAACCAGGGCAGTCTCCTAAAC
TGCTGATCTACTGGGCATTTCGTAGGGAATCTGGGGTCCCTGATCGCTTCACGGGCAGTGGATCTGGGACAGATTTC
AGTTTCACCATCAGAAGTGTGCAGGCTGAAGACCTGGCAGTTTATTACTGCAAACAATCTTATTATCTTCGGACGTT
CGGTGGAGGCACCAAGCTGGAGCTGAAAC (SEQ ID NO: 113)
```

Translate

```
    1  D  I  Q  M  T  Q  S  P  S  S  L  A  V  S  A  G  E  K  V  T
    1  GACATTCAGATGACGCAGTCTCCATCCTCCCTGGCTGTGTCAGCAGGAGAGAAGGTCACT

VK CDR1(SEQ ID NO: 52)
   21  M  S  C  K  S  S  Q  S  L  F  N  S  R  T  R  K  N  Y  L  A
   61  ATGAGCTGCAAATCCAGTCAGAGTCTGTTCAACAGTAGAACCCGAAAAAACTACTTGGCT

VK CDR2(SEQ ID NO: 53)
   41  W  Y  Q  Q  K  P  G  Q  S  P  K  L  L  I  Y  W  A  F  R  R
  121  TGGTACCAGCAGAAACCAGGGCAGTCTCCTAAACTGCTGATCTACTGGGCATTTCGTAGG

61  E  S  G  V  P  D  R  F  T  G  S  G  S  G  T  D  F  S  F  T
  181  GAATCTGGGGTCCCTGATCGCTTCACGGGCAGTGGATCTGGGACAGATTTCAGTTTCACC

VK CDR3(SEQ ID NO: 54)
   81  I  R  S  V  Q  A  E  D  L  A  V  Y  Y  C  K  Q  S  Y  Y  L
  241  ATCAGAAGTGTGCAGGCTGAAGACCTGGCAGTTTATTACTGCAAACAATCTTATTATCTT

101  R  T  F  G  G  G  T  K  L  E  L  K  (SEQ ID NO: 114)
  301  CGGACGTTCGGTGGAGGCACCAAGCTGGAGCTGAAAC (SEQ ID NO: 113)
```

FIG. 26

Anti-CXCR4 VH, clone X132

CAGGTCCAACTGCAGCAGTCTGGACCTGAGCTGGCGAGGCCTGGGGCTTCAGTGAAGCTGTCCTGCAAGGCCTCTGG
CTACACCTTCAGGAGCTATGGTATAAGCTGGGTGAAGCAGAGAACTGGACAGGGCCTTGAGTGGATTGGAGAGATTT
ATCCTAGAAGTGGTAATACTTACTACAATGAGAAGTTCAAGGGCAAGGCCACACTGACTGCAGACAAATCCTCCAAC
ACAGCGTACATGGAGCTCCGCAGCCTGACATCTGAGGACTCTGCGGTCTATTTCTGTGCAAGAGATAGTAAAGACTA
TGCTATGGACTATTGGGGTCAAGGAACCTCAGTCACCGTCTCCTCA (SEQ ID NO: 115)

Translate

```
  1 Q  V  Q  L  Q  Q  S  G  P  E  L  A  R  P  G  A  S  V  K  L
  1 CAGGTCCAACTGCAGCAGTCTGGACCTGAGCTGGCGAGGCCTGGGGCTTCAGTGAAGCTG

VH CDR1(SEQ ID NO: 55)
 21 S  C  K  A  S  G  Y  T  F  R  S  Y  G  I  S  W  V  K  Q  R
 61 TCCTGCAAGGCCTCTGGCTACACCTTCAGGAGCTATGGTATAAGCTGGGTGAAGCAGAGA

VH CDR2(SEQ ID NO: 56)
 41 T  G  Q  G  L  E  W  I  G  E  I  Y  P  R  S  G  N  T  Y  Y
121 ACTGGACAGGGCCTTGAGTGGATTGGAGAGATTTATCCTAGAAGTGGTAATACTTACTAC

61 N  E  K  F  K  G  K  A  T  L  T  A  D  K  S  S  N  T  A  Y
181 AATGAGAAGTTCAAGGGCAAGGCCACACTGACTGCAGACAAATCCTCCAACACAGCGTAC

81 M  E  L  R  S  L  T  S  E  D  S  A  V  Y  F  C  A  R  D  S
241 ATGGAGCTCCGCAGCCTGACATCTGAGGACTCTGCGGTCTATTTCTGTGCAAGAGATAGT

VH CDR3(SEQ ID NO: 57)
101 K  D  Y  A  M  D  Y  W  G  Q  G  T  S  V  T  V  S  S  (SEQ ID NO: 116)
301 AAAGACTATGCTATGGACTATTGGGGTCAAGGAACCTCAGTCACCGTCTCCTCA (SEQ ID NO: 115)
```

FIG. 27

Anti-CXCR4 VK, clone X132

GACGTTGTGATGACCCAGACTCCACTCACTTTGTCGGTTACCATTGGACAACCAGCCTCCATCTCTTGCAAGTCAAG
TCAGAGCCTCTTAGATAGTGATGGAAAGACATATTTGAATTGGTTGTTACAGAGGCCAGGCCAGTCTCCAAAGCGCC
TAATCTATCTGATGTCTAAACTGGACTCTGGAGTCCCTGACAGGTTCACTGGCAGTGGATCAGGGACAGATTTCACA
CTGAAAATCAGCAGAGTGGAGGCAGAGGATTTGGGAGTTTATTATTGCTGGCAAGGTACACATTTTCCTCACACGTT
CGGTGCTGGGACCAAGCTGGAAATAAAACG (SEQ ID NO: 117)

Translate

```
           1  D  V  V  M  T  Q  P  L  T  L  S  V  T  I  G  Q  P  A  S
           1  GACGTTGTGATGACCCAGACTCCACTCACTTTGTCGGTTACCATTGGACAACCAGCCTCC

VK CDR1(SEQ ID NO: 58)
          21  I  S  C  K  S  S  Q  S  L  L  D  S  D  G  K  T  Y  L  N  W
          61  ATCTCTTGCAAGTCAAGTCAGAGCCTCTTAGATAGTGATGGAAAGACATATTTGAATTGG

VK CDR2(SEQ ID NO: 59)
          41  L  L  Q  R  P  G  Q  S  P  K  R  L  I  Y  L  M  S  K  L  D
         121  TTGTTACAGAGGCCAGGCCAGTCTCCAAAGCGCCTAATCTATCTGATGTCTAAACTGGAC

61  S  G  V  P  D  R  F  T  G  S  G  S  G  T  D  F  T  L  K  I
         181  TCTGGAGTCCCTGACAGGTTCACTGGCAGTGGATCAGGGACAGATTTCACACTGAAAATC

VK CDR3(SEQ ID NO: 60)
          81  S  R  V  E  A  E  D  L  G  V  Y  Y  C  W  Q  G  T  H  F  P
         241  AGCAGAGTGGAGGCAGAGGATTTGGGAGTTTATTATTGCTGGCAAGGTACACATTTTCCT

101  H  T  F  G  A  G  T  K  L  E  I  K   (SEQ ID NO: 118)
         301  CACACGTTCGGTGCTGGGACCAAGCTGGAAATAAAACG (SEQ ID NO: 117)
```

FIG. 28

Anti-CXCR4 VH, clone X142

GAGGTGATGCTGGTGGAGTCTGGAGGAGGCTTGGTACAGCCTGGGGCTTCTCTGAGACTCTCCTGTGCAACTTCTGG
GTTCACCTTCACTGATTACTACATGAATTGGGTCCGCCAGCCTCCAGGAAAGGCACTTGAATGGTTGGGTTTTATTA
GAAACAAAGCTAATGGTTACACAACAGAGTACAGTGCATCTGTGAAGGGTCGGTTCACCATCTCCAGAGATAATTCC
CAAACCATCCTCTATCTTCAAATGAACACACTGAGAGCTGAGGACAGTGCCACTTATTACTGTGCAAGAGATGCGGG
ATCAGGGTCCCACTACTTTGACTACTGGGGCCAAGGCACCACTCTCACAGTCTCCTCA (SEQ ID NO: 119)

Translate

```
  1 E  V  M  L  V  E  S  G  G  L  V  Q  P  G  A  S  L  R  L
  1 GAGGTGATGCTGGTGGAGTCTGGAGGAGGCTTGGTACAGCCTGGGGCTTCTCTGAGACTC

VH CDR1(SEQ ID NO: 61)
 21 S  C  A  T  S  G  F  T  F  T  D  Y  Y  M  N  W  V  R  Q  P
 61 TCCTGTGCAACTTCTGGGTTCACCTTCACTGATTACTACATGAATTGGGTCCGCCAGCCT

VH CDR2(SEQ ID NO: 62)
 41 P  G  K  A  L  E  W  L  G  F  I  R  N  K  A  N  G  Y  T  T
121 CCAGGAAAGGCACTTGAATGGTTGGGTTTTATTAGAAACAAAGCTAATGGTTACACAACA

61 E  Y  S  A  S  V  K  G  R  F  T  I  S  R  D  N  S  Q  T  I
181 GAGTACAGTGCATCTGTGAAGGGTCGGTTCACCATCTCCAGAGATAATTCCCAAACCATC

81 L  Y  L  Q  M  N  T  L  R  A  E  D  S  A  T  Y  Y  C  A  R
241 CTCTATCTTCAAATGAACACACTGAGAGCTGAGGACAGTGCCACTTATTACTGTGCAAGA

VH CDR3(SEQ ID NO: 63)
101 D  A  G  S  G  S  H  Y  F  D  Y  W  G  Q  G  T  T  L  T  V
301 GATGCGGGATCAGGGTCCCACTACTTTGACTACTGGGGCCAAGGCACCACTCTCACAGTC

121 S  S     (SEQ ID NO: 120)
361 TCCTCA    (SEQ ID NO: 119)
```

FIG. 29

Anti-CXCR4 VK, clone X142

GACATTGTGCTGACACAGTCTCCATCCTCCCTGGCTGTGTCAGCAGGAGAGAAGGTCACTATGAGATGTAAATCCAG
TCAGAGTCTGTTCAACAGTAGAACCCGAAAGAACTACTTGGCTTGGTACCAGCAGAAACCAGGGCAGTCTCCTAAAC
TGCTGATCTATTGGGCATTAGCTAGGGAATCTGGGGTCCCTAAACGCTTCACAGGCAGTGGATCTGGGACAGATTTC
ACTCTCACCATCAGCAGTGTGCAGGCTGAAGACCTGGCAGTTTATTACTGCAAGCAATCTTATTATCTTCGGACGTT
CGGTGGAGGCACCAAGCTGGAAATCAAAC (SEQ ID NO: 121)

Translate

```
      1 D   I   V   L   T   Q   S   P   S   S   L   A   V   S   A   G   E   K   V   T
      1 GACATTGTGCTGACACAGTCTCCATCCTCCCTGGCTGTGTCAGCAGGAGAGAAGGTCACT

VK CDR1(SEQ ID NO: 64)
     21 M   R   C   K   S   S   Q   S   L   F   N   S   R   T   R   K   N   Y   L   A
     61 ATGAGATGTAAATCCAGTCAGAGTCTGTTCAACAGTAGAACCCGAAAGAACTACTTGGCT

VK CDR2(SEQ ID NO: 65)
     41 W   Y   Q   Q   K   P   G   Q   S   P   K   L   L   I   Y   W   A   L   A   R
    121 TGGTACCAGCAGAAACCAGGGCAGTCTCCTAAACTGCTGATCTATTGGGCATTAGCTAGG

61 E   S   G   V   P   K   R   F   T   G   S   G   S   G   T   D   F   T   L   T
    181 GAATCTGGGGTCCCTAAACGCTTCACAGGCAGTGGATCTGGGACAGATTTCACTCTCACC

VK CDR3(SEQ ID NO: 66)
     81 I   S   S   V   Q   A   E   D   L   A   V   Y   Y   C   K   Q   S   Y   Y   L
    241 ATCAGCAGTGTGCAGGCTGAAGACCTGGCAGTTTATTACTGCAAGCAATCTTATTATCTT

101 R   T   F   G   G   G   T   K   L   E   I   K   (SEQ ID NO: 122)
    301 CGGACGTTCGGTGGAGGCACCAAGCTGGAAATCAAAC (SEQ ID NO: 121)
```

FIG. 30

Anti-CXCR4 VH, clone X219

GAGGTGCAACTGGTGGAGTCTGGAGGAGGCTTGGTACAGCCTGGGGCTTCTCTGAGACTCTCCTGTGCAACTTCTGG
GTTCACCTTCACTGATTACTACATGAGCTGGGTCCGCCAGCCTCCAGGAAAGGCACTTGAGTGGTTGGGTTTTATTA
GAAACAAAGCTAATGGTTACACAACAGAGTACAGTGCATCTGTGAAGGGTCGGTTCACCATCTCCAGAGATAATTCC
CAAAGCATCCTCTATCTTCAAATGAACACACTGAGAGCTGCGGACAGTGCCACTTATTACTGTGCAAGAGGAACTGG
ACACTTTGACTACTGGGGCCAAGGCACCACTCTCACAGTCTCCTCA (SEQ ID NO: 123)

Translate

```
    1 E   V   Q   L   V   E   S   G   G   G   L   V   Q   P   G   A   S   L   R   L
    1 GAGGTGCAACTGGTGGAGTCTGGAGGAGGCTTGGTACAGCCTGGGGCTTCTCTGAGACTC

VH CDR1(SEQ ID NO: 67)
   21 S   C   A   T   S   G   F   T   F   T   D   Y   Y   M   S   W   V   R   Q   P
   61 TCCTGTGCAACTTCTGGGTTCACCTTCACTGATTACTACATGAGCTGGGTCCGCCAGCCT

VH CDR2(SEQ ID NO: 68)
   41 P   G   K   A   L   E   W   L   G   F   I   R   N   K   A   N   G   Y   T   T
  121 CCAGGAAAGGCACTTGAGTGGTTGGGTTTTATTAGAAACAAAGCTAATGGTTACACAACA

61 E   Y   S   A   S   V   K   G   R   F   T   I   S   R   D   N   S   Q   S   I
  181 GAGTACAGTGCATCTGTGAAGGGTCGGTTCACCATCTCCAGAGATAATTCCCAAAGCATC

81 L   Y   L   Q   M   N   T   L   R   A   A   D   S   A   T   Y   Y   C   A   R
  241 CTCTATCTTCAAATGAACACACTGAGAGCTGCGGACAGTGCCACTTATTACTGTGCAAGA

VH CDR3 (SEQ ID NO: 69)
  101 G   T   G   H   F   D   Y   W   G   Q   G   T   T   L   T   V   S   S  (SEQ ID NO: 124)
  301 GGAACTGGACACTTTGACTACTGGGGCCAAGGCACCACTCTCACAGTCTCCTCA (SEQ ID NO: 123)
```

FIG. 31

Anti-CXCR4 VK, clone X219

GATATTGTGATGACACAGTCTCCATCCTCCCTGGCTGTGTCAGCAGGAGAGAAGGTCACTATGAGCTGCAAATCCAG
TCAGAGTCTGTTCAACAGTAGAACCCGAAAGAACTACTTGGCTTGGTACCAGCAGAAACCAGGGCAGTCTCCTAAAC
TGCTGATCTACTGGGCATCCACTAGGGAATCTGGGGTGCCTGATCGCTTCACAGGCAGTGGATCTGGGACAGATTTC
ACTCTCACCATCAGCAGTGTGCAGGCTGAAGACCTGGCAGTTTATTACTGCAAGCAATCTTATTATCTTCGGACGTT
CGGAGGGGGGACCAAGCTGGAGCTGAAAC (SEQ ID NO: 125)

Translate

```
  1 D   I   V   M   T   Q   S   P   S   S   L   A   V   S   A   G   E   K   V   T
  1 GATATTGTGATGACACAGTCTCCATCCTCCCTGGCTGTGTCAGCAGGAGAGAAGGTCACT

VK CDR1 (SEQ ID NO: 70)
 21 M   S   C   K   S   S   Q   S   L   F   N   S   R   T   R   K   N   Y   L   A
 61 ATGAGCTGCAAATCCAGTCAGAGTCTGTTCAACAGTAGAACCCGAAAGAACTACTTGGCT

VK CDR2(SEQ ID NO: 71)
 41 W   Y   Q   Q   K   P   G   Q   S   P   K   L   L   I   Y   W   A   S   T   R
121 TGGTACCAGCAGAAACCAGGGCAGTCTCCTAAACTGCTGATCTACTGGGCATCCACTAGG

61 E   S   G   V   P   D   R   F   T   G   S   G   S   G   T   D   F   T   L   T
181 GAATCTGGGGTGCCTGATCGCTTCACAGGCAGTGGATCTGGGACAGATTTCACTCTCACC

VK CDR3(SEQ ID NO: 72)
 81 I   S   S   V   Q   A   E   D   L   A   V   Y   Y   C   K   Q   S   Y   Y   L
241 ATCAGCAGTGTGCAGGCTGAAGACCTGGCAGTTTATTACTGCAAGCAATCTTATTATCTT

101 R   T   F   G   G   G   T   K   L   E   L   K   (SEQ ID NO: 126)
301 CGGACGTTCGGAGGGGGGACCAAGCTGGAGCTGAAAC (SEQ ID NO: 125)
```

FIG. 32

Anti-CXCR4 VH, clone AA59

CAGGTCCAGCTGCAGCAGTCTGGACCTGAGCTGGTGAAGCCTGGGGCTTCAGTGAAGATGTCCTGTAAGGCTTCTGG
ATACACATTCACTGACTACCACATGAACTGGGTGAAGCAGAGCCATGGAAAGAGCCTTGAGTGGATTGGAAATATTA
ATCCTTACAACGGTGATATTAACTACAACCAGAAGTTCAAGGGCAAGGCCACATTGACTGTAGACAAATCCTCCAGA
ACAGCCTACATGCAGCTCAACAGCCTGACATCTGAGGACTCTGCAGTCTATTACTGTGCAAGAGGAGGGCAGCTCGG
GCTCGCCTACTGGGGCCAAGGCACCACTCTCACAGTCTCCTCA (SEQ ID NO: 127)

Translate

```
  1 Q  V  Q  L  Q  Q  S  G  P  E  L  V  K  P  G  A  S  V  K  M
  1 CAGGTCCAGCTGCAGCAGTCTGGACCTGAGCTGGTGAAGCCTGGGGCTTCAGTGAAGATG

VH CDR1(SEQ ID NO: 73)
 21 S  C  K  A  S  G  Y  T  F  T  D  Y  H  M  N  W  V  K  Q  S
 61 TCCTGTAAGGCTTCTGGATACACATTCACTGACTACCACATGAACTGGGTGAAGCAGAGC

VH CDR2(SEQ ID NO: 74)
 41 H  G  K  S  L  E  W  I  G  N  I  N  P  Y  N  G  D  I  N  Y
121 CATGGAAAGAGCCTTGAGTGGATTGGAAATATTAATCCTTACAACGGTGATATTAACTAC

61 N  Q  K  F  K  G  K  A  T  L  T  V  D  K  S  S  R  T  A  Y
181 AACCAGAAGTTCAAGGGCAAGGCCACATTGACTGTAGACAAATCCTCCAGAACAGCCTAC

81 M  Q  L  N  S  L  T  S  E  D  S  A  V  Y  Y  C  A  R  G  G
241 ATGCAGCTCAACAGCCTGACATCTGAGGACTCTGCAGTCTATTACTGTGCAAGAGGAGGG

VH CDR3(SEQ ID NO: 75)
101 Q  L  G  L  A  Y  W  G  Q  G  T  T  L  T  V  S  S  (SEQ ID NO: 128)
301 CAGCTCGGGCTCGCCTACTGGGGCCAAGGCACCACTCTCACAGTCTCCTCA (SEQ ID NO: 127)
```

FIG. 33

Anti-CXCR4 VK, clone AA59

GACATTCAGATGATGCAGTCTCCATCCTCCCTGACTGTGTCAGCAGGAGAGAAGGTCACTATGAGCTGCAAATCCAG
TCAGAGTCTGTTCAACAGTAGAACCCGAAAGAACTACTTGGCTTGGTACCAGCAGAAACCAGGGCAGTCTCCTAAAC
TGCTGATCTACTGGGCATTGATTAGGGAATCTGGGGTCCCTGATCGCTTCACAGGCAGTGGATCTGGGACAGATTTC
ACTCTCACCATCAGCCGTGTGCAGGCTGAGGACCTGGCAGTTTATTACTGCAAGCAATCTTATTATCTTCGGACGTT
CGGTGGAGGCACCAAGCTGGAAATCAAAC (SEQ ID NO: 129)

Translate

```
  1 D  I  Q  M  M  Q  S  P  S  S  L  T  V  S  A  G  E  K  V  T
  1 GACATTCAGATGATGCAGTCTCCATCCTCCCTGACTGTGTCAGCAGGAGAGAAGGTCACT

VK CDR1 (SEQ ID NO: 76)
 21 M  S  C  K  S  S  Q  S  L  F  N  S  R  T  R  K  N  Y  L  A
 61 ATGAGCTGCAAATCCAGTCAGAGTCTGTTCAACAGTAGAACCCGAAAGAACTACTTGGCT

VK CDR2(SEQ ID NO: 77)
 41 W  Y  Q  Q  K  P  G  Q  S  P  K  L  L  I  Y  W  A  L  I  R
121 TGGTACCAGCAGAAACCAGGGCAGTCTCCTAAACTGCTGATCTACTGGGCATTGATTAGG

61 E  S  G  V  P  D  R  F  T  G  S  G  S  G  T  D  F  T  L  T
181 GAATCTGGGGTCCCTGATCGCTTCACAGGCAGTGGATCTGGGACAGATTTCACTCTCACC

VK CDR3(SEQ ID NO: 78)
 81 I  S  R  V  Q  A  E  D  L  A  V  Y  Y  C  K  Q  S  Y  Y  L
241 ATCAGCCGTGTGCAGGCTGAGGACCTGGCAGTTTATTACTGCAAGCAATCTTATTATCTT

101 R  T  F  G  G  G  T  K  L  E  I  K  (SEQ ID NO: 130)
301 CGGACGTTCGGTGGAGGCACCAAGCTGGAAATCAAAC (SEQ ID NO: 129)
```

FIG. 34

Human CXCR4 (UNIPROT: P61073) Isoform 1

(SEQ ID NO: 131)  (Underlined sequences represent the extracellular regions)

MEGISIYTSDNYTEEMGSGDYDSMKEPCFREENANFNKIFLPTIYSIIFLTGIVGNGLVILVMGYQKKLRSMTDKYR
LHLSVADLLFVITLPFWAVDAVANWYFGNFLCKAVHVIYTVNLYSSVLILAFISLDRYLAIVHATNSQRPRKLLAEK
VVYVGVWIPALLLTIPDFIFANVSEADDRYICDRFYPNDLWVVVFQFQHIMVGLILPGIVILSCYCIIISKLSHSKG
HQKRKALKTTVILILAFFACWLPYYIGISIDSFILLEIIKQGCEFENTVHKWISITEALAFFHCCLNPILYAFLGAK
FKTSAQHALTSVSRGSSLKILSKGKRGGHSSVSTESESSSFHSS

ANTI-HUMAN CXCR4 ANTIBODIES AND METHODS OF MAKING SAME

This application claims priority of U.S. Provisional Patent Application No. 61/800,963 which is herein incorporated in its entirety.

The instant application contains a Sequence Listing which has been submitted electronically in ASCII format and is hereby incorporated by reference in its entirety. Said ASCII copy, created on Apr. 23, 2014, is named SDIX-0030_SL.txt and is 103,740 bytes in size.

BACKGROUND OF THE INVENTION

C-X-C chemokine receptor type 4 (CXCR4) is an alpha-chemokine receptor that binds the ligand SDF-1 and transmits intracellular signals through several different pathways resulting in an increase in calcium and/or a decrease in cAMP levels. The extracellular regions of CXCR4 are composed of 4 discontinuous segments (N-terminal domain, extracellular loop (ECL) 1, ECL2, and ECL3), comprising a total of 91 amino acids.

SUMMARY OF THE INVENTION

In one aspect, the present invention provides an antibody comprising: a first heavy chain CDR comprising SEQ ID NO:1; a second heavy chain CDR comprising SEQ ID NO:2; a third heavy chain CDR comprising SEQ ID NO:3; a first light chain CDR comprising SEQ ID NO:4; a second light chain CDR comprising SEQ ID NO:5; and a third light chain CDR comprising SEQ ID NO:6, wherein the antibody binds to human CXCR4.

In one aspect, the present invention provides an antibody comprising: a first heavy chain CDR comprising SEQ ID NO:7; a second heavy chain CDR comprising SEQ ID NO:8; a third heavy chain CDR comprising SEQ ID NO:9; a first light chain CDR comprising SEQ ID NO:10; a second light chain CDR comprising SEQ ID NO:11; and a third light chain CDR comprising SEQ ID NO:12, wherein said antibody binds to human CXCR4.

In one aspect, the present invention provides an antibody comprising: a first heavy chain CDR comprising SEQ ID NO:13; a second heavy chain CDR comprising SEQ ID NO:14; a third heavy chain CDR comprising SEQ ID NO:15; a first light chain CDR comprising SEQ ID NO:16; a second light chain CDR comprising SEQ ID NO:17; and a third light chain CDR comprising SEQ ID NO:18, wherein said antibody binds to human CXCR4.

In one aspect, the present invention provides an antibody comprising: a first heavy chain CDR comprising SEQ ID NO:19; a second heavy chain CDR comprising SEQ ID NO:20; a third heavy chain CDR comprising SEQ ID NO:21; a first light chain CDR comprising SEQ ID NO:22; a second light chain CDR comprising SEQ ID NO:23; and a third light chain CDR comprising SEQ ID NO:24, wherein said antibody binds to human CXCR4.

In one aspect, the present invention provides an antibody comprising: a first heavy chain CDR comprising SEQ ID NO:25; a second heavy chain CDR comprising SEQ ID NO:26; a third heavy chain CDR comprising SEQ ID NO:27; a first light chain CDR comprising SEQ ID NO:28; a second light chain CDR comprising SEQ ID NO:29; and a third light chain CDR comprising SEQ ID NO:30, wherein said antibody binds to human CXCR4.

In one aspect, the present invention provides an antibody comprising: a first heavy chain CDR comprising SEQ ID NO:31; a second heavy chain CDR comprising SEQ ID NO:32; a third heavy chain CDR comprising SEQ ID NO:33; a first light chain CDR comprising SEQ ID NO:34; a second light chain CDR comprising SEQ ID NO:35; and a third light chain CDR comprising SEQ ID NO:36, wherein said antibody binds to human CXCR4.

In one aspect, the present invention provides an antibody comprising: a first heavy chain CDR comprising SEQ ID NO:37; a second heavy chain CDR comprising SEQ ID NO:38; a third heavy chain CDR comprising SEQ ID NO:39; a first light chain CDR comprising SEQ ID NO:40; a second light chain CDR comprising SEQ ID NO:41; and a third light chain CDR comprising SEQ ID NO:42, wherein said antibody binds to human CXCR4.

In one aspect, the present invention provides an antibody comprising: a first heavy chain CDR comprising SEQ ID NO:43; a second heavy chain CDR comprising SEQ ID NO:44; a third heavy chain CDR comprising SEQ ID NO:45; a first light chain CDR comprising SEQ ID NO:46; a second light chain CDR comprising SEQ ID NO:47; and a third light chain CDR comprising SEQ ID NO:48, wherein said antibody binds to human CXCR4.

In one aspect, the present invention provides an antibody comprising: a first heavy chain CDR comprising SEQ ID NO:49; a second heavy chain CDR comprising SEQ ID NO:50; a third heavy chain CDR comprising SEQ ID NO:51; a first light chain CDR comprising SEQ ID NO:52; a second light chain CDR comprising SEQ ID NO:53; and a third light chain CDR comprising SEQ ID NO:54, wherein said antibody binds to human CXCR4.

In one aspect, the present invention provides an antibody comprising: a first heavy chain CDR comprising SEQ ID NO:55; a second heavy chain CDR comprising SEQ ID NO:56; a third heavy chain CDR comprising SEQ ID NO:57; a first light chain CDR comprising SEQ ID NO:58; a second light chain CDR comprising SEQ ID NO:59; and a third light chain CDR comprising SEQ ID NO:60, wherein said antibody binds to human CXCR4.

In one aspect, the present invention provides an antibody comprising: a first heavy chain CDR comprising SEQ ID NO:61; a second heavy chain CDR comprising SEQ ID NO:62; a third heavy chain CDR comprising SEQ ID NO:63; a first light chain CDR comprising SEQ ID NO:64; a second light chain CDR comprising SEQ ID NO:65; and a third light chain CDR comprising SEQ ID NO:66, wherein said antibody binds to human CXCR4.

In one aspect, the present invention provides an antibody comprising: a first heavy chain CDR comprising SEQ ID NO:67; a second heavy chain CDR comprising SEQ ID NO:68; a third heavy chain CDR comprising SEQ ID NO:69; a first light chain CDR comprising SEQ ID NO:70; a second light chain CDR comprising SEQ ID NO:71; and a third light chain CDR comprising SEQ ID NO:72, wherein said antibody binds to human CXCR4.

In one aspect, the present invention provides an antibody comprising: a first heavy chain CDR comprising SEQ ID NO:73; a second heavy chain CDR comprising SEQ ID NO:74; a third heavy chain CDR comprising SEQ ID NO:75; a first light chain CDR comprising SEQ ID NO:76; a second light chain CDR comprising SEQ ID NO:77; and a third light chain CDR comprising SEQ ID NO:78, wherein said antibody binds to human CXCR4.

BRIEF DESCRIPTION OF THE DRAWINGS

These and other objects, features and advantages of the disclosure will be apparent from a consideration of the following non-limiting detailed description considered in conjunction with the drawing figures, in which:

FIG. 1 discloses "GVNK" as SEQ ID NO: 137, "NEAQ" as SEQ ID NO: 139, "EIENT" as SEQ ID NO: 138, the "38aa" sequence as SEQ ID NO: 140, the "11aa" sequence as SEQ ID NO: 141, "QGDIS" as SEQ ID NO: 142, the "21aa" sequence beginning "ANV" as SEQ ID NO: 143 and the "21aa" sequence beginning "DSF" as SEQ ID NO: 144.

FIG. 2A-2C is a chart describing the epitope mapping of select CXCR4 antibodies disclosed herein. FIGS. 2A-2C disclose "GVNK," "NEAQ" and "EIENT" as SEQ ID NOS 137, 139 and 138, respectively.

FIG. 3 is a summary of flow cytometry across different cell types for compositions encompassed herein.

FIG. 6 is a chart illustrating the functional effects of the CXCR4 antibodies in CXCR4-mediated signaling.

FIG. 7A-7B is a chart illustrating the CDR sequences of the VH and VK genes from hybridomas encompassed herein. FIG. 7A discloses the "CDR1" sequences as SEQ ID NOS: 1, 7, 13, 19, 25, 31, 37, 43, 49, 55, 61, 67 and 73, respectively, in order of appearance, the "CDR2" sequences as SEQ ID NOS: 2, 8, 14, 20, 26, 32, 38, 44, 50, 56, 62, 68 and 74, respectively, in order of appearance, and the "CDR3" sequences as SEQ ID NOS: 3, 9, 15, 21, 27, 33, 39, 45, 51, 57, 63, 69 and 75, respectively, in order of appearance. FIG. 7B discloses the "CDR1" sequences as SEQ ID NOS: 4, 10, 16, 22, 28, 34, 40, 46, 52, 58, 64, 70 and 76, respectively, in order of appearance, the "CDR2" sequences as SEQ ID NOS: 5, 11, 17, 23, 29, 35, 41, 47, 53, 59, 65, 71 and 77, respectively, in order of appearance, and the "CDR3" sequences as SEQ ID NOS: 6, 12, 18, 24, 30, 36, 42, 48, 54, 60, 66, 72 and 78, respectively, in order of appearance.

FIGS. 8-33 provide sequences of variable heavy chain and variable light chains of antibodies of the invention.

FIG. 34 provides a sequence of a human CXCR4 protein.

DETAILED DESCRIPTION OF THE INVENTION

Figure 1:
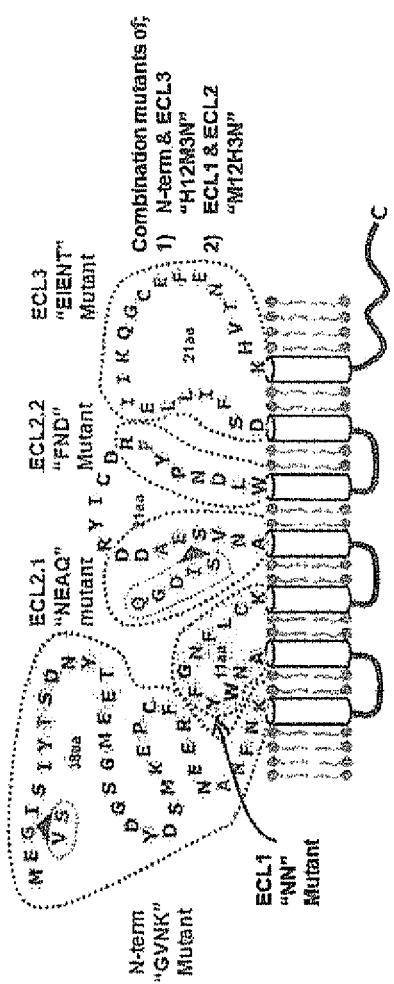
FIG. 1 is an image depicting design of CXCR4 mutants encompassed herein for epitope mapping.

With reference to the accompanying drawings, various embodiments of the present invention are described more fully below. Some but not all embodiments of the present invention are shown. Indeed, various embodiments of the invention may be embodied in many different forms and should not be construed as limited to the embodiments expressly described. Like numbers refer to like elements throughout. The singular forms "a," "an," and "the" include the singular and plural unless the context clearly dictates otherwise.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising) or alternatively including steps and compositions of no significance (consisting essentially of) or alternatively, intending only the stated method steps or compositions (consisting of).

I. Overview

The present invention is directed to novel antibodies to human CXCR4 with high affinity to the target and the ability to act potently as antagonists. The antibodies disclosed herein bind to a diverse range of epitopes.

II. Definitions

In order that the application may be more completely understood, several definitions are set forth below. Such definitions are meant to encompass grammatical equivalents.

By "ADCC" or "antibody dependent cell-mediated cytotoxicity" as used herein is meant the cell-mediated reaction wherein nonspecific cytotoxic cells that express FcγRs recognize bound antibody on a target cell and subsequently cause lysis of the target cell. ADCC is correlated with binding to FcγRIIIa; increased binding to FcγRIIIa leads to an increase in ADCC activity.

By "ADCP" or antibody dependent cell-mediated phagocytosis as used herein is meant the cell-mediated reaction wherein nonspecific cytotoxic cells that express FcγRs recognize bound antibody on a target cell and subsequently cause phagocytosis of the target cell.

By "modification" herein is meant an amino acid substitution, insertion, and/or deletion in a polypeptide sequence or an alteration to a moiety chemically linked to a protein. For example, a modification may be an altered carbohydrate or PEG structure attached to a protein. By "amino acid modification" herein is meant an amino acid substitution, insertion, and/or deletion in a polypeptide sequence. For clarity, unless otherwise noted, the amino acid modification is always to an amino acid coded for by DNA, e.g. the 20 amino acids that have codons in DNA and RNA.

By "amino acid substitution" or "substitution" herein is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution E272Y refers to a variant polypeptide, in which the glutamic acid at position 272 is replaced with tyrosine. For clarity, a protein which has been engineered to change the nucleic acid coding sequence but not change the starting amino acid (for example exchanging CGG (encoding arginine) to CGA (still encoding arginine) to increase host organism expression levels) is not an "amino acid substitution"; that is, despite the creation of a new gene encoding the same protein, if the protein has the same amino acid at the particular position that it started with, it is not an amino acid substitution.

By "amino acid insertion" or "insertion" as used herein is meant the addition of an amino acid sequence at a particular position in a parent polypeptide sequence. For example, -233E or 233E designates an insertion of glutamic acid after position 233 and before position 234. Additionally, -233ADE or A233ADE designates an insertion of AlaAspGlu after position 233 and before position 234.

By "amino acid deletion" or "deletion" as used herein is meant the removal of an amino acid sequence at a particular position in a parent polypeptide sequence. For example, E233- or E233# designates a deletion of glutamic acid at position 233. Additionally, EDA233- or EDA233# designates a deletion of the sequence GluAspAla that begins at position 233.

By "variant protein" or "protein variant", or "variant" as used herein is meant a protein that differs from that of a parent protein by virtue of at least one amino acid modification. Protein variant may refer to the protein itself, a composition comprising the protein, or the amino sequence that encodes it. Preferably, the protein variant has at least one amino acid modification compared to the parent protein, e.g. from about one to about seventy amino acid modifications, and preferably from about one to about five amino acid modifications compared to the parent. As described below, in some embodiments the parent polypeptide, for example an Fc parent polypeptide, is a human wild type sequence, such as the Fc region from IgG1, IgG2, IgG3 or IgG4, although human sequences with variants can also serve as "parent polypeptides". The protein variant sequence herein will preferably possess at least about 80% identity with a parent protein sequence, and most preferably at least about 90% identity, more preferably at least about 95-98-99% identity. Variant protein can refer to the variant protein itself, compositions comprising the protein variant, or the DNA sequence that encodes it. Accordingly, by "antibody variant" or "variant antibody" as used herein is meant an antibody that differs from a parent antibody by virtue of at least one amino acid modification, "IgG variant" or "variant IgG" as used herein is meant an antibody that differs from a parent IgG (again, in many cases, from a human IgG sequence) by virtue of at least one amino acid modification, and "immunoglobulin variant" or "variant immunoglobulin" as used herein is meant an immunoglobulin sequence that differs from that of a parent immunoglobulin sequence by virtue of at least one amino acid modification. "Fc variant" or "variant Fc" as used herein is meant a protein comprising an amino acid modification in an Fc domain. The Fc variants of the present invention are defined according to the amino acid modifications that compose them. Thus, for example, N434S or 434S is an Fc variant with the substitution serine at position 434 relative to the parent Fc polypeptide, wherein the numbering is according to the EU index. Likewise, M428L/N434S defines an Fc variant with the substitutions M428L and N434S relative to the parent Fc polypeptide. The identity of the WT amino acid may be unspecified, in which case the aforementioned variant is referred to as 428L/434S. It is noted that the order in which substitutions are provided is arbitrary, that is to say that, for example, 428L/434S is the same Fc variant as M428L/N434S, and so on. For all positions discussed in the present invention that relate to antibodies, unless otherwise noted, amino acid position numbering is according to the EU index. The EU index or EU index as in Kabat or EU numbering scheme refers to the numbering of the EU antibody (Edelman et al., 1969, Proc Natl Acad Sci USA 63:78-85, hereby entirely incorporated by reference.) The modification can be an addition, deletion, or substitution. Substitutions can include naturally occurring amino acids and, in some cases, synthetic amino acids. Examples include U.S. Pat. No. 6,586,207; WO 98/48032; WO 03/073238; US2004-0214988A1; WO 05/35727A2; WO 05/74524A2; J. W. Chin et al., (2002), Journal of the American Chemical Society 124:9026-9027; J. W. Chin, & P. G. Schultz, (2002), ChemBioChem 11:1135-1137; J. W. Chin, et al., (2002), PICAS United States of America 99:11020-11024; and, L. Wang, & P. G. Schultz, (2002), Chem. 1-10, all entirely incorporated by reference.

As used herein, "protein" herein is meant at least two covalently attached amino acids, which includes proteins, polypeptides, oligopeptides and peptides. The peptidyl group may comprise naturally occurring amino acids and peptide bonds, or synthetic peptidomimetic structures, i.e. "analogs", such as peptoids (see Simon et al., PNAS USA 89(20):9367 (1992), entirely incorporated by reference). The amino acids may either be naturally occurring or synthetic (e.g. not an amino acid that is coded for by DNA); as will be appreciated by those in the art. For example, homo-phenylalanine, citrulline, ornithine and norleucine are considered synthetic amino acids for the purposes of the invention, and both D- and L-(R or S) configured amino acids may be utilized. The variants of the present invention may comprise modifications that include the use of synthetic amino acids incorporated using, for example, the technologies developed by Schultz and colleagues, including but not limited to methods described by Cropp & Shultz, 2004, Trends Genet. 20(12):625-30, Anderson et al., 2004, Proc Natl Acad Sci USA 101 (2):7566-71, Zhang et al., 2003, 303(5656):371-3, and Chin et al., 2003, Science 301(5635):964-7, all entirely incorporated by reference. In addition, polypeptides may include synthetic derivatization of one or more side chains or termini, glycosylation, PEGylation, circular permutation, cyclization, linkers to other molecules, fusion to proteins or protein domains, and addition of peptide tags or labels.

By "residue" as used herein is meant a position in a protein and its associated amino acid identity. For example, Asparagine 297 (also referred to as Asn297 or N297) is a residue at position 297 in the human antibody IgG1.

By "Fab" or "Fab region" as used herein is meant the polypeptide that comprises the VH, CH1, VL, and CL immunoglobulin domains. Fab may refer to this region in isolation, or this region in the context of a full length antibody, antibody fragment or Fab fusion protein. By "Fv" or "Fv fragment" or "Fv region" as used herein is meant a polypeptide that comprises the VL and VH domains of a single antibody.

By "IgG subclass modification" or "isotype modification" as used herein is meant an amino acid modification that converts one amino acid of one IgG isotype to the corresponding amino acid in a different, aligned IgG isotype. For example, because IgG1 comprises a tyrosine and IgG2 a phenylalanine at EU position 296, a F296Y substitution in IgG2 is considered an IgG subclass modification.

By "non-naturally occurring modification" as used herein is meant an amino acid modification that is not isotypic. For example, because none of the IgGs comprise a serine at position 434, the substitution 434S in IgG1, IgG2, IgG3, or IgG4 (or hybrids thereof) is considered a non-naturally occurring modification.

By "amino acid" and "amino acid identity" as used herein is meant one of the 20 naturally occurring amino acids that are coded for by DNA and RNA.

By "effector function" as used herein is meant a biochemical event that results from the interaction of an antibody Fc region with an Fc receptor or ligand. Effector functions include but are not limited to ADCC, ADCP, and CDC.

By "IgG Fc ligand" as used herein is meant a molecule, preferably a polypeptide, from any organism that binds to the Fc region of an IgG antibody to form an Fc/Fc ligand complex. Fc ligands include but are not limited to FcγRIs, FcγRIIs, FcγRIIIs, FcRn, C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs (Davis et al., 2002, Immunological Reviews 190:123-136, entirely incorporated by reference). Fc ligands may include undiscovered molecules that bind Fc. Particular IgG Fc ligands are FcRn and Fc gamma receptors. By "Fc ligand" as used herein is meant a molecule, preferably a polypeptide, from any organism that binds to the Fc region of an antibody to form an Fc/Fc ligand complex.

By "parent polypeptide" as used herein is meant a starting polypeptide that is subsequently modified to generate a variant. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. Accordingly, by "parent immunoglobulin" as used herein is meant an unmodified immunoglobulin polypeptide that is modified to generate a variant, and by "parent antibody" as used herein is meant an unmodified antibody that is modified to generate a variant antibody. It should be noted that "parent antibody" includes known commercial, recombinantly produced antibodies as outlined below.

By "Fc fusion protein" or "immunoadhesin" herein is meant a protein comprising an Fc region, generally linked (optionally through a linker moiety, as described herein) to a different protein, such as a binding moiety to a target protein, as described herein).

By "position" as used herein is meant a location in the sequence of a protein. Positions may be numbered sequentially, or according to an established format, for example the EU index for antibody numbering.

By "target antigen" as used herein is meant the molecule that is bound specifically by the variable region of a given antibody. A target antigen may be a protein, carbohydrate, lipid, or other chemical compound. A wide number of suitable target antigens are described below.

By "target cell" as used herein is meant a cell that expresses a target antigen.

By "variable region" as used herein is meant the region of an immunoglobulin that comprises one or more Ig domains substantially encoded by any of the V.kappa., V.lamda., and/or VH genes that make up the kappa, lambda, and heavy chain immunoglobulin genetic loci respectively.

By "wild type or WT" herein is meant an amino acid sequence or a nucleotide sequence that is found in nature, including allelic variations. A WT protein has an amino acid sequence or a nucleotide sequence that has not been intentionally modified.

III. CXCR4 Antibodies

The present invention provides novel antibodies to human CXCR4. These antibodies show high affinity to the target and have the ability to act potently as antagonists. The antibodies disclosed herein bind to a diverse range of epitopes.

Antibodies that find use in the present invention can take on a number of formats as described herein, including traditional antibodies as well as antibody derivatives, fragments and mimetics, described below. In general, the term "antibody" includes any polypeptide that includes at least one constant domain, including, but not limited to, CH1, CH2, CH3 and CL.

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. The present invention is directed to the IgG class, which has several subclasses, including, but not limited to IgG1, IgG2, IgG3, and IgG4. Thus, "isotype" as used herein is meant any of the subclasses of immunoglobulins defined by the chemical and antigenic characteristics of their constant regions. It should be understood that therapeutic antibodies can also comprise hybrids of isotypes and/or subclasses.

The amino-terminal portion of each chain includes a variable region of about 100 to 110 or more amino acids primarily responsible for antigen recognition, generally referred to in the art and herein as the "Fv domain" or "Fv region". In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. "Variable" refers to the fact that certain segments of the variable region differ extensively in sequence among antibodies. Variability within the variable region is not evenly distributed. Instead, the V regions consist of relatively invariant stretches called framework regions (FRs) of 15-30 amino acids separated by shorter regions of extreme variability called "hypervariable regions" that are each 9-15 amino acids long or longer.

Each VH and VL is composed of three hypervariable regions ("complementary determining regions," "CDRs") and four FRs, arranged from amino-terminus to carboxy-terminus in the following order: FR1-CDR1-FR2-CDR2-FR3-CDR3-FR4.

The hypervariable region generally encompasses amino acid residues from about amino acid residues 24-34 (LCDR1; "L" denotes light chain), 50-56 (LCDR2) and 89-97 (LCDR3) in the light chain variable region and around about 31-35B (HCDR1; "H" denotes heavy chain), 50-65 (HCDR2), and 95-102 (HCDR3) in the heavy chain variable region; Kabat et al., SEQUENCES OF PROTEINS OF IMMUNOLOGICAL INTEREST, 5th Ed. Public Health Service, National Institutes of Health, Bethesda, Md. (1991) and/or those residues forming a hypervariable loop (e.g. residues 26-32 (LCDR1), 50-52 (LCDR2) and 91-96 (LCDR3) in the light chain variable region and 26-32 (HCDR1), 53-55 (HCDR2) and 96-101 (HCDR3) in the heavy chain variable region; Chothia and Lesk (1987) J. Mol. Biol. 196:901-917. Specific CDRs of the invention are described below.

Throughout the present specification, the Kabat numbering system is generally used when referring to a residue in the variable domain (approximately, residues 1-107 of the light chain variable region and residues 1-113 of the heavy chain variable region) (e.g, Kabat et al., supra (1991)).

The CDRs contribute to the formation of the antigen-binding, or more specifically, epitope binding site of antibodies. "Epitope" refers to a determinant that interacts with a specific antigen binding site in the variable region of an antibody molecule known as a paratope. Epitopes are groupings of molecules such as amino acids or sugar side chains and usually have specific structural characteristics, as well as specific charge characteristics. A single antigen may have more than one epitope.

The epitope may comprise amino acid residues directly involved in the binding (also called immunodominant component of the epitope) and other amino acid residues, which are not directly involved in the binding, such as amino acid residues which are effectively blocked by the specifically antigen binding peptide; in other words, the amino acid residue is within the footprint of the specifically antigen binding peptide.

Epitopes may be either conformational or linear. A conformational epitope is produced by spatially juxtaposed amino acids from different segments of the linear polypeptide chain. A linear epitope is one produced by adjacent amino acid residues in a polypeptide chain. Conformational and nonconformational epitopes may be distinguished in that the binding to the former but not the latter is lost in the presence of denaturing solvents.

An epitope typically includes at least 3, and more usually, at least 5 or 8-10 amino acids in a unique spatial conformation. Antibodies that recognize the same epitope can be verified in a simple immunoassay showing the ability of one antibody to block the binding of another antibody to a target antigen, for example "binning."

In some embodiments, the antibodies are full length. By "full length antibody" herein is meant the structure that constitutes the natural biological form of an antibody, including variable and constant regions, including one or more modifications as outlined herein.

Alternatively, the antibodies can be a variety of structures, including, but not limited to, antibody fragments, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and fragments of each, respectively.

Antibody Fragments

In one embodiment, the antibody is an antibody fragment. Of particular interest are antibodies that comprise Fc regions, Fc fusions, and the constant region of the heavy chain (CH1-hinge-CH2-CH3), again also including constant heavy region fusions.

Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, Nature 341:544-546, entirely incorporated by reference) which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, Science 242: 423-426, Huston et al., 1988, Proc. Natl. Acad. Sci. U.S.A. 85:5879-5883, entirely incorporated by reference), (viii) bispecific single chain Fv (WO 03/11161, hereby incorporated by reference) and (ix) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448, all entirely incorporated by reference). The antibody fragments may be modified. For example, the molecules may be stabilized by the incorporation of disulphide bridges linking the VH and VL domains (Reiter et al., 1996, Nature Biotech. 14:1239-1245, entirely incorporated by reference).

Chimeric and Humanized Antibodies

In some embodiments, the scaffold components can be a mixture from different species. As such, if the protein is an antibody, such antibody may be a chimeric antibody and/or a humanized antibody. In general, both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human. "Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321:522-525, Verhoeyen et al., 1988, Science 239: 1534-1536, all entirely incorporated by reference. "Backmutation" of selected acceptor framework residues to the corresponding donor residues is often required to regain affinity that is lost in the initial grafted construct (U.S. Pat. Nos. 5,530,101; 5,585,089; 5,693,761; 5,693,762; 6,180,370; 5,859,205; 5,821,337; 6,054,297; 6,407,213, all entirely incorporated by reference). The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system. Roque et al., 2004, Biotechnol. Prog. 20:639-654, entirely incorporated by reference. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein, all entirely incorporated by reference). Humanization methods include but are not limited to methods described in Jones et al., 1986, Nature 321:522-525; Riechmann et al., 1988; Nature 332:323-329; Verhoeyen et al., 1988, Science, 239: 1534-1536; Queen et al., 1989, Proc Natl Acad Sci, USA 86:10029-33; He et al., 1998, J. Immunol. 160: 1029-1035; Carter et al., 1992, Proc Natl Acad Sci USA 89:4285-9, Presta et al., 1997, Cancer Res. 57(20):4593-9; Gorman et al., 1991, Proc. Natl. Acad. Sci. USA 88:4181-4185; O'Connor et al., 1998, Protein Eng 11:321-8, all entirely incorporated by reference. Humanization or other methods of reducing the immunogenicity of nonhuman antibody variable regions may include resurfacing methods, as described for example in Roguska et al., 1994, Proc. Natl. Acad. Sci. USA 91:969-973, entirely incorporated by reference. In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759, all entirely incorporated by reference. Other humanization methods may involve the grafting of only parts of the CDRs, including but not limited to methods described in U.S. Ser. No. 09/810,510; Tan et al., 2002, J. Immunol. 169:1119-1125; De Pascalis et al., 2002, J. Immunol. 169:3076-3084, all entirely incorporated by reference.

In one embodiment, the antibody is a minibody. Minibodies are minimized antibody-like proteins comprising a scFv joined to a CH3 domain. Hu et al., 1996, Cancer Res. 56:3055-3061, entirely incorporated by reference. In some cases, the scFv can be joined to the Fc region, and may include some or the entire hinge region.

CXCR4 Antibodies and Variants

As used herein, the term "CXCR4 antibody" refers to any antibody that binds to CXCR4, including antibodies comprising any of the sequences described herein and variants thereof.

In certain aspects, CXCR4 antibodies of the invention include antibodies comprising CDR sequences as provided in FIG. 7. In further embodiments, CXCR4 antibodies of the invention comprise variants of the CDR sequences as provided in FIG. 7. In general, variants can include any number of modifications, as long as the function of the protein is still present, as described herein. That is, in the case of amino acid variants generated with the CDRs of any of the antibodies comprising sequences as provided in FIG. 7-33, for example, the antibody should still specifically bind to both human CXCR4. Similarly, if amino acid variants are generated with the Fc region, for example, the variant antibodies should maintain the required receptor binding functions for the particular application or indication of the antibody.

However, in general, from 1, 2, 3, 4, 5, 6, 7, 8, 9 or 10 amino acid substitutions are generally utilized as often the goal is to alter function with a minimal number of modifications. In some cases, there are from 1 to 5 modifications, with from 1-2, 1-3 and 1-4 also finding use in many embodiments.

In some embodiments, one or more amino acid modifications are made in one or more of the CDRs of the CXCR4 antibodies of the invention as provided in FIGS. 7-33. In general, only 1 or 2 or 3-amino acids are substituted in any single CDR, and generally no more than from 4, 5, 6, 7, 8 9 or 10 changes are made within a set of CDRs. However, it should be appreciated that any combination of no substitutions, 1, 2 or 3 substitutions in any CDR for a particular antibody can be independently and optionally combined with any other substitution.

In some cases, amino acid modifications in the CDRs are referred to as "affinity maturation". An "affinity matured" antibody is one having one or more alteration(s) in one or more CDRs which results in an improvement in the affinity of the antibody for antigen, compared to a parent antibody which does not possess those alteration(s). In some cases, although rare, it may be desirable to decrease the affinity of an antibody to its antigen, but this is generally not preferred.

Affinity maturation can be done to increase the binding affinity of the antibody for the antigen by at least about 10% to 50-100-150% or more, or from 1 to 5 fold as compared to the "parent" antibody. Preferred affinity matured antibodies will have nanomolar or even picomolar affinities for the target antigen. Affinity matured antibodies are produced by known procedures. See, for example, Marks et al., 1992, Biotechnology 10:779-783 that describes affinity maturation by variable heavy chain (VH) and variable light chain (VL) domain shuffling. Random mutagenesis of CDR and/or framework residues is described in: Barbas, et al. 1994, Proc. Nat. Acad. Sci, USA 91:3809-3813; Shier et al., 1995, Gene 169:147-155; Yelton et al., 1995, J. Immunol. 155:1994-2004; Jackson et al., 1995, J. Immunol. 154(7):3310-9; and Hawkins et al, 1992, J. Mol. Biol. 226:889-896, for example.

Alternatively, amino acid modifications can be made in one or more of the CDRs of the antibodies of the invention that are "silent", e.g. that do not significantly alter the affinity of the antibody for the antigen. These can be made for a number of reasons, including optimizing expression (as can be done for the nucleic acids encoding the antibodies of the invention).

Thus, included within the definition of the CDRs and antibodies of the invention are variant CDRs and antibodies; that is, the antibodies of the invention can include amino acid modifications in one or more of the CDRs of antibodies AA7.1, AA17.1, AA23.1, AA36.1, X197.1, AA80, AA101.1, X39.1, X122.1, X132.1, X142.1, X219.1, and AA59.1, for which sequences of the CDRs and the heavy and light chains are provided in FIGS. 7-33. In addition, amino acid modifications can also independently and optionally be made in any region outside the CDRs, including framework and constant regions.

In some embodiments, the anti-CXCR4 antibodies of the invention are composed of a variant Fc domain. As is known in the art, the Fc region of an antibody interacts with a number of Fc receptors and ligands, imparting an array of important functional capabilities referred to as effector functions. These Fc receptors include, but are not limited to, (in humans) FcγRI (CD64) including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158, correlated to antibody-dependent cell cytotoxicity (ADCC)) and FcγRIIIb (including allotypes FcγRIIIb-NA1 and FcγRIIIb-NA2), FcRn (the neonatal receptor), C1q (complement protein involved in complement dependent cytotoxicity (CDC)) and FcRn (the neonatal receptor involved in serum half-life). Suitable modifications can be made at one or more positions as is generally outlined, for example in US Pat. Nos. 2004/013210, 2005/0054832, 2006/0024298, 2006/0121032, 2006/0235208, 2007/0148170, 6,737,056, 7,670,600, 6,086,875, all of which are expressly incorporated by reference in their entirety, and in particular for specific amino acid substitutions that increase binding to Fc receptors.

all of which are expressly incorporated by reference in their entirety, and in particular for specific amino acid substitutions that increase binding to Fc receptors.

In further aspects, CXCR4 antibodies of the invention comprise any of the full length heavy or light chain sequences provided in FIGS. 8-33. In further embodiments, CXCR4 antibodies of the invention comprise sequences with a sequence identity of about 70%, 75%, 80%, 85%, 90%, 91%, 92%, 93%, 94%, 95%, 96%, 97%, 98%, 99% and 100% identity to any of the full length heavy or light chain sequences provided in FIGS. 8-33.

In some embodiments, CXCR4 antibodies comprise a heavy chain CDR2 with the following consensus sequence: IRN-X1-ANGYT-X2 (SEQ ID NO: 132), wherein X1 is either K or R and X2 is either K or T.

In some embodiments, CXCR4 antibodies comprise a light chain CDR1 with the following consensus sequence: QSL- X1-NSRTRKNY (SEQ ID NO: 133), where X1 is either F or L. In some embodiments, CXCR4 antibodies comprise a light chain CDR1 with the following consensus sequence: QSLVHSNGNT-X1 (SEQ ID NO: 134), where X1 is either F or Y.

In some embodiments, CXCR4 antibodies comprise a light chain CDR2 with the following consensus sequence: WA-X1, where X1 is S, L or F.

In some embodiments, CXCR4 antibodies comprise a light chain CDR3 with the following consensus sequence: X1-QS-X2-YLR-X3 (SEQ ID NO: 135), where X1 is either K or T, X2 is Y, S or N, and X3 is either T or A. In some embodiments, CXCR4 antibodies comprise a light chain CDR1 with the following consensus sequence: SQ-X1-THVPWT (SEQ ID NO: 136), where X1 is either S or I.

In further aspects, the present invention provides an expression vector encoding an antibody or protein according to any of the sequences described herein and in accordance with any of the sequences provided in FIGS. 7-33.

In still further aspects, the present invention provides a method of making an antibody or protein according to any of the sequences described herein and in accordance with any of the sequences provided in FIGS. 7-33, the method comprising providing a cell comprising a nucleic acid encoding that antibody or protein, where the cell is cultured under conditions suitable for expression of the antibody or protein.

In still further aspects, the present invention provides a method of treating a CXCR4-associated disease, the method comprising treating a subject in need thereof with an antibody or protein according to any of the sequences described herein and in accordance with any of the sequences provided in FIGS. 7-33.

In yet further aspects, the antibodies of the invention find use in a variety of applications, including diagnosis of CXCR4-related diseases and treatment thereof.

IV. Additional Modifications To CXCR4 Antibodies

In addition to any of the modifications and variants outlined above, other modifications can be made. For example, the molecules may be stabilized by the incorporation of disulphide bridges linking the VH and VL domains (Reiter et al., 1996, Nature Biotech. 14:1239-1245, entirely incorporated by reference for all purposes and in particular for all teachings regarding modifications of molecules, including antibodies). In addition, there are a variety of covalent modifications of antibodies that can be made as outlined below.

Covalent modifications of antibodies are included within the scope of this invention, and are generally, but not always, done post-translationally. For example, several types of covalent modifications of the antibody are introduced into the molecule by reacting specific amino acid residues of the antibody with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues may also be derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole and the like.

In addition, modifications at cysteines are particularly useful in antibody-drug conjugate (ADC) applications, further described below. In some embodiments, the constant region of the antibodies can be engineered to contain one or more cysteines that are particularly "thiol reactive", so as to allow more specific and controlled placement of the drug moiety. See for example U.S. Pat. No. 7,521,541, incorporated by reference in its entirety herein.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using 125I or 131I to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking antibodies to a water-insoluble support matrix or surface for use in a variety of methods, in addition to methods described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cynomolgusogen bromide-activated carbohydrates and the reactive substrates described in U.S. Pat. Nos. 3,969,287; 3,691,016; 4,195,128; 4,247,642; 4,229,537; and 4,330,440, all entirely incorporated by reference, are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W. H. Freeman & Co., San Francisco, pp. 79-86 [1983], entirely incorporated by reference), acetylation of the N-terminal amine, and amidation of any C-terminal carboxyl group.

In addition, as will be appreciated by those in the art, labels (including fluorescent, enzymatic, magnetic, radioactive, etc. can all be added to the antibodies (as well as the other compositions of the invention).

Glycosylation

Another type of covalent modification is alterations in glycosylation. In another embodiment, the antibodies disclosed herein can be modified to include one or more engineered glycoforms. By "engineered glycoform" as used herein is meant a carbohydrate composition that is covalently attached to the antibody, wherein said carbohydrate composition differs chemically from that of a parent antibody. Engineered glycoforms may be useful for a variety of purposes, including but not limited to enhancing or reducing effector function.

Engineered glycoforms may be generated by a variety of methods known in the art (Umaiia et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473; U.S. Pat. No. 6,602,684; U.S. Ser. No. 10/277,370; U.S. Ser. No. 10/113,929; PCT WO 00/61739A1; PCT WO 01/29246A1; PCT WO 02/31140A1; PCT WO 02/30954A1, all entirely incorporated by reference; (Potelligent® technology [Biowa, Inc., Princeton, N.J.]; GlycoMAb® glycosylation engineering technology [Glycart Biotechnology AG, Thrich, Switzerland]). Many of these techniques are based on controlling the level of fucosylated and/or bisecting oligosaccharides that are covalently attached to the Fc region, for example by expressing an IgG in various organisms or cell lines, engineered or otherwise (for example Lec-13 CHO cells or rat hybridoma YB2/0 cells, by regulating enzymes involved in the glycosylation pathway (for example FUT8 [α-1,6-fucosyltranserase] and/or β1-4-N-acetylglucosaminyltransferase III [GnTIII]), or by modifying carbohydrate(s) after the IgG has been expressed. For example, the "sugar engineered antibody" or "SEA technology" of Seattle Genetics functions by adding modified saccharides that inhibit fucosylation during production; see for example 20090317869, hereby incorporated by reference in its entirety. Engineered glycoform typically refers to the different carbohydrate or oligosaccharide; thus an antibody can include an engineered glycoform.

Alternatively, engineered glycoform may refer to the IgG variant that comprises the different carbohydrate or oligosaccharide. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antibody amino acid sequence is preferably altered through changes at the DNA level, particularly by mutating the DNA encoding the target polypeptide at preselected bases such that codons are generated that will translate into the desired amino acids.

Another means of increasing the number of carbohydrate moieties on the antibody is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 and in Aplin and Wriston, 1981, CRC Crit. Rev. Biochem., pp. 259-306, both entirely incorporated by reference.

Removal of carbohydrate moieties present on the starting antibody (e.g. post-translationally) may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, Arch. Biochem. Biophys. 259:52 and by Edge et al., 1981, Anal. Biochem. 118:131, both entirely incorporated by reference. Enzymatic cleavage of carbohydrate moieties on polypeptides can be achieved by the use of a variety of endo- and exo-glycosidases as described by Thotakura et al., 1987, Meth. Enzymol. 138:350, entirely incorporated by reference. Glycosylation at potential glycosylation sites may be prevented by the use of the compound tunicamycin as described by Duskin et al., 1982, J. Biol. Chem. 257:3105, entirely incorporated by reference. Tunicamycin blocks the formation of protein-N-glycoside linkages.

Another type of covalent modification of the antibody comprises linking the antibody to various nonproteinaceous polymers, including, but not limited to, various polyols such as polyethylene glycol, polypropylene glycol or polyoxyalkylenes, in the manner set forth in, for example, 2005-2006 PEG Catalog from Nektar Therapeutics (available at the Nektar website) U.S. Pat. Nos. 4,640,835; 4,496,689; 4,301,144; 4,670,417; 4,791,192 or 4,179,337, all entirely incorporated by reference. In addition, as is known in the art, amino acid substitutions may be made in various positions within the antibody to facilitate the addition of polymers such as PEG. See for example, U.S. Publication No. 2005/0114037A1, entirely incorporated by reference.

V. Experimental Examples

Development of Antibodies Against Human CXCR4

Mice were immunized and hybridomas were generated with two separate sets of animals (fusions 772X and 772AA).

The resulting hybridomas were screened by flow cytometry on CXCR4 expressing and control cells to identify those producing specific antibodies against CXCR4. This resulted in a total of 93 antibodies that reacted with the extracellular regions of human CXCR4.

The extracellular regions of CXCR4 are composed of 4 discontinuous segments (N-terminal domain, extracellular loop (ECL) 1, ECL2, ECL3, comprising a total of 91 amino acids. The critical amino acids within the epitope of each antibody were assessed on a panel of seven CXCR4 mutant proteins. Each mutant was designed by aligning the human CXCR4 sequence to the orthologous mouse CXCR4 sequence and selecting and substituting groups of amino acids to the orthologous mouse sequence, (the extracellular regions of human and mouse CXCR4 are 71% identical) (see FIG. 1.). In this way potential epitopes were disrupted while the possibility of creating gross structural changes was minimized to produce a properly folded protein. Evidence that the folding of the mutants were correct is supported by the fact that all of the mutants expressed at the surface of the cell at normal levels and at least one antibody bound to each of the mutants. The mutants are;

N-term GVNK (SEQ ID NO: 137): 8 amino acid changes in the N-terminal domain.

ECL1 NN: 2 amino acid changes in ECL1

ECL2.1 NEAQ (SEQ ID NO: 139): 8 amino acid changes in ECL2

ECL2.2 FND: 3 amino acid changes in ECL2

ECL3 EIENT (SEQ ID NO: 138): 5 amino acid changes in ECL3

H12M3N: combination of the GVNK (SEQ ID NO: 137) and EIENT (SEQ ID NO: 138) mutants (except the "GVNK" (SEQ ID NO: 137) mutations have 2 additional substitutions at M24 and E32) M12H3N: combination of the NN, NEAQ (SEQ ID NO: 139), and FND mutants The plasmids encoding each of the mutant CXCR4 genes were transiently transfected into HEK293 cells and allowed to express. Controls included a CXCR4 construct with wild type extracellular regions (positive control), and a plasmid with an unrelated membrane protein (human CD20, negative control). The supernatants from the initial hybridoma cultures were used to stain the transfected HEK293 cells, stained with a labeled goat anti-mouse antibody, and analyzed by flow cytometry. Control antibodies included the anti-CXCR4 antibodies from R&D systems (C171, C172, and C173), and 12G5. The staining of the cells was normalized to cells with wild type CXCR4 and reported as a percentage. In the select thirteen antibodies showed in FIG. 2, antibodies were mapped to either the N-terminus (N), ECL2 (Carnec et al. (2005) Journal of Virology v79 p 1930-1933), or to both the N-terminus and ECL2 (N2).

Figure 4A:
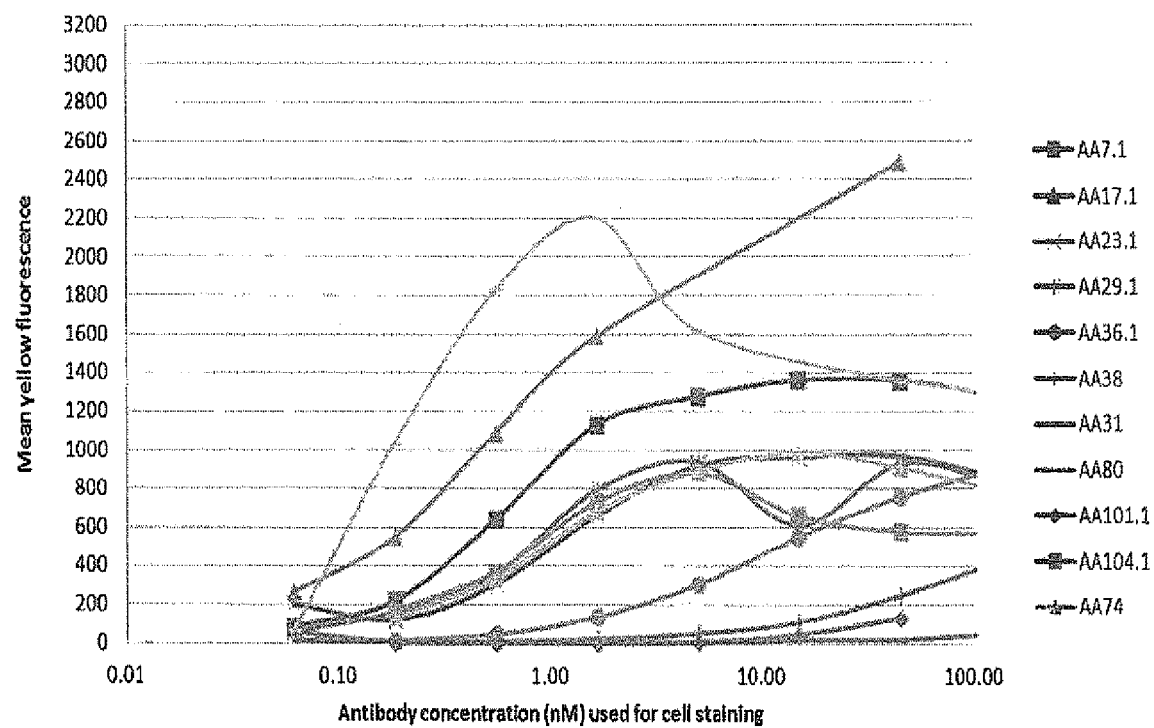
FIG. 4A-4C is a series of images depicting the flow cytometry titration curves for compositions in Jurkat cells.
Figure 4B:
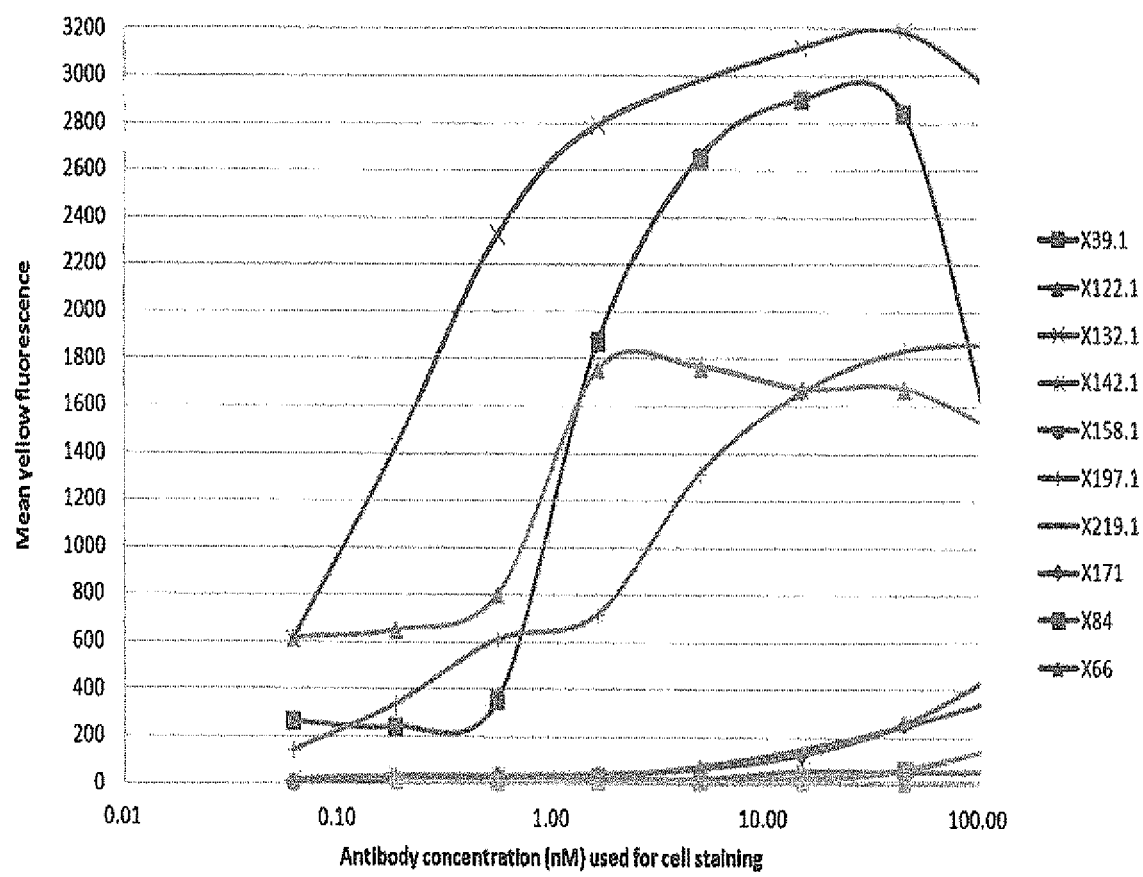
Figure 4C:
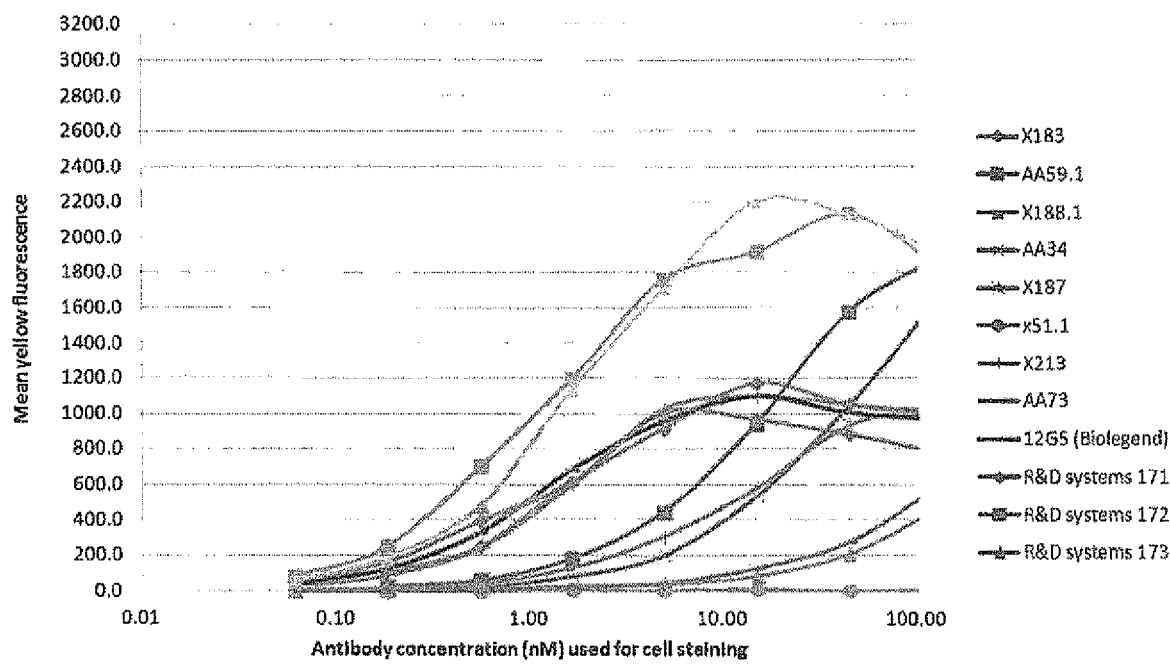
Figure 5A:
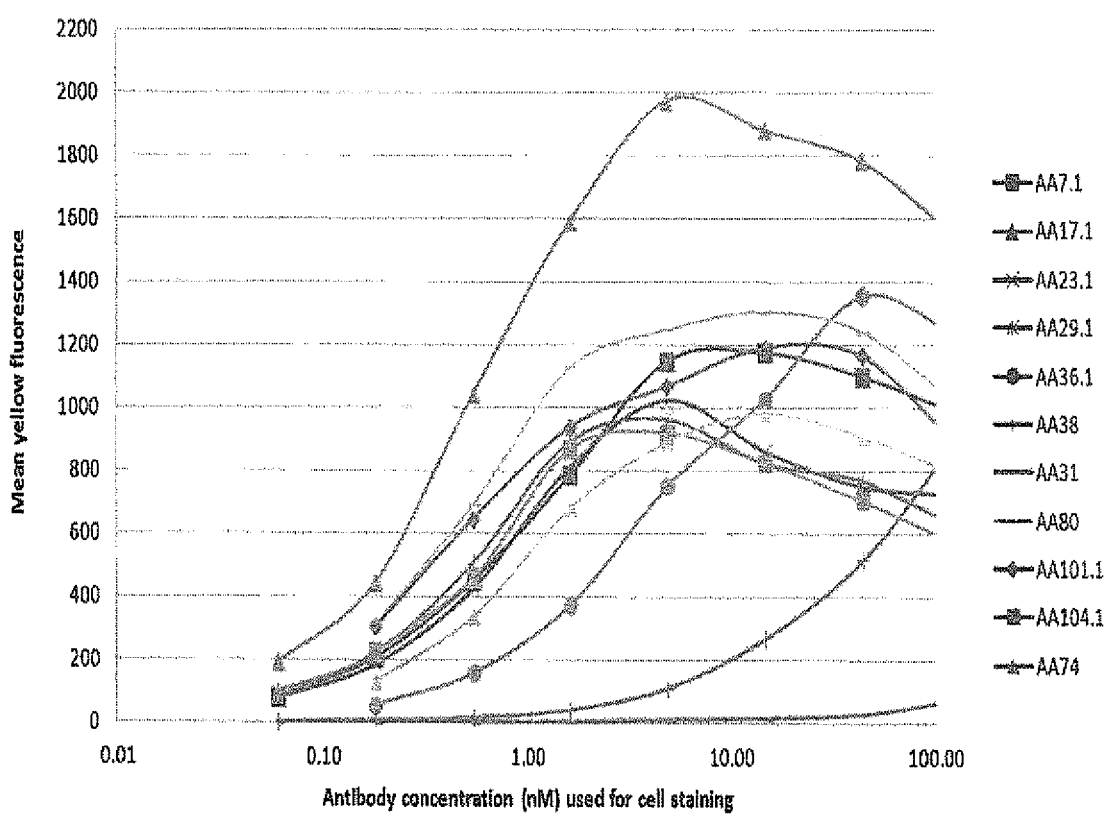
FIG. 5A-5C is a series of images depicting the flow cytometry titration curves for compositions in HEK293 cells.
Figure 5B:
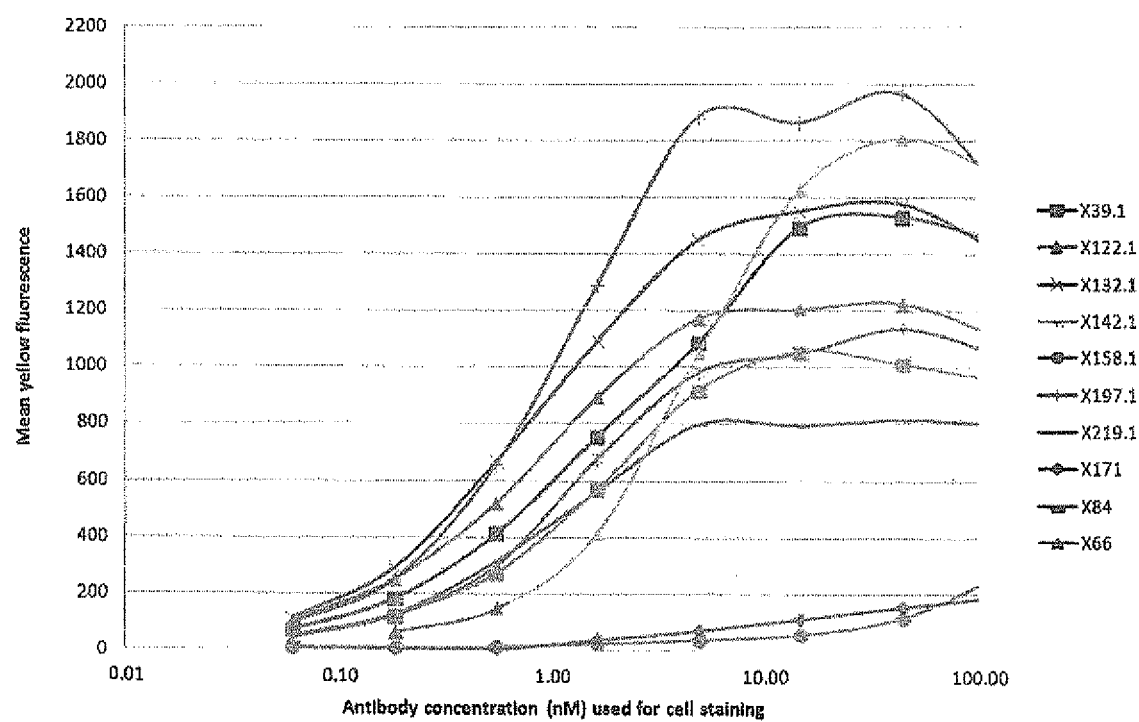
Figure 5C:
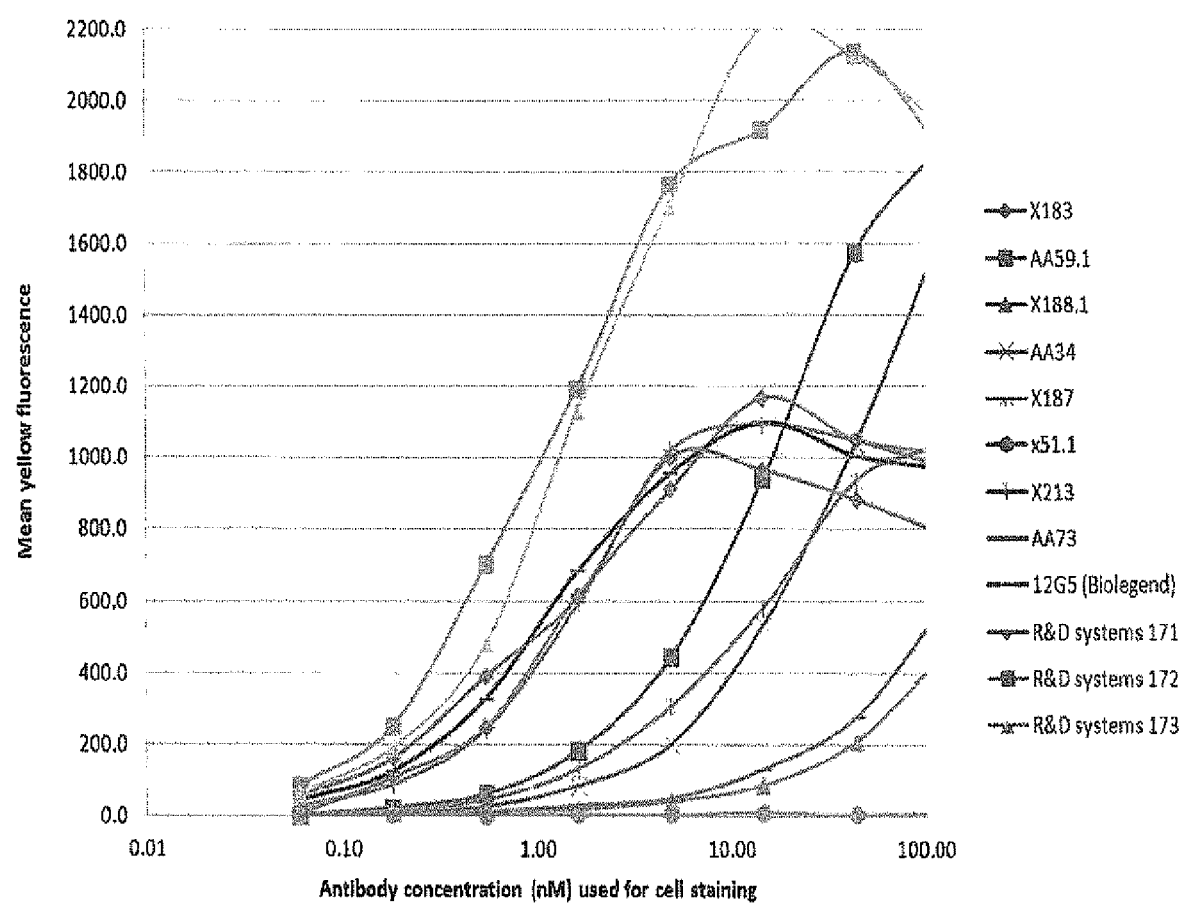

A select panel of the hybridomas was grown up to produce milligram quantities of antibody that was purified with protein A chromatography and dialyzed into PBS buffer. The antibodies were titrated on a panel different CXCR4 expressing cells lines, (Jurkat, transfected HEK293, Ramos, CEM), and analyzed by flow cytometry. It has previously been described that CXCR4 exists in multiple conformations and that the proportions of these vary in different cell types (Berchiche et al. (2007) The Journal of Biological Chemistry v282 p 5111-5115.; Carnec et al. (2005) Journal of Virology v79 p 1930-1933). The pattern of staining across the four cell types showed a wide range of variance suggesting that some of the antibodies are selectively recognizing different forms of CXCR4. For example, AA17, AA23, AA80, AA101, AA59, and X132 stained reasonably uniformly across different cell types, whereas AA7, AA36, X197, X39, X122, X142, and X219 exhibited significant differential staining across different cell types (FIGS. 3, 4, & 5 nd=not determined).

CXCR4 binds the ligand SDF-1 and transmits intracellular signals through several different pathways resulting in an increase in calcium and/or a decrease in cAMP levels (Rubin J. B. (2009) Semin Cancer Biol. V19 p 116-122). A select set of the CXCR4 antibodies were evaluated for their ability to block SDF-1 mediated signaling. SDF-1 is thought to act in a two step process where it first binds at the N-terminal region of CXCR4, a conformational change is triggered within CXCR4 resulting in SDF-1 docking with a region in ECL2 and ECL3 (Busillo J. M. & J. L. Benovic (2007) Biochim Biophys Acta. V1768 p 952-963). The CXCR4 antibodies were titrated in CXCR4 signaling assays either for detecting changes in intracellular calcium (Calcium flux) or cAMP levels (DiscoveRx). A summary of select antibodies is shown in FIG. 6 (nd=not determined, none=no significant antagonist activity detected).

Antibodies whose epitopes mapped to solely the N-terminal domain had no effect in the signaling assays. Whereas antibodies that mapped to ECL2 or N-terminus and ECL2 had the most potent effect.

The heavy and light chain antibody genes from the hybridomas were isolated by RT PCR, cloned, and sequenced. The PCR primers were designed to the beginning and end of the V domains of the heavy and light chains and therefore nucleotide changes in the determined sequence can occur within these regions due to cross priming. However, these are outside the functional CDR sites of the antibody genes that are responsible for binding to the antigen. The sequence was translated, the derivative germline VH and VK genes identified, and the CDR regions identified using the IMGT rules (Retter I et al. (2005) Nucleic Acids Res. v33(Database issue):D671-4) (FIG. 7). All of the 13 antibodies showed different sequences. One common theme was that all the antibodies that bound ECL2, with one exception (AA59), were derived from VH158 and VK046. Interestingly, two antibodies from different mice, AA36 and X197 exhibited highly similar CDR sequences (4 amino acid differences). This suggests that the ECL2 epitope provides a highly restrictive limitation on the antibodies resulting in selection of highly similar sequences.

Each and every reference herein is incorporated by reference in its entirety for all purposes and in particular for any teachings relevant to any of the embodiments discussed herein.

It will be appreciated by those skilled in the art that changes could be made to the exemplary embodiments described above without departing from the broad inventive concept thereof. It is understood, therefore, that this invention is not limited to the exemplary embodiments described, but it is intended to cover modifications within the spirit and scope of the present invention as defined by the claims. For example, specific features of the exemplary embodiments may or may not be part of the claimed invention and features of the disclosed embodiments may be combined.

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

What is claimed is:

1. An antibody that binds CXCR4 selected from the group consisting of:
   (a) an antibody comprising a first heavy chain CDR comprising SEQ ID NO: 1; a second heavy chain CDR comprising SEQ ID NO: 2; a third heavy chain CDR comprising SEQ ID NO: 3; a first light chain CDR comprising SEQ ID NO: 4; a second light chain CDR comprising SEQ ID NO: 5; and a third light chain CDR comprising SEQ ID NO: 6;
   (b) an antibody comprising: a first heavy chain CDR comprising SEQ ID NO: 7; a second heavy chain CDR comprising SEQ ID NO: 8; a third heavy chain CDR comprising SEQ ID NO: 9; a first light chain CDR comprising SEQ ID NO: 10; a second light chain CDR comprising SEQ ID NO: 11; and a third light chain CDR comprising SEQ ID NO: 12;
   (c) an antibody comprising: a first heavy chain CDR comprising SEQ ID NO: 13; a second heavy chain CDR comprising SEQ ID NO: 14; a third heavy chain CDR comprising SEQ ID NO: 15; a first light chain CDR comprising SEQ ID NO: 16; a second light chain CDR comprising SEQ ID NO: 17; and a third light chain CDR comprising SEQ ID NO: 18;
   (d) an antibody comprising: a first heavy chain CDR comprising SEQ ID NO: 19; a second heavy chain CDR comprising SEQ ID NO: 20; a third heavy chain CDR comprising SEQ ID NO: 21; a first light chain CDR comprising SEQ ID NO: 22; a second light chain CDR comprising SEQ ID NO: 23; and a third light chain CDR comprising SEQ ID NO: 24;
   (e) an antibody comprising: a first heavy chain CDR comprising SEQ ID NO: 25; a second heavy chain CDR comprising SEQ ID NO: 26; a third heavy chain CDR comprising SEQ ID NO: 27; a first light chain CDR comprising SEQ ID NO: 28; a second light chain CDR comprising SEQ ID NO: 29; and a third light chain CDR comprising SEQ ID NO: 30;
   (f) an antibody comprising: a first heavy chain CDR comprising SEQ ID NO: 31; a second heavy chain CDR comprising SEQ ID NO: 32; a third heavy chain CDR comprising SEQ ID NO: 33; a first light chain CDR comprising SEQ ID NO: 34; a second light chain CDR comprising SEQ ID NO: 35; and a third light chain CDR comprising SEQ ID NO: 36;
   (g) an antibody comprising: a first heavy chain CDR comprising SEQ ID NO: 37; a second heavy chain CDR comprising SEQ ID NO: 38; a third heavy chain CDR comprising SEQ ID NO: 39; a first light chain CDR comprising SEQ ID NO: 40; a second light chain CDR comprising SEQ ID NO: 41; and a third light chain CDR comprising SEQ ID NO: 42;
   (h) an antibody comprising: a first heavy chain CDR comprising SEQ ID NO: 43; a second heavy chain CDR comprising SEQ ID NO: 44; a third heavy chain CDR comprising SEQ ID NO: 45; a first light chain CDR comprising SEQ ID NO: 46; a second light chain CDR comprising SEQ ID NO: 47; and a third light chain CDR comprising SEQ ID NO: 48;
   (i) an antibody comprising: a first heavy chain CDR comprising SEQ ID NO: 49; a second heavy chain CDR comprising SEQ ID NO: 50; a third heavy chain CDR comprising SEQ ID NO: 51; a first light chain CDR comprising SEQ ID NO: 52; a second light chain CDR comprising SEQ ID NO: 53; and a third light chain CDR comprising SEQ ID NO: 54;
   (j) an antibody comprising: a first heavy chain CDR comprising SEQ ID NO: 55; a second heavy chain CDR comprising SEQ ID NO: 56; a third heavy chain CDR comprising SEQ ID NO: 57; a first light chain CDR comprising SEQ ID NO: 58; a second light chain CDR comprising SEQ ID NO: 59; and a third light chain CDR comprising SEQ ID NO: 60;
   (k) an antibody comprising: a first heavy chain CDR comprising SEQ ID NO: 61; a second heavy chain CDR comprising SEQ ID NO: 62; a third heavy chain CDR comprising SEQ ID NO: 63; a first light chain CDR comprising SEQ ID NO: 64; a second light chain CDR comprising SEQ ID NO: 65; and a third light chain CDR comprising SEQ ID NO: 66;
   (l) an antibody comprising: a first heavy chain CDR comprising SEQ ID NO: 67; a second heavy chain CDR comprising SEQ ID NO: 68; a third heavy chain CDR comprising SEQ ID NO: 69; a first light chain CDR comprising SEQ ID NO: 70; a second light chain CDR comprising SEQ ID NO: 71; and a third light chain CDR comprising SEQ ID NO: 72; and
   (m) an antibody comprising: a first heavy chain CDR comprising SEQ ID NO: 73; a second heavy chain CDR comprising SEQ ID NO: 74; a third heavy chain CDR comprising SEQ ID NO: 75; a first light chain CDR comprising SEQ ID NO: 76; a second light chain CDR comprising SEQ ID NO: 77; and a third light chain CDR comprising SEQ ID NO: 78.

2. An antibody that binds CXDR4 selected from the group consisting of:
   (a) an antibody comprising a heavy chain variable region comprising any one of SEQ ID NOs: 80, 84, 88, 92, 96, 100, 104, 108, 112, 116, 120, 124, 128; or
   (b) an antibody comprising a light chain variable region comprising any one of SEQ ID NOs: 82, 86, 90, 94, 98, 102, 106, 110, 114, 118, 122, 126, 130.

3. An antibody according to claim 1, which is a humanized antibody.

4. An antibody according to claim 2, which is a humanized antibody.

5. A protein selected from the group consisting of
(a) a protein comprising a variable heavy chain having any one of SEQ ID NOs: 80, 84, 88, 92, 96, 100, 104, 108, 112, 116, 120, 124, 128, or
(b) a protein comprising a variable light chain having any one of SEQ ID NOs: 82, 86, 90, 94, 98, 102, 106, 110, 114, 118, 122, 126, 130.

6. A nucleic acid encoding an antibody of claim 1.

7. A nucleic acid encoding an antibody of claim 2.

8. A nucleic acid encoding a protein of claim 5.

9. An expression vector which encodes an antibody of claim 1.

10. An expression vector which encodes an antibody of claim 2.

11. An expression vector which encodes a protein of claim 5.

12. A method of making an antibody according to claim 1, comprising culturing a cell comprising a nucleic acid encoding said antibody under conditions suitable for expression of said antibody.

13. A method of making an antibody according to claim 2, comprising culturing a cell comprising a nucleic acid encoding said antibody under conditions suitable for expression of said antibody.

14. A method of making a protein according to claim 5, comprising culturing a cell comprising a nucleic acid encoding said protein under conditions suitable for expression of said protein.

* * * * *

```
                          SEQUENCE LISTING

<160> NUMBER OF SEQ ID NOS: 144

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Phe Ser Phe Ser Asn Tyr Gly
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ile Asn Ser Ile Gly Gly Lys Thr
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Arg Phe Asn Trp Tyr Phe Asp Val
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Ser Leu Val His Ser Asn Gly Asn Thr Phe
1               5                   10

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Val Ser
1
```

```
<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Gln Ser Thr His Val Pro Trp Thr
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Phe Thr Phe Thr Asp Tyr Tyr
1               5

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ile Arg Asn Lys Ala Asn Gly Tyr Thr Thr
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Arg Asp Arg Asn Gly Asp Ser Ala Tyr
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Ser Leu Phe Asn Ser Arg Thr Arg Lys Asn Tyr
1               5                   10

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11
```

Trp Ala Ser
1

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Gln Ser Tyr Tyr Thr
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Phe Thr Phe Thr Asp Tyr Tyr
1               5

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ile Arg Asn Lys Ala Asn Gly Tyr Thr Thr
1               5                   10

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Arg Asp Asn Gly Gly Tyr Asp Tyr Ala Arg Gly Tyr Ala Met Asp
1               5                   10                  15

Tyr

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Ser Leu Leu Asn Ser Arg Thr Arg Lys Asn Tyr
1               5                   10

<210> SEQ ID NO 17
<211> LENGTH: 3

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Trp Ala Ser
1

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Gln Ser Tyr Asn Leu Arg Thr
1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Phe Thr Phe Thr Asp Tyr Tyr
1               5

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ile Arg Asn Lys Ala Asn Gly Tyr Thr Lys
1               5                   10

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Arg Asp Tyr Asp Asp Asp Tyr
1               5

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Ser Leu Phe Asn Ser Arg Thr Arg Lys Asn Tyr
```

<210> SEQ ID NO 23
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Trp Ala Ser
1

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Lys Gln Ser Tyr Tyr Leu Arg Thr
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Phe Thr Phe Thr Asp Tyr Tyr
1               5

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ile Arg Asn Lys Ala Asn Gly Tyr Thr Thr
1               5                   10

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Arg Asp Leu Gly Asp Asp Tyr
1               5

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic -continued

```
      peptide

<400> SEQUENCE: 28

Gln Ser Leu Phe Asn Ser Arg Thr Arg Lys Asn Tyr
1               5                   10

<210> SEQ ID NO 29
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Trp Ala Ser
1

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Lys Gln Ser Tyr Tyr Leu Arg Ala
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Phe Ala Phe Ser Ser Tyr Asp
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ile Ser Ser Gly Gly Ser Tyr Thr
1               5

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Arg His Arg Asp Lys Pro Leu Asp Tyr
1               5                   10

<210> SEQ ID NO 34
```

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 34

Gln Ser Leu Val His Ser Asn Gly Asn Thr Tyr
1               5                   10

<210> SEQ ID NO 35
<211> LENGTH: 3
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 35

Lys Val Ser
1

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 36

Ser Gln Ile Thr His Val Pro Trp Thr
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 37

Gly Phe Thr Phe Thr Asp Tyr Tyr
1               5

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 38

Ile Arg Asn Arg Ala Asn Gly Tyr Thr Thr
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 39

Ala Arg Asp Pro Leu Gly Arg Phe Asp Tyr
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Ser Leu Phe Asn Ser Arg Thr Arg Lys Asn Tyr
1               5                   10

<210> SEQ ID NO 41
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Trp Ala Ser
1

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Thr Gln Ser Ser Tyr Leu Arg Thr
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Phe Thr Phe Ser Asn Tyr Trp
1               5

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ile Arg Leu Lys Ser Asn Asn Tyr Ala Lys
1               5                   10

<210> SEQ ID NO 45
<211> LENGTH: 6
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 45

Thr Met Leu Gly Tyr Tyr
1               5

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Ser Val Ser Ser Arg Gln Ser Tyr
1               5                   10

<210> SEQ ID NO 47
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Tyr Ala Ser
1

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln His Ser Trp Glu Ile Pro Tyr Thr
1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Phe Thr Phe Thr Asp Tyr Tyr
1               5

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ile Arg Asn Lys Ala Asn Gly Tyr Thr Thr
1               5                   10
```

```
<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ala Arg Asp Gly Thr Thr Met Gly Ala Ala Asp Tyr
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln Ser Leu Phe Asn Ser Arg Thr Arg Lys Asn Tyr
1               5                   10

<210> SEQ ID NO 53
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Trp Ala Phe
1

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Lys Gln Ser Tyr Tyr Leu Arg Thr
1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Tyr Thr Phe Arg Ser Tyr Gly
1               5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56
```

```
Ile Tyr Pro Arg Ser Gly Asn Thr
1               5
```

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

```
Ala Arg Asp Ser Lys Asp Tyr Ala Met Asp Tyr
1               5                   10
```

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

```
Gln Ser Leu Leu Asp Ser Asp Gly Lys Thr Tyr
1               5                   10
```

<210> SEQ ID NO 59
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

```
Leu Met Ser
1
```

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

```
Trp Gln Gly Thr His Phe Pro His Thr
1               5
```

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

```
Gly Phe Thr Phe Thr Asp Tyr Tyr
1               5
```

<210> SEQ ID NO 62
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 62

Ile Arg Asn Lys Ala Asn Gly Tyr Thr Thr
1               5                   10

<210> SEQ ID NO 63
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ala Arg Asp Ala Gly Ser Gly Ser His Tyr Phe Asp Tyr
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gln Ser Leu Phe Asn Ser Arg Thr Arg Lys Asn Tyr
1               5                   10

<210> SEQ ID NO 65
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Trp Ala Leu
1

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Lys Gln Ser Tyr Tyr Leu Arg Thr
1               5

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Phe Thr Phe Thr Asp Tyr Tyr
1               5
```

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ile Arg Asn Lys Ala Asn Gly Tyr Thr Thr
1               5                   10

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ala Arg Gly Thr Gly His Phe Asp Tyr
1               5

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Ser Leu Phe Asn Ser Arg Thr Arg Lys Asn Tyr
1               5                   10

<210> SEQ ID NO 71
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Trp Ala Ser
1

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Lys Gln Ser Tyr Tyr Leu Arg Thr
1               5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 73

Gly Tyr Thr Phe Thr Asp Tyr His
1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ile Asn Pro Tyr Asn Gly Asp Ile
1               5

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ala Arg Gly Gly Gln Leu Gly Leu Ala Tyr
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gln Ser Leu Phe Asn Ser Arg Thr Arg Lys Asn Tyr
1               5                   10

<210> SEQ ID NO 77
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Trp Ala Leu
1

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Lys Gln Ser Tyr Tyr Leu Arg Thr
1               5

<210> SEQ ID NO 79
<211> LENGTH: 348
<212> TYPE: DNA
```

<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(348)

<400> SEQUENCE: 79

```
gag gtg cag ggg gtg gag tct ggg gga ggc tta gtg aag cct gga ggg       48
Glu Val Gln Gly Val Glu Ser Gly Gly Gly Leu Val Lys Pro Gly Gly
1               5                   10                  15 tcc ctg aaa ctc tcc tgt gca gcc tct gga ttc tct ttc agt aac tat       96
Ser Leu Lys Leu Ser Cys Ala Ala Ser Gly Phe Ser Phe Ser Asn Tyr
            20                  25                  30 ggc atg tct tgg gtt cgc cag act ccg gag aag agg ctg gag tgg gtc      144
Gly Met Ser Trp Val Arg Gln Thr Pro Glu Lys Arg Leu Glu Trp Val
        35                  40                  45 gca gcc att aat agt att ggt ggt aag acc tac tat cca gac act gtg      192
Ala Ala Ile Asn Ser Ile Gly Gly Lys Thr Tyr Tyr Pro Asp Thr Val
    50                  55                  60 aag ggc cga ttc acc atc tcc agg gac aat gcc aag aac acc ctg tac      240
Lys Gly Arg Phe Thr Ile Ser Arg Asp Asn Ala Lys Asn Thr Leu Tyr
65                  70                  75                  80 ctg caa atg agc agt ctg agg tct ggt gac aca gcc ttg tat tac tgt      288
Leu Gln Met Ser Ser Leu Arg Ser Gly Asp Thr Ala Leu Tyr Tyr Cys
                85                  90                  95 gca aga ttt aac tgg tac ttc gat gtc tgg ggc aca ggg acc act ctc      336
Ala Arg Phe Asn Trp Tyr Phe Asp Val Trp Gly Thr Gly Thr Thr Leu
            100                 105                 110 aca gtc tcc tca                                                      348
Thr Val Ser Ser
        115
```

<210> SEQ ID NO 80
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 80

```
Glu Val Gln Gly Val Glu Ser Gly Gly Gly Leu Val Lys Pro Gly Gly
1               5                   10                  15

Ser Leu Lys Leu Ser Cys Ala Ala Ser Gly Phe Ser Phe Ser Asn Tyr
            20                  25                  30

Gly Met Ser Trp Val Arg Gln Thr Pro Glu Lys Arg Leu Glu Trp Val
        35                  40                  45

Ala Ala Ile Asn Ser Ile Gly Gly Lys Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Gly Asp Thr Ala Leu Tyr Tyr Cys
                85                  90                  95

Ala Arg Phe Asn Trp Tyr Phe Asp Val Trp Gly Thr Gly Thr Thr Leu
            100                 105                 110

Thr Val Ser Ser
        115
```

<210> SEQ ID NO 81

<211> LENGTH: 337
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(336)

<400> SEQUENCE: 81

```
gac gtt gtg atg acc cag act cca ctc tcc ctg cct gtc agt ctt gga        48
Asp Val Val Met Thr Gln Thr Pro Leu Ser Leu Pro Val Ser Leu Gly
1               5                   10                  15 gat caa gcc tcc atc tct tgc aga tct agt cag agc ctt gta cac agt        96
Asp Gln Ala Ser Ile Ser Cys Arg Ser Ser Gln Ser Leu Val His Ser
                20                  25                  30 aat gga aac acc ttt tta cat tgg tac ctg ctg aag cca ggc cag tct       144
Asn Gly Asn Thr Phe Leu His Trp Tyr Leu Leu Lys Pro Gly Gln Ser
            35                  40                  45 cca aag ctc ctg atc tac aaa gtt tcc agc cga ttt tct ggg gtc cca       192
Pro Lys Leu Leu Ile Tyr Lys Val Ser Ser Arg Phe Ser Gly Val Pro
        50                  55                  60 gac agg ttc agt ggc agt gga tca ggg acc gat ttc aca ctc aag atc       240
Asp Arg Phe Ser Gly Ser Gly Ser Gly Thr Asp Phe Thr Leu Lys Ile
65                  70                  75                  80 acc aga gtg gag gct gag gat ctg gga ctt tat ttc tgc tct caa agt       288
Thr Arg Val Glu Ala Glu Asp Leu Gly Leu Tyr Phe Cys Ser Gln Ser
                85                  90                  95 aca cat gtt ccg tgg acg ttc ggt gga ggc acc aag ctg gaa ata aaa c     337
Thr His Val Pro Trp Thr Phe Gly Gly Gly Thr Lys Leu Glu Ile Lys
            100                 105                 110
```

<210> SEQ ID NO 82
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 82

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Phe Leu His Trp Tyr Leu Leu Lys Pro Gly Gln Ser
            35                  40                  45

Pro Lys Leu Leu Ile Tyr Lys Val Ser Ser Arg Phe Ser Gly Val Pro
        50                  55                  60

Asp Arg Phe Ser Gly Ser Gly Ser Gly Thr Asp Phe Thr Leu Lys Ile
65                  70                  75                  80

Thr Arg Val Glu Ala Glu Asp Leu Gly Leu Tyr Phe Cys Ser Gln Ser
                85                  90                  95

Thr His Val Pro Trp Thr Phe Gly Gly Gly Thr Lys Leu Glu Ile Lys
            100                 105                 110
```

<210> SEQ ID NO 83
<211> LENGTH: 357
<212> TYPE: DNA
<213> ORGANISM: Artificial Sequence
<220> FEATURE:
<223> OTHER INFORMATION: Description of Artificial Sequence: Synthetic -continued

```
        polynucleotide
<220> FEATURE:
<221> NAME/KEY: CDS
<222> LOCATION: (1)..(357)

<400> SEQUENCE: 83 gat gtg cac ctg gtg gag tct gga gga ggc ttg gta cag cct ggg gct        48
Asp Val His Leu Val Glu Ser Gly Gly Gly Leu Val Gln Pro Gly Ala
1               5                   10                  15 tct ctg aga ctc tcc tgt gca act tct ggg ttc acc ttc act gat tac        96
Ser Leu Arg Leu Ser Cys Ala Thr Ser Gly Phe Thr Phe Thr Asp Tyr
            20                  25                  30 tac atg agc tgg gtc cgc cag cct cca gga aag gca ctt gag tgg ttg        144
Tyr Met Ser Trp Val Arg Gln Pro Pro Gly Lys Ala Leu Glu Trp Leu
        35                  40                  45 ggt ttt att aga aac aaa gct aat ggt tac aca aca gag tac agt gca        192
Gly Phe Ile Arg Asn Lys Ala Asn Gly Tyr Thr Thr Glu Tyr Ser Ala
    50                  55                  60 tct gtg aag ggt cgg ttc acc atc tcc aga gat aat tcc caa agc atc        240
Ser Val Lys Gly Arg Phe Thr Ile Ser Arg Asp Asn Ser Gln Ser Ile
65                  70                  75                  80 ctc tat ctt caa atg aac aca ctg aga gct gag gac agt gcc act tat        288
Leu Tyr Leu Gln Met Asn Thr Leu Arg Ala Glu Asp Ser Ala Thr Tyr
                85                  90                  95 tac tgt gca aga gat agg aat ggt gac tcc gct tac tgg ggc caa ggg        336
Tyr Cys Ala Arg Asp Arg Asn Gly Asp Ser Ala Tyr Trp Gly Gln Gly
            100                 105                 110 act ctg gtc act gtc tct gca                                            357
Thr Leu Val Thr Val Ser Ala
        115

<210> SEQ ID NO 84
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Asp Val His Leu Val Glu Ser Gly Gly Gly Leu Val Gln Pro Gly Ala
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Ala Arg Asp Arg Asn Gly Asp Ser Ala Tyr Trp Gly Gln Gly
            100                 105                 110

Thr Leu Val Thr Val Ser Ala
        115

<210> SEQ ID NO 85
<211> LENGTH: 332
<212> TYPE: DNA
<213> ORGANISM: Artificial Sequence
```

<220> FEATURE:
<223> OTHER INFORMATION: Description of Artificial Sequence: Synthetic
      polynucleotide
<220> FEATURE:
<221> NAME/KEY: CDS
<222> LOCATION: (1)..(330)

<400> SEQUENCE: 85

```
gat att cta atg acc cag tct cca tcc tcc ctg gct gtg tca gca gga      48
Asp Ile Leu Met Thr Gln Ser Pro Ser Ser Leu Ala Val Ser Ala Gly
1               5                   10                  15 gag aag gtc act atg agc tgc aaa tcc agt cag agt ctg ttc aac agt      96
Glu Lys Val Thr Met Ser Cys Lys Ser Ser Gln Ser Leu Phe Asn Ser
            20                  25                  30 aga acc cgg aag aac tac ttg gct tgg tac cag cag aaa cca ggg cag     144
Arg Thr Arg Lys Asn Tyr Leu Ala Trp Tyr Gln Gln Lys Pro Gly Gln
        35                  40                  45 tct cct aaa ctg ctg atc tac tgg gca tcc act agg gaa tct ggg gtc     192
Ser Pro Lys Leu Leu Ile Tyr Trp Ala Ser Thr Arg Glu Ser Gly Val
    50                  55                  60 cct gat cgc ttc aca ggc agt gga tct ggg aca gat ctc act ctc acc     240
Pro Asp Arg Phe Thr Gly Ser Gly Ser Gly Thr Asp Leu Thr Leu Thr
65                  70                  75                  80 atc agc agt gtg cag gct gaa gac ctg gca gtt tat tac tgc aag caa     288
Ile Ser Ser Val Gln Ala Glu Asp Leu Ala Val Tyr Tyr Cys Lys Gln
                85                  90                  95 tct tat tat acg ttc gga tcg ggg acc aag ctg gag ctg aaa cg          332
Ser Tyr Tyr Thr Phe Gly Ser Gly Thr Lys Leu Glu Leu Lys
            100                 105                 110
```

<210> SEQ ID NO 86
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Asp Ile Leu Met Thr Gln Ser Pro Ser Ser Leu Ala Val Ser Ala Gly
1               5                   10                  15

Glu Lys Val Thr Met Ser Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Leu Thr Leu Thr
65                  70                  75                  80

Ile Ser Ser Val Gln Ala Glu Asp Leu Ala Val Tyr Tyr Cys Lys Gln
                85                  90                  95

Ser Tyr Tyr Thr Phe Gly Ser Gly Thr Lys Leu Glu Leu Lys
            100                 105                 110

<210> SEQ ID NO 87
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS

<222> LOCATION: (1)..(378)

<400> SEQUENCE: 87

```
gag gtg aag ctg atg gag tct gga gga ggc ttg gta cag cct ggg gct      48
Glu Val Lys Leu Met Glu Ser Gly Gly Gly Leu Val Gln Pro Gly Ala
1               5                   10                  15 tct ctg aga ctc tcc tgt gta act tct ggg ttc acc ttc act gat tac      96
Ser Leu Arg Leu Ser Cys Val Thr Ser Gly Phe Thr Phe Thr Asp Tyr
            20                  25                  30 tac atg agc tgg gtc cgc cag cct cca gga aag gca ctt gag tgg ttg     144
Tyr Met Ser Trp Val Arg Gln Pro Pro Gly Lys Ala Leu Glu Trp Leu
        35                  40                  45 ggt ttt att aga aac aaa gct aat ggt tac aca aca gac tac agt gca     192
Gly Phe Ile Arg Asn Lys Ala Asn Gly Tyr Thr Thr Asp Tyr Ser Ala
    50                  55                  60 tct gtg aag ggt cgg ttc acc atc tcc aga gat aat tcc caa agc atc     240
Ser Val Lys Gly Arg Phe Thr Ile Ser Arg Asp Asn Ser Gln Ser Ile
65                  70                  75                  80 ctc tat ctt caa atg aac aca ctg aga gct gag gac agt gcc act tat     288
Leu Tyr Leu Gln Met Asn Thr Leu Arg Ala Glu Asp Ser Ala Thr Tyr
                85                  90                  95 tac tgt gcg aga gat aac ggg ggg tat gat tac gca cgg ggc tat gct     336
Tyr Cys Ala Arg Asp Asn Gly Gly Tyr Asp Tyr Ala Arg Gly Tyr Ala
            100                 105                 110 atg gac tac tgg ggt caa gga acc tca gtc act gtc tct gca             378
Met Asp Tyr Trp Gly Gln Gly Thr Ser Val Thr Val Ser Ala
        115                 120                 125
```

<210> SEQ ID NO 88
<211> LENGTH: 126
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 88

```
Glu Val Lys Leu Met Glu Ser Gly Gly Gly Leu Val Gln Pro Gly Ala
1               5                   10                  15

Ser Leu Arg Leu Ser Cys Val Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Asp Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Ala Arg Asp Asn Gly Gly Tyr Asp Tyr Ala Arg Gly Tyr Ala
            100                 105                 110

Met Asp Tyr Trp Gly Gln Gly Thr Ser Val Thr Val Ser Ala
        115                 120                 125
```

<210> SEQ ID NO 89
<211> LENGTH: 337
<212> TYPE: DNA
<213> ORGANISM: Artificial Sequence
<220> FEATURE:
<223> OTHER INFORMATION: Description of Artificial Sequence: Synthetic polynucleotide

<220> FEATURE:
<221> NAME/KEY: CDS
<222> LOCATION: (1)..(336)

<400> SEQUENCE: 89

```
gat att gtg atg acc caa tct cca tcc tcc ctg gct gtg tca gca gga      48
Asp Ile Val Met Thr Gln Ser Pro Ser Ser Leu Ala Val Ser Ala Gly
1               5                   10                  15 gag aag gtc act atg agc tgc aaa tcc agt cag agt ctg ctc aac agt      96
Glu Lys Val Thr Met Ser Cys Lys Ser Ser Gln Ser Leu Leu Asn Ser
            20                  25                  30 aga acc cga aag aac tac ttg gct tgg tac cag cag aaa cca ggg cag     144
Arg Thr Arg Lys Asn Tyr Leu Ala Trp Tyr Gln Gln Lys Pro Gly Gln
        35                  40                  45 tct cct aaa cta ctg atc tac tgg gca tcc act agg gaa tct ggg gtc     192
Ser Pro Lys Leu Leu Ile Tyr Trp Ala Ser Thr Arg Glu Ser Gly Val
    50                  55                  60 cct gat cgc ttc aca ggc agt gga tct ggg aca gat ttc act ctc acc     240
Pro Asp Arg Phe Thr Gly Ser Gly Ser Gly Thr Asp Phe Thr Leu Thr
65                  70                  75                  80 atc agc agt gtg cag gct gaa gac ctg gcg gtt tat tac tgc acg caa     288
Ile Ser Ser Val Gln Ala Glu Asp Leu Ala Val Tyr Tyr Cys Thr Gln
                85                  90                  95 tct tat aat ctt cgg acg ttc ggt gga ggc acc aag ctg gag ctg aaa c   337
Ser Tyr Asn Leu Arg Thr Phe Gly Gly Gly Thr Lys Leu Glu Leu Lys
            100                 105                 110
```

<210> SEQ ID NO 90
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

```
Asp Ile Val Met Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Thr Gln
                85                  90                  95

Ser Tyr Asn Leu Arg Thr Phe Gly Gly Gly Thr Lys Leu Glu Leu Lys
            100                 105                 110
```

<210> SEQ ID NO 91
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(351)

<400> SEQUENCE: 91

```
gag gtg cag ctt ctg gag tct gga gga ggc ttg gta cag cct ggg gct     48
Glu Val Gln Leu Leu Glu Ser Gly Gly Gly Leu Val Gln Pro Gly Ala
1               5                  10                  15 tct ctg aga ctc tcc tgt gca act tct ggg ttc acc ttc act gat tac     96
Ser Leu Arg Leu Ser Cys Ala Thr Ser Gly Phe Thr Phe Thr Asp Tyr
            20                  25                  30 tac atg agc tgg gtc cgc cag cct cca gga aag gca ctt gag tgg ttg    144
Tyr Met Ser Trp Val Arg Gln Pro Pro Gly Lys Ala Leu Glu Trp Leu
        35                  40                  45 ggt ttt att aga aac aaa gct aat ggt tac aca aaa gag tac agt gca    192
Gly Phe Ile Arg Asn Lys Ala Asn Gly Tyr Thr Lys Glu Tyr Ser Ala
    50                  55                  60 tct gtg aag ggt cgg ttc acc atc tcc aga gat aat tcc caa agc atc    240
Ser Val Lys Gly Arg Phe Thr Ile Ser Arg Asp Asn Ser Gln Ser Ile
65                  70                  75                  80 ctc tat ctt caa atg aac aca ctg gga gct gag gac agt gcc act tat    288
Leu Tyr Leu Gln Met Asn Thr Leu Gly Ala Glu Asp Ser Ala Thr Tyr
                85                  90                  95 tac tgt gca cgt gac tac gac gac gac tac tgg ggc caa ggc acc act    336
Tyr Cys Ala Arg Asp Tyr Asp Asp Asp Tyr Trp Gly Gln Gly Thr Thr
            100                 105                 110 ctc aca gtc tcc tca                                                 351
Leu Thr Val Ser Ser
        115

<210> SEQ ID NO 92
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Glu Val Gln Leu Leu Glu Ser Gly Gly Gly Leu Val Gln Pro Gly Ala
1               5                  10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Lys Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Gly Ala Glu Asp Ser Ala Thr Tyr
                85                  90                  95

Tyr Cys Ala Arg Asp Tyr Asp Asp Asp Tyr Trp Gly Gln Gly Thr Thr
            100                 105                 110

Leu Thr Val Ser Ser
        115

<210> SEQ ID NO 93
<211> LENGTH: 337
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)
```

<400> SEQUENCE: 93

```
gat att aag atg acc cag tct cca tcc tcc ctg gct gtg tca aca gga      48
Asp Ile Lys Met Thr Gln Ser Pro Ser Ser Leu Ala Val Ser Thr Gly
1               5                   10                  15 gag aag gtc act atg cgc tgc aaa tcc agt cag agt ctg ttc aac agt      96
Glu Lys Val Thr Met Arg Cys Lys Ser Ser Gln Ser Leu Phe Asn Ser
            20                  25                  30 aga acc cga aag aac tac ttg gct tgg tac cag cag aag cca ggg cag      144
Arg Thr Arg Lys Asn Tyr Leu Ala Trp Tyr Gln Gln Lys Pro Gly Gln
        35                  40                  45 tct cct aaa ctg ctg atc tac tgg gca tcc act agg gaa tct ggg gtc      192
Ser Pro Lys Leu Leu Ile Tyr Trp Ala Ser Thr Arg Glu Ser Gly Val
    50                  55                  60 cct gat cgc ttc aca ggc agt gga tct ggg aca gat ttc act ctc acc      240
Pro Asp Arg Phe Thr Gly Ser Gly Ser Gly Thr Asp Phe Thr Leu Thr
65                  70                  75                  80 atc agc agt gtg cag gct gaa gac ctg gca gtt tat tac tgc aag caa      288
Ile Ser Ser Val Gln Ala Glu Asp Leu Ala Val Tyr Tyr Cys Lys Gln
                85                  90                  95 tct tat tat ctt cgg acg ttc ggt gga ggc acc aag ctg gaa atc aaa c    337
Ser Tyr Tyr Leu Arg Thr Phe Gly Gly Gly Thr Lys Leu Glu Ile Lys
            100                 105                 110
```

<210> SEQ ID NO 94
<211> LENGTH: 112
<212> TYPE: PRT
<213> ORGANISM: Artificial Sequence
<220> FEATURE:
<223> OTHER INFORMATION: Description of Artificial Sequence: Synthetic
  polypeptide

<400> SEQUENCE: 94

```
Asp Ile Lys Met Thr Gln Ser Pro Ser Ser Leu Ala Val Ser Thr Gly
1               5                   10                  15

Glu Lys Val Thr Met Arg Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Tyr Leu Arg Thr Phe Gly Gly Gly Thr Lys Leu Glu Ile Lys
            100                 105                 110
```

<210> SEQ ID NO 95
<211> LENGTH: 349
<212> TYPE: DNA
<213> ORGANISM: Artificial Sequence
<220> FEATURE:
<223> OTHER INFORMATION: Description of Artificial Sequence: Synthetic
  polynucleotide
<220> FEATURE:
<221> NAME/KEY: CDS
<222> LOCATION: (1)..(348)

<400> SEQUENCE: 95

```
gag gtg aag ctg gtg gag tct gga gga gac ttg gta cag cct ggg act      48
Glu Val Lys Leu Val Glu Ser Gly Gly Asp Leu Val Gln Pro Gly Thr
```

```
                1               5                      10                     15
tct ctg aga ctc tcc tgt gca act tct ggg ttc acc ttc act gat tac      96
Ser Leu Arg Leu Ser Cys Ala Thr Ser Gly Phe Thr Phe Thr Asp Tyr
            20                      25                     30 tac atg agc tgg gtc cgc cag cct cca gga aag gca ctt gag tgg ttg     144
Tyr Met Ser Trp Val Arg Gln Pro Pro Gly Lys Ala Leu Glu Trp Leu
        35                      40                     45 ggt ttt att aga aac aaa gct aat ggt tac aca aca gag tac agt gca     192
Gly Phe Ile Arg Asn Lys Ala Asn Gly Tyr Thr Thr Glu Tyr Ser Ala
    50                      55                     60 tct gtg aag ggt cgg ttc acc atc tcc agg gat aat tcc caa agc atc     240
Ser Val Lys Gly Arg Phe Thr Ile Ser Arg Asp Asn Ser Gln Ser Ile
65                      70                     75                     80 ctc tat ctt caa atg aac act ctg aga gct gag gac agt gcc act tat     288
Leu Tyr Leu Gln Met Asn Thr Leu Arg Ala Glu Asp Ser Ala Thr Tyr
                85                      90                     95 tac tgt gca aga gat ctg ggt gat gac tac tgg ggc caa ggc acc act     336
Tyr Cys Ala Arg Asp Leu Gly Asp Asp Tyr Trp Gly Gln Gly Thr Thr
            100                     105                    110 ctc aca gtc tcc t                                                   349
Leu Thr Val Ser
        115
```

<210> SEQ ID NO 96
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Glu Val Lys Leu Val Glu Ser Gly Gly Asp Leu Val Gln Pro Gly Thr
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Ala Arg Asp Leu Gly Asp Asp Tyr Trp Gly Gln Gly Thr Thr
            100                 105                 110

Leu Thr Val Ser
        115

<210> SEQ ID NO 97
<211> LENGTH: 337
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 97

```
gac att cag atg atg cag tct cca tcc tcc ctg gct gtg tca gct gga      48
Asp Ile Gln Met Met Gln Ser Pro Ser Ser Leu Ala Val Ser Ala Gly
1               5                   10                  15 gag aag gtc act atg agc tgc aaa tcc agt cag agt ctg ttc aac agt      96
Glu Lys Val Thr Met Ser Cys Lys Ser Ser Gln Ser Leu Phe Asn Ser
            20                  25                  30 aga acc cga aag aac tac ttg gct tgg tac cag cag aaa cca ggg cag     144
Arg Thr Arg Lys Asn Tyr Leu Ala Trp Tyr Gln Gln Lys Pro Gly Gln
        35                  40                  45 tct cct aaa ctg ctg atc tac tgg gca tcc aaa agg gaa tct ggg gtc     192
Ser Pro Lys Leu Leu Ile Tyr Trp Ala Ser Lys Arg Glu Ser Gly Val
    50                  55                  60 cct gct cgc ttc aca ggc agt gga tct ggg aca gat ttc act ctc acc     240
Pro Ala Arg Phe Thr Gly Ser Gly Ser Gly Thr Asp Phe Thr Leu Thr
65                  70                  75                  80 atc agc agt gtg cag gct gaa gac ctg gca gtt tat tac tgc aag caa     288
Ile Ser Ser Val Gln Ala Glu Asp Leu Ala Val Tyr Tyr Cys Lys Gln
                85                  90                  95 tct tat tat ctt agg gcg ttc ggt gga ggc acc aag ctg gaa ata aaa c   337
Ser Tyr Tyr Leu Arg Ala Phe Gly Gly Gly Thr Lys Leu Glu Ile Lys
            100                 105                 110

<210> SEQ ID NO 98
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Asp Ile Gln Met Met Gln Ser Pro Ser Ser Leu Ala Val Ser Ala Gly
1               5                   10                  15

Glu Lys Val Thr Met Ser Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Lys Arg Glu Ser Gly Val
    50                  55                  60

Pro Ala Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Tyr Leu Arg Ala Phe Gly Gly Gly Thr Lys Leu Glu Ile Lys
            100                 105                 110

<210> SEQ ID NO 99
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(351)

<400> SEQUENCE: 99 gag gtg caa ctg gtg gag tct ggg gga ggc tta gtg aag cct gga ggg      48
Glu Val Gln Leu Val Glu Ser Gly Gly Gly Leu Val Lys Pro Gly Gly
1               5                   10                  15 tcc ctg aaa ctc tcc tgt gca gcc tct gga ttc gct ttc agt agc tat      96
```

```
Ser Leu Lys Leu Ser Cys Ala Ala Ser Gly Phe Ala Phe Ser Ser Tyr
        20                  25                  30 gac atg tct tgg gtt cgc cag act ccg gaa aag agg ctg gaa tgg gtc    144
Asp Met Ser Trp Val Arg Gln Thr Pro Glu Lys Arg Leu Glu Trp Val
        35                  40                  45 gca acc att agt agt ggt ggt agt tac acc tac tat cca gac agt gtg    192
Ala Thr Ile Ser Ser Gly Gly Ser Tyr Thr Tyr Tyr Pro Asp Ser Val
    50                  55                  60 aag ggc cga ttc acc atc tcc aga gac aat gcc agg aac acc cta tac    240
Lys Gly Arg Phe Thr Ile Ser Arg Asp Asn Ala Arg Asn Thr Leu Tyr
65                  70                  75                  80 cta caa atg agc agt ctg agg tct gag gac acg gcc ttg tat tac tgt    288
Leu Gln Met Ser Ser Leu Arg Ser Glu Asp Thr Ala Leu Tyr Tyr Cys
                85                  90                  95 gca aga cat cgg gat aaa ccc ctt gac tac tgg ggc caa ggc acc act    336
Ala Arg His Arg Asp Lys Pro Leu Asp Tyr Trp Gly Gln Gly Thr Thr
            100                 105                 110 ctc aca gtc tcc tca                                                351
Leu Thr Val Ser Ser
        115

<210> SEQ ID NO 100
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ser Tyr
            20                  25                  30

Asp Met Ser Trp Val Arg Gln Thr Pro Glu Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Arg Ser Glu Asp Thr Ala Leu Tyr Tyr Cys
                85                  90                  95

Ala Arg His Arg Asp Lys Pro Leu Asp Tyr Trp Gly Gln Gly Thr Thr
            100                 105                 110

Leu Thr Val Ser Ser
        115

<210> SEQ ID NO 101
<211> LENGTH: 337
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 101 gac att gtg atg acc cag tct cca ctc tcc ctg cct gtc agt ctt gga     48
Asp Ile Val Met Thr Gln Ser Pro Leu Ser Leu Pro Val Ser Leu Gly
1               5                   10                  15
```

```
gat caa gcc tcc atc tct tgc aga tct agt cag agc ctt gta cac agt        96
Asp Gln Ala Ser Ile Ser Cys Arg Ser Ser Gln Ser Leu Val His Ser
            20                  25                  30 aat gga aac acc tat tta aat tgg tac ctg cag aag cca ggc cag tct       144
Asn Gly Asn Thr Tyr Leu Asn Trp Tyr Leu Gln Lys Pro Gly Gln Ser
        35                  40                  45 cca aaa ctc ctg atc tac aaa gtt tcc aac cga ttt tct ggg gtc cca       192
Pro Lys Leu Leu Ile Tyr Lys Val Ser Asn Arg Phe Ser Gly Val Pro
    50                  55                  60 gac agg ttc agt ggc agt gga tca ggg aca gat ttc aca ctc aag atc       240
Asp Arg Phe Ser Gly Ser Gly Ser Gly Thr Asp Phe Thr Leu Lys Ile
65                  70                  75                  80 agc aga gtg gag gct gag gat ctg gga gtt tat ttc tgc tct caa att       288
Ser Arg Val Glu Ala Glu Asp Leu Gly Val Tyr Phe Cys Ser Gln Ile
                85                  90                  95 aca cat gtt cct tgg acg ttc ggt gga ggc acc aag ctg gaa ata aaa c     337
Thr His Val Pro Trp Thr Phe Gly Gly Gly Thr Lys Leu Glu Ile Lys
            100                 105                 110
```

<210> SEQ ID NO 102
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

```
Asp Ile Val Met Thr Gln Ser Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Asn Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ile
                85                  90                  95

Thr His Val Pro Trp Thr Phe Gly Gly Gly Thr Lys Leu Glu Ile Lys
            100                 105                 110
```

<210> SEQ ID NO 103
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(357)

<400> SEQUENCE: 103

```
gaa gtg aag ctg gtg gag tct gga gga ggc ttg gta cag cct ggg gct        48
Glu Val Lys Leu Val Glu Ser Gly Gly Gly Leu Val Gln Pro Gly Ala
1               5                   10                  15 tct ctg aga ctc tcc tgt gca act tct ggg ttc acc ttc act gat tac        96
Ser Leu Arg Leu Ser Cys Ala Thr Ser Gly Phe Thr Phe Thr Asp Tyr
            20                  25                  30
```

```
tac atg acc tgg gtc cgc cag cct cca gga aag gca ctt gag tgg ttg      144
Tyr Met Thr Trp Val Arg Gln Pro Pro Gly Lys Ala Leu Glu Trp Leu
        35                  40                  45 ggt ttt att aga aac aga gct aat ggt tac aca aca gag tac aat gca      192
Gly Phe Ile Arg Asn Arg Ala Asn Gly Tyr Thr Thr Glu Tyr Asn Ala
 50                  55                  60 tct gtg aag ggt cgg ttc acc atc tcc aga gat aat tcc caa aac atc      240
Ser Val Lys Gly Arg Phe Thr Ile Ser Arg Asp Asn Ser Gln Asn Ile
 65                  70                  75                  80 ctc tat ctt caa atg aac acc ctg aga act gag gac agt gcc act tat      288
Leu Tyr Leu Gln Met Asn Thr Leu Arg Thr Glu Asp Ser Ala Thr Tyr
                 85                  90                  95 tac tgt gcc aga gat ccc ctg gga cgc ttt gac tac tgg ggc cga ggc      336
Tyr Cys Ala Arg Asp Pro Leu Gly Arg Phe Asp Tyr Trp Gly Arg Gly
            100                 105                 110 acc act ctc aca gtc tcc tca                                          357
Thr Thr Leu Thr Val Ser Ser
        115
```

<210> SEQ ID NO 104
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

```
Glu Val Lys Leu Val Glu Ser Gly Gly Gly Leu Val Gln Pro Gly Ala
 1               5                  10                  15

Ser Leu Arg Leu Ser Cys Ala Thr Ser Gly Phe Thr Phe Thr Asp Tyr
            20                  25                  30

Tyr Met Thr Trp Val Arg Gln Pro Pro Gly Lys Ala Leu Glu Trp Leu
        35                  40                  45

Gly Phe Ile Arg Asn Arg Ala Asn Gly Tyr Thr Thr Glu Tyr Asn Ala
 50                  55                  60

Ser Val Lys Gly Arg Phe Thr Ile Ser Arg Asp Asn Ser Gln Asn Ile
 65                  70                  75                  80

Leu Tyr Leu Gln Met Asn Thr Leu Arg Thr Glu Asp Ser Ala Thr Tyr
                 85                  90                  95

Tyr Cys Ala Arg Asp Pro Leu Gly Arg Phe Asp Tyr Trp Gly Arg Gly
            100                 105                 110

Thr Thr Leu Thr Val Ser Ser
        115
```

<210> SEQ ID NO 105
<211> LENGTH: 337
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 105

```
gat att aag atg acc cag tct cca tcc tcc ctg gct gtg tca gca gga       48
Asp Ile Lys Met Thr Gln Ser Pro Ser Ser Leu Ala Val Ser Ala Gly
 1               5                  10                  15 gag aag gtc act atg agt tgc aaa tcc agt cag agt ctg ttc aac agt       96
Glu Lys Val Thr Met Ser Cys Lys Ser Ser Gln Ser Leu Phe Asn Ser
```

```
                    20                  25                  30
aga acc cga aag aac tac ttg gct tgg tac cag cag aaa cca ggg cag      144
Arg Thr Arg Lys Asn Tyr Leu Ala Trp Tyr Gln Gln Lys Pro Gly Gln
            35                  40                  45 tct cct aaa ctg ctg atc tac tgg gct tct att agg gaa tct ggg gtc      192
Ser Pro Lys Leu Leu Ile Tyr Trp Ala Ser Ile Arg Glu Ser Gly Val
        50                  55                  60 cct gat cgc ttc aca ggc agt gga tct ggg aca gat ttc act ctc acc      240
Pro Asp Arg Phe Thr Gly Ser Gly Ser Gly Thr Asp Phe Thr Leu Thr
65                  70                  75                  80 atc agc agt gtg cag gct gaa gac ctg gca gtt tat tac tgc aca cag      288
Ile Ser Ser Val Gln Ala Glu Asp Leu Ala Val Tyr Tyr Cys Thr Gln
                85                  90                  95 tct tct tat ctt cgg acg ttc ggt gga ggc acc gag ctg gaa atc aaa c    337
Ser Ser Tyr Leu Arg Thr Phe Gly Gly Gly Thr Glu Leu Glu Ile Lys
            100                 105                 110

<210> SEQ ID NO 106
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Asp Ile Lys Met Thr Gln Ser Pro Ser Ser Leu Ala Val Ser Ala Gly
1               5                   10                  15

Glu Lys Val Thr Met Ser Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Ile Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Thr Gln
                85                  90                  95

Ser Ser Tyr Leu Arg Thr Phe Gly Gly Gly Thr Glu Leu Glu Ile Lys
            100                 105                 110

<210> SEQ ID NO 107
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(345)

<400> SEQUENCE: 107 gac gtg atg ctg gtg gag tct gga gga ggc ttg gtg caa cct gga gga      48
Asp Val Met Leu Val Glu Ser Gly Gly Gly Leu Val Gln Pro Gly Gly
1               5                   10                  15 tcc atg aaa ctc tcc tgt att ggc tct gga ttc act ttc agt aac tac      96
Ser Met Lys Leu Ser Cys Ile Gly Ser Gly Phe Thr Phe Ser Asn Tyr
            20                  25                  30 tgg atg aac tgg gtc cgc cag tct cca gag aag ggg ctt gag tgg gtt     144
Trp Met Asn Trp Val Arg Gln Ser Pro Glu Lys Gly Leu Glu Trp Val
        35                  40                  45
```

```
gct gaa att aga ttg aaa tcg aat aat tat gca aaa cat tat gcg gag     192
Ala Glu Ile Arg Leu Lys Ser Asn Asn Tyr Ala Lys His Tyr Ala Glu
         50                  55                  60 tct gtg aaa ggg agg ttc acc atc tca aga gat gat tcc aaa agt cgt     240
Ser Val Lys Gly Arg Phe Thr Ile Ser Arg Asp Asp Ser Lys Ser Arg
 65                  70                  75                  80 gtc tac ctg caa atg acc aac tta aga act gaa gac act ggc att tat     288
Val Tyr Leu Gln Met Thr Asn Leu Arg Thr Glu Asp Thr Gly Ile Tyr
                 85                  90                  95 tac tgt acc atg ctg gga tac tac tgg ggc caa ggc act ctc aca         336
Tyr Cys Thr Met Leu Gly Tyr Tyr Trp Gly Gln Gly Thr Thr Leu Thr
            100                 105                 110 gtc tcc tca                                                         345
Val Ser Ser
        115

<210> SEQ ID NO 108
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Asp Val Met Leu Val Glu Ser Gly Gly Gly Leu Val Gln Pro Gly Gly
1               5                   10                  15

Ser Met Lys Leu Ser Cys Ile Gly Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Lys His Tyr Ala Glu
    50                  55                  60

Ser Val Lys Gly Arg Phe Thr Ile Ser Arg Asp Asp Ser Lys Ser Arg
65                  70                  75                  80

Val Tyr Leu Gln Met Thr Asn Leu Arg Thr Glu Asp Thr Gly Ile Tyr
                85                  90                  95

Tyr Cys Thr Met Leu Gly Tyr Tyr Trp Gly Gln Gly Thr Thr Leu Thr
            100                 105                 110

Val Ser Ser
        115

<210> SEQ ID NO 109
<211> LENGTH: 335
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(333)

<400> SEQUENCE: 109 gac att ttg ctg act cag tct cct gct tcc tta gct gta tct ctg ggg     48
Asp Ile Leu Leu Thr Gln Ser Pro Ala Ser Leu Ala Val Ser Leu Gly
1               5                   10                  15 cag agg gcc acc atc tca tgc agg gcc agc caa agt gtc agt tca tct     96
Gln Arg Ala Thr Ile Ser Cys Arg Ala Ser Gln Ser Val Ser Ser Ser
            20                  25                  30 aga cag agt tat atg cac tgg tac caa cag aaa cca gga cag gca ccc    144
```

```
Arg Gln Ser Tyr Met His Trp Tyr Gln Gln Lys Pro Gly Gln Ala Pro
            35                  40                  45 aaa ctc ctc atc aag tat gca tcc aac cta gaa tcg ggg gtc cct gcc      192
Lys Leu Leu Ile Lys Tyr Ala Ser Asn Leu Glu Ser Gly Val Pro Ala
 50                  55                  60 agg ttc agt ggc agt ggg tct ggg aca gac ttc atc ctc aac atc cat      240
Arg Phe Ser Gly Ser Gly Ser Gly Thr Asp Phe Ile Leu Asn Ile His
 65                  70                  75                  80 cct gtg gag gag gag gat act gca aca tat tac tgt cag cac agt tgg      288
Pro Val Glu Glu Glu Asp Thr Ala Thr Tyr Tyr Cys Gln His Ser Trp
                 85                  90                  95 gag att ccg tac acg ttc gga ggg ggg acc aag ctg gaa atc aaa cg       335
Glu Ile Pro Tyr Thr Phe Gly Gly Gly Thr Lys Leu Glu Ile Lys
            100                 105                 110

<210> SEQ ID NO 110
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Asp Ile Leu Leu Thr Gln Ser Pro Ala Ser Leu Ala Val Ser Leu Gly
 1               5                  10                  15

Gln Arg Ala Thr Ile Ser Cys Arg Ala Ser Gln Ser Val Ser Ser Ser
             20                  25                  30

Arg Gln Ser Tyr Met His Trp Tyr Gln Gln Lys Pro Gly Gln Ala Pro
         35                      40                  45

Lys Leu Leu Ile Lys Tyr Ala Ser Asn Leu Glu Ser Gly Val Pro Ala
 50                  55                  60

Arg Phe Ser Gly Ser Gly Ser Gly Thr Asp Phe Ile Leu Asn Ile His
 65                  70                  75                  80

Pro Val Glu Glu Glu Asp Thr Ala Thr Tyr Tyr Cys Gln His Ser Trp
                 85                  90                  95

Glu Ile Pro Tyr Thr Phe Gly Gly Gly Thr Lys Leu Glu Ile Lys
            100                 105                 110

<210> SEQ ID NO 111
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(363)

<400> SEQUENCE: 111 gag gtg aag ctg atg aag tct gga gga ggc ttg gta cag cct ggg gct       48
Glu Val Lys Leu Met Lys Ser Gly Gly Gly Leu Val Gln Pro Gly Ala
 1               5                  10                  15 tct ctg aga ctc tcc tgt gca gct tct ggg ttc acc ttc act gat tac       96
Ser Leu Arg Leu Ser Cys Ala Ala Ser Gly Phe Thr Phe Thr Asp Tyr
             20                  25                  30 tac atg agc tgg gtc cgc cag cct cca gga aag gca ctt gag tgg ttg      144
Tyr Met Ser Trp Val Arg Gln Pro Pro Gly Lys Ala Leu Glu Trp Leu
         35                  40                  45 ggt ttt att aga aac aaa gct aat ggt tac aca aca gac tac agt gca      192
Gly Phe Ile Arg Asn Lys Ala Asn Gly Tyr Thr Thr Asp Tyr Ser Ala
```

```
                 50                   55                   60
tct gtg aag ggt cgg ttc acc atc tcc aga gat aat tcc caa agc atc      240
Ser Val Lys Gly Arg Phe Thr Ile Ser Arg Asp Asn Ser Gln Ser Ile
 65                  70                   75                   80 ctc tat ctt caa atg aac aca ctg aga cct gag gac agt gcc act tat      288
Leu Tyr Leu Gln Met Asn Thr Leu Arg Pro Glu Asp Ser Ala Thr Tyr
                 85                   90                   95 tac tgt gca aga gat gga act acg atg ggg gct gcg gac tac tgg ggc      336
Tyr Cys Ala Arg Asp Gly Thr Thr Met Gly Ala Ala Asp Tyr Trp Gly
             100                  105                  110 caa ggc acc act ctc aca gtc tcc tca                                  363
Gln Gly Thr Thr Leu Thr Val Ser Ser
            115                  120

<210> SEQ ID NO 112
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Glu Val Lys Leu Met Lys Ser Gly Gly Gly Leu Val Gln Pro Gly Ala
  1               5                  10                  15

Ser Leu Arg Leu Ser Cys Ala Ala Ser Gly Phe Thr Phe Thr Asp Tyr
             20                  25                  30

Tyr Met Ser Trp Val Arg Gln Pro Pro Gly Lys Ala Leu Glu Trp Leu
         35                  40                  45

Gly Phe Ile Arg Asn Lys Ala Asn Gly Tyr Thr Thr Asp Tyr Ser Ala
     50                  55                  60

Ser Val Lys Gly Arg Phe Thr Ile Ser Arg Asp Asn Ser Gln Ser Ile
 65                  70                  75                  80

Leu Tyr Leu Gln Met Asn Thr Leu Arg Pro Glu Asp Ser Ala Thr Tyr
                 85                  90                  95

Tyr Cys Ala Arg Asp Gly Thr Thr Met Gly Ala Ala Asp Tyr Trp Gly
             100                 105                 110

Gln Gly Thr Thr Leu Thr Val Ser Ser
            115                 120

<210> SEQ ID NO 113
<211> LENGTH: 337
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 113 gac att cag atg acg cag tct cca tcc tcc ctg gct gtg tca gca gga      48
Asp Ile Gln Met Thr Gln Ser Pro Ser Ser Leu Ala Val Ser Ala Gly
  1               5                  10                  15 gag aag gtc act atg agc tgc aaa tcc agt cag agt ctg ttc aac agt      96
Glu Lys Val Thr Met Ser Cys Lys Ser Ser Gln Ser Leu Phe Asn Ser
             20                  25                  30 aga acc cga aaa aac tac ttg gct tgg tac cag cag aaa cca ggg cag      144
Arg Thr Arg Lys Asn Tyr Leu Ala Trp Tyr Gln Gln Lys Pro Gly Gln
         35                  40                  45
```

```
tct cct aaa ctg ctg atc tac tgg gca ttt cgt agg gaa tct ggg gtc      192
Ser Pro Lys Leu Leu Ile Tyr Trp Ala Phe Arg Arg Glu Ser Gly Val
    50                  55                  60 cct gat cgc ttc acg ggc agt gga tct ggg aca gat ttc agt ttc acc      240
Pro Asp Arg Phe Thr Gly Ser Gly Ser Gly Thr Asp Phe Ser Phe Thr
65                  70                  75                  80 atc aga agt gtg cag gct gaa gac ctg gca gtt tat tac tgc aaa caa      288
Ile Arg Ser Val Gln Ala Glu Asp Leu Ala Val Tyr Tyr Cys Lys Gln
                85                  90                  95 tct tat tat ctt cgg acg ttc ggt gga ggc acc aag ctg gag ctg aaa c    337
Ser Tyr Tyr Leu Arg Thr Phe Gly Gly Gly Thr Lys Leu Glu Leu Lys
                100                 105                 110
```

<210> SEQ ID NO 114
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

```
Asp Ile Gln Met Thr Gln Ser Pro Ser Ser Leu Ala Val Ser Ala Gly
1               5                   10                  15

Glu Lys Val Thr Met Ser Cys Lys Ser Ser Gln Ser Leu Phe Asn Ser
                20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Ala Phe Arg Arg Glu Ser Gly Val
    50                  55                  60

Pro Asp Arg Phe Thr Gly Ser Gly Ser Gly Thr Asp Phe Ser Phe Thr
65                  70                  75                  80

Ile Arg Ser Val Gln Ala Glu Asp Leu Ala Val Tyr Tyr Cys Lys Gln
                85                  90                  95

Ser Tyr Tyr Leu Arg Thr Phe Gly Gly Gly Thr Lys Leu Glu Leu Lys
                100                 105                 110
```

<210> SEQ ID NO 115
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(354)

<400> SEQUENCE: 115

```
cag gtc caa ctg cag cag tct gga cct gag ctg gcg agg cct ggg gct       48
Gln Val Gln Leu Gln Gln Ser Gly Pro Glu Leu Ala Arg Pro Gly Ala
1               5                   10                  15 tca gtg aag ctg tcc tgc aag gcc tct ggc tac acc ttc agg agc tat       96
Ser Val Lys Leu Ser Cys Lys Ala Ser Gly Tyr Thr Phe Arg Ser Tyr
                20                  25                  30 ggt ata agc tgg gtg aag cag aga act gga cag ggc ctt gag tgg att      144
Gly Ile Ser Trp Val Lys Gln Arg Thr Gly Gln Gly Leu Glu Trp Ile
            35                  40                  45 gga gag att tat cct aga agt ggt aat act tac tac aat gag aag ttc      192
Gly Glu Ile Tyr Pro Arg Ser Gly Asn Thr Tyr Tyr Asn Glu Lys Phe
    50                  55                  60 aag ggc aag gcc aca ctg act gca gac aaa tcc tcc aac aca gcg tac      240
```

```
Lys Gly Lys Ala Thr Leu Thr Ala Asp Lys Ser Ser Asn Thr Ala Tyr
65                  70                  75                  80 atg gag ctc cgc agc ctg aca tct gag gac tct gcg gtc tat ttc tgt      288
Met Glu Leu Arg Ser Leu Thr Ser Glu Asp Ser Ala Val Tyr Phe Cys
                85                  90                  95 gca aga gat agt aaa gac tat gct atg gac tat tgg ggt caa gga acc      336
Ala Arg Asp Ser Lys Asp Tyr Ala Met Asp Tyr Trp Gly Gln Gly Thr
            100                 105                 110 tca gtc acc gtc tcc tca                                              354
Ser Val Thr Val Ser Ser
        115

<210> SEQ ID NO 116
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Gln Val Gln Leu Gln Gln Ser Gly Pro Glu Leu Ala Arg Pro Gly Ala
1               5                   10                  15

Ser Val Lys Leu Ser Cys Lys Ala Ser Gly Tyr Thr Phe Arg Ser Tyr
                20                  25                  30

Gly Ile Ser Trp Val Lys Gln Arg Thr Gly Gln Gly Leu Glu Trp Ile
            35                  40                  45

Gly Glu Ile Tyr Pro Arg Ser Gly Asn Thr Tyr Tyr Asn Glu Lys Phe
        50                  55                  60

Lys Gly Lys Ala Thr Leu Thr Ala Asp Lys Ser Ser Asn Thr Ala Tyr
65                  70                  75                  80

Met Glu Leu Arg Ser Leu Thr Ser Glu Asp Ser Ala Val Tyr Phe Cys
                85                  90                  95

Ala Arg Asp Ser Lys Asp Tyr Ala Met Asp Tyr Trp Gly Gln Gly Thr
            100                 105                 110

Ser Val Thr Val Ser Ser
        115

<210> SEQ ID NO 117
<211> LENGTH: 338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 117 gac gtt gtg atg acc cag act cca ctc act ttg tcg gtt acc att gga       48
Asp Val Val Met Thr Gln Thr Pro Leu Thr Leu Ser Val Thr Ile Gly
1               5                   10                  15 caa cca gcc tcc atc tct tgc aag tca agt cag agc ctc tta gat agt       96
Gln Pro Ala Ser Ile Ser Cys Lys Ser Ser Gln Ser Leu Leu Asp Ser
                20                  25                  30 gat gga aag aca tat ttg aat tgg ttg tta cag agg cca ggc cag tct      144
Asp Gly Lys Thr Tyr Leu Asn Trp Leu Leu Gln Arg Pro Gly Gln Ser
            35                  40                  45 cca aag cgc cta atc tat ctg atg tct aaa ctg gac tct gga gtc cct      192
Pro Lys Arg Leu Ile Tyr Leu Met Ser Lys Leu Asp Ser Gly Val Pro
        50                  55                  60
```

```
gac agg ttc act ggc agt gga tca ggg aca gat ttc aca ctg aaa atc      240
Asp Arg Phe Thr Gly Ser Gly Ser Gly Thr Asp Phe Thr Leu Lys Ile
 65              70                  75                  80 agc aga gtg gag gca gag gat ttg gga gtt tat tat tgc tgg caa ggt      288
Ser Arg Val Glu Ala Glu Asp Leu Gly Val Tyr Tyr Cys Trp Gln Gly
             85                  90                  95 aca cat ttt cct cac acg ttc ggt gct ggg acc aag ctg gaa ata aaa      336
Thr His Phe Pro His Thr Phe Gly Ala Gly Thr Lys Leu Glu Ile Lys
            100                 105                 110 cg                                                                    338
```

<210> SEQ ID NO 118
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

```
Asp Val Val Met Thr Gln Thr Pro Leu Thr Leu Ser Val Thr Ile Gly
 1               5                   10                  15

Gln Pro Ala Ser Ile Ser Cys Lys Ser Ser Gln Ser Leu Leu Asp Ser
             20                  25                  30

Asp Gly Lys Thr Tyr Leu Asn Trp Leu Leu Gln Arg Pro Gly Gln Ser
         35                  40                  45

Pro Lys Arg Leu Ile Tyr Leu Met Ser Lys Leu Asp Ser Gly Val Pro
     50                  55                  60

Asp Arg Phe Thr Gly Ser Gly Ser Gly Thr Asp Phe Thr Leu Lys Ile
 65              70                  75                  80

Ser Arg Val Glu Ala Glu Asp Leu Gly Val Tyr Tyr Cys Trp Gln Gly
             85                  90                  95

Thr His Phe Pro His Thr Phe Gly Ala Gly Thr Lys Leu Glu Ile Lys
            100                 105                 110
```

<210> SEQ ID NO 119
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(366)

<400> SEQUENCE: 119

```
gag gtg atg ctg gtg gag tct gga gga ggc ttg gta cag cct ggg gct       48
Glu Val Met Leu Val Glu Ser Gly Gly Gly Leu Val Gln Pro Gly Ala
 1               5                   10                  15 tct ctg aga ctc tcc tgt gca act tct ggg ttc acc ttc act gat tac       96
Ser Leu Arg Leu Ser Cys Ala Thr Ser Gly Phe Thr Phe Thr Asp Tyr
             20                  25                  30 tac atg aat tgg gtc cgc cag cct cca gga aag gca ctt gaa tgg ttg      144
Tyr Met Asn Trp Val Arg Gln Pro Pro Gly Lys Ala Leu Glu Trp Leu
         35                  40                  45 ggt ttt att aga aac aaa gct aat ggt tac aca aca gag tac agt gca      192
Gly Phe Ile Arg Asn Lys Ala Asn Gly Tyr Thr Thr Glu Tyr Ser Ala
     50                  55                  60 tct gtg aag ggt cgg ttc acc atc tcc aga gat aat tcc caa acc atc      240
Ser Val Lys Gly Arg Phe Thr Ile Ser Arg Asp Asn Ser Gln Thr Ile
```

```
                                                65                  70                  75                  80
ctc tat ctt caa atg aac aca ctg aga gct gag gac agt gcc act tat           288
Leu Tyr Leu Gln Met Asn Thr Leu Arg Ala Glu Asp Ser Ala Thr Tyr
                    85                  90                  95 tac tgt gca aga gat gcg gga tca ggg tcc cac tac ttt gac tac tgg           336
Tyr Cys Ala Arg Asp Ala Gly Ser Gly Ser His Tyr Phe Asp Tyr Trp
                100                 105                 110 ggc caa ggc acc act ctc aca gtc tcc tca                                   366
Gly Gln Gly Thr Thr Leu Thr Val Ser Ser
            115                 120

<210> SEQ ID NO 120
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Glu Val Met Leu Val Glu Ser Gly Gly Gly Leu Val Gln Pro Gly Ala
1               5                   10                  15

Ser Leu Arg Leu Ser Cys Ala Thr Ser Gly Phe Thr Phe Thr Asp Tyr
            20                  25                  30

Tyr Met Asn Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Thr Ile
65                  70                  75                  80

Leu Tyr Leu Gln Met Asn Thr Leu Arg Ala Glu Asp Ser Ala Thr Tyr
                85                  90                  95

Tyr Cys Ala Arg Asp Ala Gly Ser Gly Ser His Tyr Phe Asp Tyr Trp
            100                 105                 110

Gly Gln Gly Thr Thr Leu Thr Val Ser Ser
        115                 120

<210> SEQ ID NO 121
<211> LENGTH: 337
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 121 gac att gtg ctg aca cag tct cca tcc tcc ctg gct gtg tca gca gga            48
Asp Ile Val Leu Thr Gln Ser Pro Ser Ser Leu Ala Val Ser Ala Gly
1               5                   10                  15 gag aag gtc act atg aga tgt aaa tcc agt cag agt ctg ttc aac agt            96
Glu Lys Val Thr Met Arg Cys Lys Ser Ser Gln Ser Leu Phe Asn Ser
            20                  25                  30 aga acc cga aag aac tac ttg gct tgg tac cag cag aaa cca ggg cag           144
Arg Thr Arg Lys Asn Tyr Leu Ala Trp Tyr Gln Gln Lys Pro Gly Gln
        35                  40                  45 tct cct aaa ctg ctg atc tat tgg gca tta gct agg gaa tct ggg gtc           192
Ser Pro Lys Leu Leu Ile Tyr Trp Ala Leu Ala Arg Glu Ser Gly Val
    50                  55                  60
```

```
cct aaa cgc ttc aca ggc agt gga tct ggg aca gat ttc act ctc acc        240
Pro Lys Arg Phe Thr Gly Ser Gly Ser Gly Thr Asp Phe Thr Leu Thr
 65                  70                  75                  80 atc agc agt gtg cag gct gaa gac ctg gca gtt tat tac tgc aag caa        288
Ile Ser Ser Val Gln Ala Glu Asp Leu Ala Val Tyr Tyr Cys Lys Gln
                 85                  90                  95 tct tat tat ctt cgg acg ttc ggt gga ggc acc aag ctg gaa atc aaa c      337
Ser Tyr Tyr Leu Arg Thr Phe Gly Gly Gly Thr Lys Leu Glu Ile Lys
            100                 105                 110
```

<210> SEQ ID NO 122
<211> LENGTH: 112
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 122

```
Asp Ile Val Leu Thr Gln Ser Pro Ser Ser Leu Ala Val Ser Ala Gly
 1               5                  10                  15

Glu Lys Val Thr Met Arg Cys Lys Ser Ser Gln Ser Leu Phe Asn Ser
                20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Ala Leu Ala Arg Glu Ser Gly Val
        50                  55                  60

Pro Lys Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Lys Gln
                 85                  90                  95

Ser Tyr Tyr Leu Arg Thr Phe Gly Gly Gly Thr Lys Leu Glu Ile Lys
            100                 105                 110
```

<210> SEQ ID NO 123
<211> LENGTH: 354
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<221> NAME/KEY: CDS
<222> LOCATION: (1)..(354)

<400> SEQUENCE: 123

```
gag gtg caa ctg gtg gag tct gga gga ggc ttg gta cag cct ggg gct        48
Glu Val Gln Leu Val Glu Ser Gly Gly Gly Leu Val Gln Pro Gly Ala
 1               5                  10                  15 tct ctg aga ctc tcc tgt gca act tct ggg ttc acc ttc act gat tac        96
Ser Leu Arg Leu Ser Cys Ala Thr Ser Gly Phe Thr Phe Thr Asp Tyr
                20                  25                  30 tac atg agc tgg gtc cgc cag cct cca gga aag gca ctt gag tgg ttg        144
Tyr Met Ser Trp Val Arg Gln Pro Pro Gly Lys Ala Leu Glu Trp Leu
            35                  40                  45 ggt ttt att aga aac aaa gct aat ggt tac aca aca gag tac agt gca       192
Gly Phe Ile Arg Asn Lys Ala Asn Gly Tyr Thr Thr Glu Tyr Ser Ala
        50                  55                  60 tct gtg aag ggt cgg ttc acc atc tcc aga gat aat tcc caa agc atc       240
Ser Val Lys Gly Arg Phe Thr Ile Ser Arg Asp Asn Ser Gln Ser Ile
 65                  70                  75                  80 ctc tat ctt caa atg aac aca ctg aga gct gcg gac agt gcc act tat       288
Leu Tyr Leu Gln Met Asn Thr Leu Arg Ala Ala Asp Ser Ala Thr Tyr
```

```
Leu Tyr Leu Gln Met Asn Thr Leu Arg Ala Ala Asp Ser Ala Thr Tyr
            85                  90                  95 tac tgt gca aga gga act gga cac ttt gac tac tgg ggc caa ggc acc    336
Tyr Cys Ala Arg Gly Thr Gly His Phe Asp Tyr Trp Gly Gln Gly Thr
            100                 105                 110 act ctc aca gtc tcc tca                                            354
Thr Leu Thr Val Ser Ser
        115
```

<210> SEQ ID NO 124
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

```
Glu Val Gln Leu Val Glu Ser Gly Gly Gly Leu Val Gln Pro Gly Ala
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Ala Ala Asp Ser Ala Thr Tyr
            85                  90                  95

Tyr Cys Ala Arg Gly Thr Gly His Phe Asp Tyr Trp Gly Gln Gly Thr
            100                 105                 110

Thr Leu Thr Val Ser Ser
        115
```

<210> SEQ ID NO 125
<211> LENGTH: 337
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 125

```
gat att gtg atg aca cag tct cca tcc tcc ctg gct gtg tca gca gga     48
Asp Ile Val Met Thr Gln Ser Pro Ser Ser Leu Ala Val Ser Ala Gly
1               5                   10                  15 gag aag gtc act atg agc tgc aaa tcc agt cag agt ctg ttc aac agt     96
Glu Lys Val Thr Met Ser Cys Lys Ser Ser Gln Ser Leu Phe Asn Ser
            20                  25                  30 aga acc cga aag aac tac ttg gct tgg tac cag cag aaa cca ggg cag    144
Arg Thr Arg Lys Asn Tyr Leu Ala Trp Tyr Gln Gln Lys Pro Gly Gln
        35                  40                  45 tct cct aaa ctg ctg atc tac tgg gca tcc act agg gaa tct ggg gtg    192
Ser Pro Lys Leu Leu Ile Tyr Trp Ala Ser Thr Arg Glu Ser Gly Val
    50                  55                  60 cct gat cgc ttc aca ggc agt gga tct ggg aca gat ttc act ctc acc    240
Pro Asp Arg Phe Thr Gly Ser Gly Ser Gly Thr Asp Phe Thr Leu Thr
65                  70                  75                  80
```

```
atc agc agt gtg cag gct gaa gac ctg gca gtt tat tac tgc aag caa      288
Ile Ser Ser Val Gln Ala Glu Asp Leu Ala Val Tyr Tyr Cys Lys Gln
                85                  90                  95 tct tat tat ctt cgg acg ttc gga ggg ggg acc aag ctg gag ctg aaa c    337
Ser Tyr Tyr Leu Arg Thr Phe Gly Gly Gly Thr Lys Leu Glu Leu Lys
            100                 105                 110
```

<210> SEQ ID NO 126
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

```
Asp Ile Val Met Thr Gln Ser Pro Ser Ser Leu Ala Val Ser Ala Gly
1               5                   10                  15

Glu Lys Val Thr Met Ser Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Tyr Leu Arg Thr Phe Gly Gly Gly Thr Lys Leu Glu Leu Lys
            100                 105                 110
```

<210> SEQ ID NO 127
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(351)

<400> SEQUENCE: 127

```
cag gtc cag ctg cag cag tct gga cct gag ctg gtg aag cct ggg gct      48
Gln Val Gln Leu Gln Gln Ser Gly Pro Glu Leu Val Lys Pro Gly Ala
1               5                   10                  15 tca gtg aag atg tcc tgt aag gct tct gga tac aca ttc act gac tac      96
Ser Val Lys Met Ser Cys Lys Ala Ser Gly Tyr Thr Phe Thr Asp Tyr
            20                  25                  30 cac atg aac tgg gtg aag cag agc cat gga aag agc ctt gag tgg att     144
His Met Asn Trp Val Lys Gln Ser His Gly Lys Ser Leu Glu Trp Ile
        35                  40                  45 gga aat att aat cct tac aac ggt gat att aac tac aac cag aag ttc     192
Gly Asn Ile Asn Pro Tyr Asn Gly Asp Ile Asn Tyr Asn Gln Lys Phe
    50                  55                  60 aag ggc aag gcc aca ttg act gta gac aaa tcc tcc aga aca gcc tac     240
Lys Gly Lys Ala Thr Leu Thr Val Asp Lys Ser Ser Arg Thr Ala Tyr
65                  70                  75                  80 atg cag ctc aac agc ctg aca tct gag gac tct gca gtc tat tac tgt     288
Met Gln Leu Asn Ser Leu Thr Ser Glu Asp Ser Ala Val Tyr Tyr Cys
                85                  90                  95
```

```
gca aga gga ggg cag ctc ggg ctc gcc tac tgg ggc caa ggc acc act       336
Ala Arg Gly Gly Gln Leu Gly Leu Ala Tyr Trp Gly Gln Gly Thr Thr
            100                 105                 110 ctc aca gtc tcc tca                                                   351
Leu Thr Val Ser Ser
        115

<210> SEQ ID NO 128
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

His Met Asn Trp Val Lys Gln Ser His Gly Lys Ser Leu Glu Trp Ile
        35                  40                  45

Gly Asn Ile Asn Pro Tyr Asn Gly Asp Ile Asn Tyr Asn Gln Lys Phe
    50                  55                  60

Lys Gly Lys Ala Thr Leu Thr Val Asp Lys Ser Ser Arg Thr Ala Tyr
65                  70                  75                  80

Met Gln Leu Asn Ser Leu Thr Ser Glu Asp Ser Ala Val Tyr Tyr Cys
                85                  90                  95

Ala Arg Gly Gly Gln Leu Gly Leu Ala Tyr Trp Gly Gln Gly Thr Thr
            100                 105                 110

Leu Thr Val Ser Ser
        115

<210> SEQ ID NO 129
<211> LENGTH: 337
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 129 gac att cag atg atg cag tct cca tcc tcc ctg act gtg tca gca gga        48
Asp Ile Gln Met Met Gln Ser Pro Ser Ser Leu Thr Val Ser Ala Gly
1               5                   10                  15 gag aag gtc act atg agc tgc aaa tcc agt cag agt ctg ttc aac agt        96
Glu Lys Val Thr Met Ser Cys Lys Ser Ser Gln Ser Leu Phe Asn Ser
            20                  25                  30 aga acc cga aag aac tac ttg gct tgg tac cag cag aaa cca ggg cag       144
Arg Thr Arg Lys Asn Tyr Leu Ala Trp Tyr Gln Gln Lys Pro Gly Gln
        35                  40                  45 tct cct aaa ctg ctg atc tac tgg gca ttg att agg gaa tct ggg gtc       192
Ser Pro Lys Leu Leu Ile Tyr Trp Ala Leu Ile Arg Glu Ser Gly Val
    50                  55                  60 cct gat cgc ttc aca ggc agt gga tct ggg aca gat ttc act ctc acc       240
Pro Asp Arg Phe Thr Gly Ser Gly Ser Gly Thr Asp Phe Thr Leu Thr
65                  70                  75                  80 atc agc cgt gtg cag gct gag gac ctg gca gtt tat tac tgc aag caa       288
Ile Ser Arg Val Gln Ala Glu Asp Leu Ala Val Tyr Tyr Cys Lys Gln
```

```
                  85                  90                  95
tct tat tat ctt cgg acg ttc ggt gga ggc acc aag ctg gaa atc aaa c    337
Ser Tyr Tyr Leu Arg Thr Phe Gly Gly Gly Thr Lys Leu Glu Ile Lys
                100                 105                 110
```

<210> SEQ ID NO 130
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

```
Asp Ile Gln Met Met Gln Ser Pro Ser Ser Leu Thr Val Ser Ala Gly
1               5                   10                  15

Glu Lys Val Thr Met Ser Cys Lys Ser Ser Gln Ser Leu Phe Asn Ser
                20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Ala Leu Ile Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Arg Val Gln Ala Glu Asp Leu Ala Val Tyr Tyr Cys Lys Gln
                85                  90                  95

Ser Tyr Tyr Leu Arg Thr Phe Gly Gly Gly Thr Lys Leu Glu Ile Lys
                100                 105                 110
```

<210> SEQ ID NO 131
<211> LENGTH: 352
<212> TYPE: PRT
<213> ORGANISM: Homo sapiens

<400> SEQUENCE: 131

```
Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
                20                  25                  30

Asn Ala Asn Phe Asn Lys Ile Phe Leu Pro Thr Ile Tyr Ser Ile Ile
            35                  40                  45

Phe Leu Thr Gly Ile Val Gly Asn Gly Leu Val Ile Leu Val Met Gly
        50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
                100                 105                 110

His Val Ile Tyr Thr Val Asn Leu Tyr Ser Ser Val Leu Ile Leu Ala
            115                 120                 125

Phe Ile Ser Leu Asp Arg Tyr Leu Ala Ile Val His Ala Thr Asn Ser
        130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175
```

```
Val Ser Glu Ala Asp Asp Arg Tyr Ile Cys Asp Arg Phe Tyr Pro Asn
            180                 185                 190

Asp Leu Trp Val Val Phe Gln Phe Gln His Ile Met Val Gly Leu
        195                 200                 205

Ile Leu Pro Gly Ile Val Ile Leu Ser Cys Tyr Cys Ile Ile Ile Ser
210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                    245                 250                 255

Ile Gly Ile Ser Ile Asp Ser Phe Ile Leu Leu Glu Ile Ile Lys Gln
                260                 265                 270

Gly Cys Glu Phe Glu Asn Thr Val His Lys Trp Ile Ser Ile Thr Glu
            275                 280                 285

Ala Leu Ala Phe Phe His Cys Cys Leu Asn Pro Ile Leu Tyr Ala Phe
        290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
                340                 345                 350

<210> SEQ ID NO 132
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Lys or Arg
<220> FEATURE:
<221> NAME/KEY: MOD_RES
<222> LOCATION: (10)..(10)
<223> OTHER INFORMATION: Lys or Thr

<400> SEQUENCE: 132

Ile Arg Asn Xaa Ala Asn Gly Tyr Thr Xaa
1               5                   10

<210> SEQ ID NO 133
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phe or Leu

<400> SEQUENCE: 133

Gln Ser Leu Xaa Asn Ser Arg Thr Arg Lys Asn Tyr
1               5                   10

<210> SEQ ID NO 134
<211> LENGTH: 11
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Phe or Tyr

<400> SEQUENCE: 134

Gln Ser Leu Val His Ser Asn Gly Asn Thr Xaa
1               5                   10

<210> SEQ ID NO 135
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys or Thr
<220> FEATURE:
<221> NAME/KEY: MOD_RES
<222> LOCATION: (4)..(4)
<223> OTHER INFORMATION: Tyr, Ser or Asn
<220> FEATURE:
<221> NAME/KEY: MOD_RES
<222> LOCATION: (8)..(8)
<223> OTHER INFORMATION: Thr or Ala

<400> SEQUENCE: 135

Xaa Gln Ser Xaa Tyr Leu Arg Xaa
1               5

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Ile

<400> SEQUENCE: 136

Ser Gln Xaa Thr His Val Pro Trp Thr
1               5

<210> SEQ ID NO 137
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gly Val Asn Lys
1

<210> SEQ ID NO 138
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 138

Glu Ile Glu Asn Thr
1               5

<210> SEQ ID NO 139
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Asn Glu Ala Gln
1

<210> SEQ ID NO 140
<211> LENGTH: 38
<212> TYPE: PRT
<213> ORGANISM: Homo sapiens

<400> SEQUENCE: 140

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys
            35

<210> SEQ ID NO 141
<211> LENGTH: 11
<212> TYPE: PRT
<213> ORGANISM: Homo sapiens

<400> SEQUENCE: 141

Ala Asn Trp Tyr Phe Gly Asn Phe Leu Cys Lys
1               5                   10

<210> SEQ ID NO 142
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gln Gly Asp Ile Ser
1               5

<210> SEQ ID NO 143
<211> LENGTH: 21
<212> TYPE: PRT
<213> ORGANISM: Homo sapiens

<400> SEQUENCE: 143

Ala Asn Val Ser Glu Ala Asp Asp Arg Tyr Ile Cys Asp Arg Phe Tyr
1               5                   10                  15

Pro Asn Asp Leu Trp
            20

<210> SEQ ID NO 144
<211> LENGTH: 21
```

```
<212> TYPE: PRT
<213> ORGANISM: Homo sapiens

<400> SEQUENCE: 144

Asp Ser Phe Ile Leu Leu Glu Ile Ile Lys Gln Gly Cys Glu Phe Glu
1               5                   10                  15

Asn Thr Val His Lys
            20
```